(12) United States Patent
Medintz et al.

(10) Patent No.: US 11,371,079 B2
(45) Date of Patent: Jun. 28, 2022

(54) FLUORESCENCE-BASED COMPUTATION SYSTEM

(71) Applicant: The Government of the United States of America, as represented by the Secretary of the Navy, Arlington, VA (US)

(72) Inventors: Igor L. Medintz, Springfield, VA (US); Mario Ancona, Alexandria, VA (US); W. Russ Algar, Vancouver (CA); Melissa M. Massey, Vancouver (CA)

(73) Assignee: The Government of the United States of America, as represented by the Secretary of the Navy, Washington, DC (US)

( * ) Notice: Subject to any disclaimer, the term of this patent is extended or adjusted under 35 U.S.C. 154(b) by 338 days.

(21) Appl. No.: 16/580,489

(22) Filed: Sep. 24, 2019

(65) Prior Publication Data

US 2020/0010877 A1   Jan. 9, 2020

Related U.S. Application Data

(62) Division of application No. 15/468,767, filed on Mar. 24, 2017, now Pat. No. 10,465,233.

(60) Provisional application No. 62/313,205, filed on Mar. 25, 2016.

(51) Int. Cl.
*C12Q 1/6818*   (2018.01)

(52) U.S. Cl.
CPC .................... *C12Q 1/6818* (2013.01)

(58) Field of Classification Search
CPC ...... C12Q 1/68; C12Q 1/6876; C12Q 1/6818; C07H 21/00; C12P 19/34
See application file for complete search history.

(56) References Cited

U.S. PATENT DOCUMENTS

| 6,902,900 B2 | 6/2005 | Davies et al. | |
| 8,476,083 B1 | 7/2013 | Algar et al. | |
| 10,465,233 B2 | 11/2019 | Medintz | C12Q 1/6818 |
| 2004/0239922 A1* | 12/2004 | Modlin | G01N 21/6452 356/317 |
| 2006/0121544 A1* | 6/2006 | Boge | C12Q 1/37 435/7.92 |
| 2010/0021901 A1 | 1/2010 | Yin et al. | |
| 2013/0108642 A1 | 5/2013 | Ibrahim | C07K 14/37 424/139.1 |
| 2014/0017669 A1 | 1/2014 | Todd | C12Q 1/682 435/5 |
| 2015/0293022 A1 | 10/2015 | Buckhout-White | C12Q 1/6818 506/9 |

FOREIGN PATENT DOCUMENTS

| CN | 2008-10117955 | 8/2008 |
| WO | WO-2008092120 A1 | 7/2008 |
| WO | WO-2010084015 A1 | 7/2010 |
| WO | WO 2013/062931 | 2/2013 |
| WO | WO-2015181101 A1 | 12/2015 |

OTHER PUBLICATIONS

Claussen et al.,Biophotonic logic devices based on quantum dots and temporally-staggered Forster energy transfer relays. Nanoscale 5 :12156-12170 (Year: 2013).*
DeSilva et al., Molecular logic and computing. Nature Nanotechnology 2 : 399 (Year: 2007).*
Graham et al.,Quantitative mapping of aqueous microfluidic temperature with sub-degree resolution using fluorescence lifetime imaging microscopy. Lab Chip 10:1267 (Year: 2010).*
Liu et al., Multiplexed Aptasensors and Amplified DNA Sensors Using Functionalized Graphene Oxide: Application for Logic Gate Operations. ACS Nano 6(4) :3553 (Year: 2012).*
Magri et al., From complexation to computation: Recent progress in molecular logic. Inorganica Chemica Acta 360:751-764 (Year: 2007).*
Massey et al. Time-Gated FRET and DNA-Based Photonic Molecular Logic gates : AND, OR, NAND and NOR. ACS Sensors 2(8) :1205-1214 (Year: 2017).*
Motornov et al., Nano Letters 8 (9) : 2993-2997 (Year: 2008).*
Saghatelian et al., JACS 125 :346-347 (Year: 2003).*
Yuan et al., J. of Organic Chemistry 73 :5008-5014 (Year: 2008).*
Johansson et al. , Time Galing Improves Sensitivity in Energy Transfer Assays with Terbium Chelate/Dark Quencher Oligonucleotide Probes. JACS126 (50): 15451 (Year: 2004).
Krasnoperov et al.,Luminescent Probes for Ultrasensitive Detection of Nucleic Acids. Bioconjugate Chemistry 21 :319 (Year: 2010).
Li et al.,Design of a Room-Temperature Phosphorescence-Based Molecular Beacon for Highly Sensitive Detection of Nucleic Acids in Biological Fluids. Analytical Chemistry 83 : 1356 (Year: 2011).
Lopez-Crapez et alA homogeneous europium cryptate-based assay for the diagnosis of mutations by time-resolved fluorescence resonance energy transfer. Nucleic Acids Research 29(14) : e70 (Year: 2001).
Srinivas et al.On the biophysics and kinetics of toehold-mediated DNA strand displacement. Nucleic Acids Research 41(22) :10641-10658 (Year: 2013).
Tyagi et al. Multicolor molecular beacons for allele discrimination. Nature Biotechnology 16 :49 (Year: 1998).
Zhang et al., Control of DNA Strand Displacement Kinetics Using Toehold Exchange. JACS 131 :17303 (Year: 2009).
HTRF Theory in Brief. Cisbio Product and Services Catalog.

(Continued)

*Primary Examiner* — Ethan C Whisenant
(74) *Attorney, Agent, or Firm* — US Naval Research Laboratory; Roy Roberts

(57) ABSTRACT

Time-resolved nucleic acids include a long-lifetime FRET donor with an emission lifetime of at least one millisecond (such as a terbium complex), configured as a donor in a first FRET process, and at least one fluorescent dye with an emission lifetime of less than 100 nanoseconds configured as an acceptor in the FRET process. They can be configured as photonic wires, hybridization probes or beacons, and/or systems for computing logical operations.

1 Claim, 38 Drawing Sheets

Specification includes a Sequence Listing.

(56) References Cited

OTHER PUBLICATIONS

LanthaScreen Technology Overview. https://www.thermofisher.com/US/en/home/industrial/pharma-biopharma/drug-discovery-development/target-and-lead-identification-and-validatlon/kinasebiology/kinase-activity-assays/lanthascreen-tr-fret-toolbox/lanthascreen-tr-fret-technology-overview.html.

Massey et al., "Time-Gated DNA Photonic Wires with Förster Resonance Energy Transfer Cascades Initiated by a Luminescent Terbium Donor" *ACS Photonics* 2015, 2, 639-652.

Massey et al., "Time-Resolved Nucleic Acid Hybridization Beacons Utilizing Unimolecular and Toehold-Mediated Strand Displacement Designs" *Anal. Chem.* 2015, 87, 11923-11931.

Tyagi S; Kramer FR (1996), "Molecular beacons: probes that fluoresce upon hybridization". Nat. Biotechnol. 14 (3): 303-8.

Pinheiro et al., Challenges and opportunities for structural DNA nanotechnology. Nature Nanotechnology 6: 763 . (Year: 2011).

Seelig et al., Enzyme-Free Nucleic Acid Logic Circuits. Science 314 :1585 (Year: 2006).

Wagner et al., A Molecular Photonic Wire. JACS 116 :9759 (Year: 1994).

Zhang et al., Nature Chemistry 4:208 (Year: 2012).

Graugnard et al.,DNA-Conlrolled Excitonic Switches. NANO Letters12 :2117 (Year: 2012).

Hannestad et al., Self-Assembled DNA Photonic Wire for Long-Range Energy Transfer. JACS 130 :15889 (Year: 2008).

Hellemann et al., Multistep Energy Transfer in Single Molecular Photonic Wires. JACS 126 :6514 (Year: 2004).

Hellemann et al., Dissecting and Reducing the Heterogeneity of Excited-State Energy Transport in DNA-Based Photonic Wires. JACS 128 :16,864 (Year: 2006).

Hildebrandt et al., Luminescent terbium complexes: Superior Förster resonance energy transfer donors for flexible and sensitive multiplexed biosensing. Coordination Chemistry Reviews 273-274: 125 (Year: 2014).

Kawahara et al., Sequential multistep energy transfer: enhancement of efficiency of long-range fluorescence resonance energy transfer. Chem Commun., 1999:53. (Year: 1999).

Koshkin et al., Tetrahedron 54:3607 (Year: 1998).

Ohya et al., Bioconjugate Chemistry 14(6) : 1057 (Year: 2003).

Selvin et al.,Luminescence Resonance Energy Transfer. JACS116 : 6029 (Year: 1994).

Selvin et al., PNAS 91 : 10024 (Year: 1994).

Serin et al., ChemCommun. 2002 :2605 (Year: 2002).

Singh et al., ChemCommun.1998:455 (Year: 1998).

\* cited by examiner

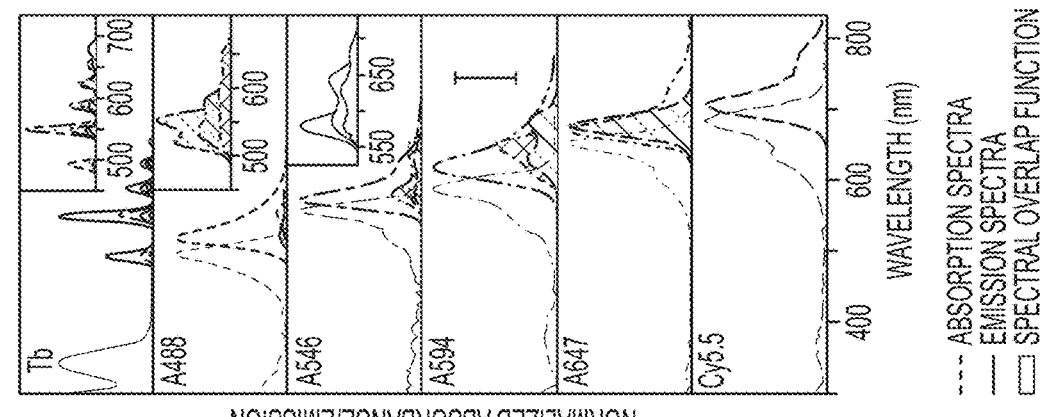
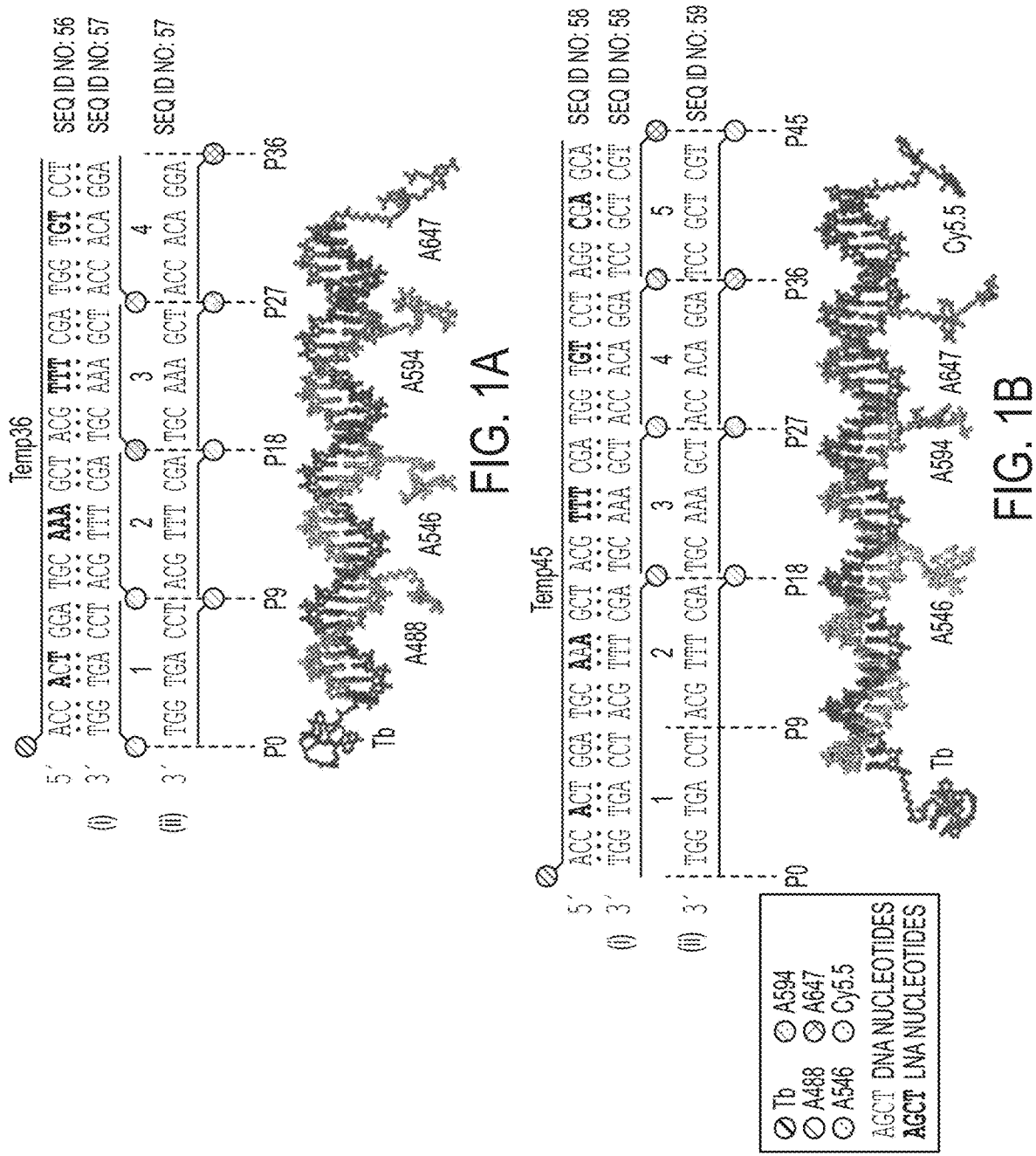
FIG. 1A
FIG. 1B
FIG. 1C

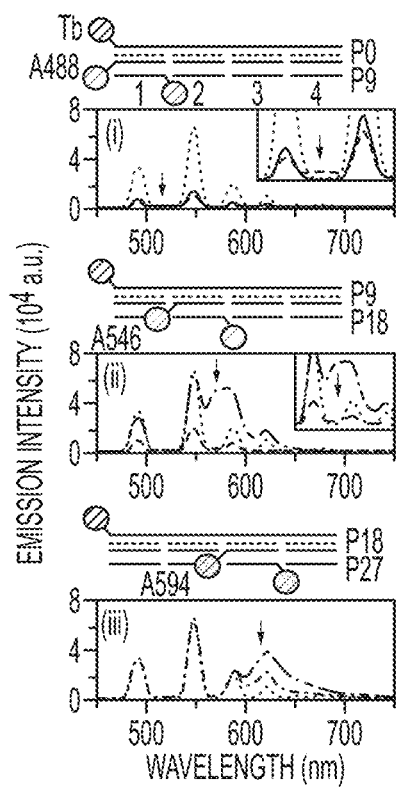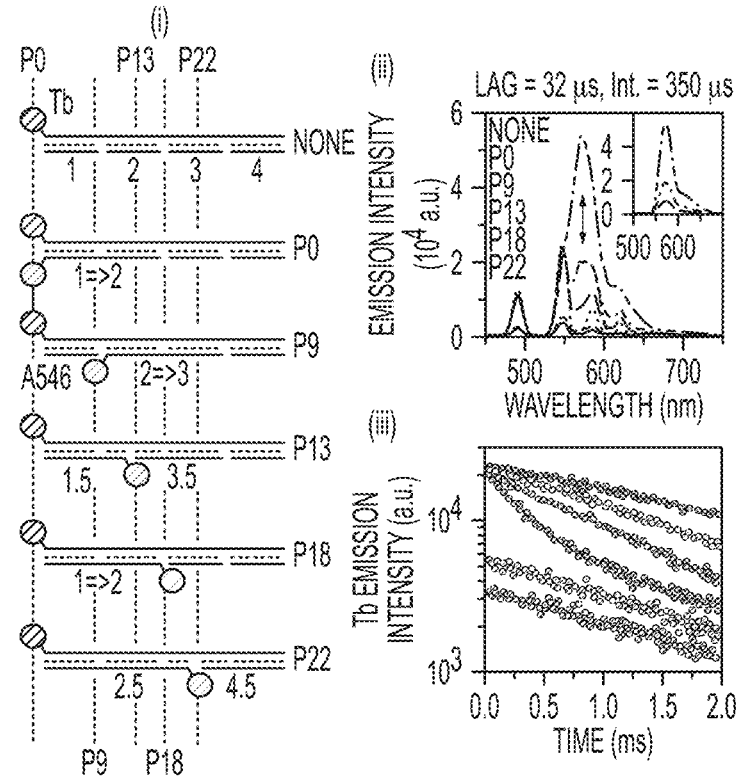
FIG. 3A
FIG. 3B
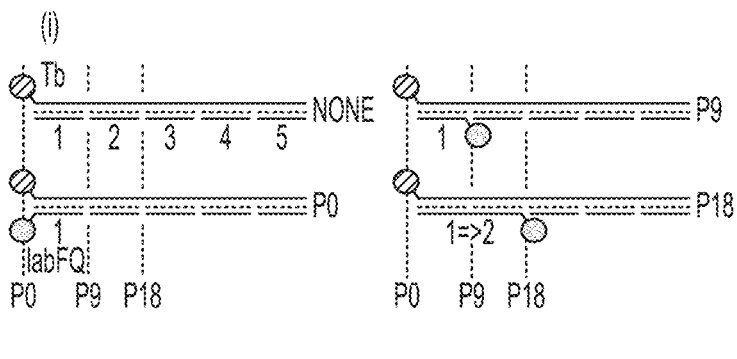
FIG. 3C

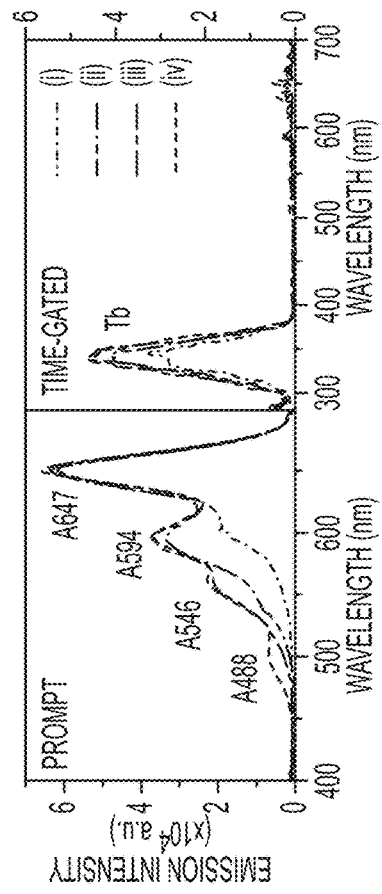
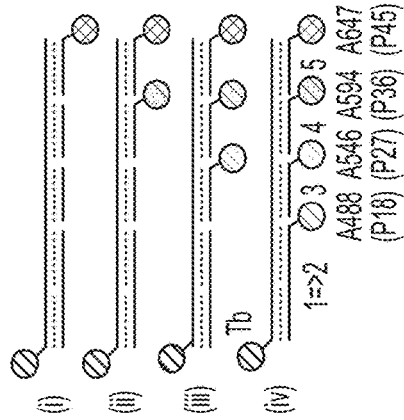
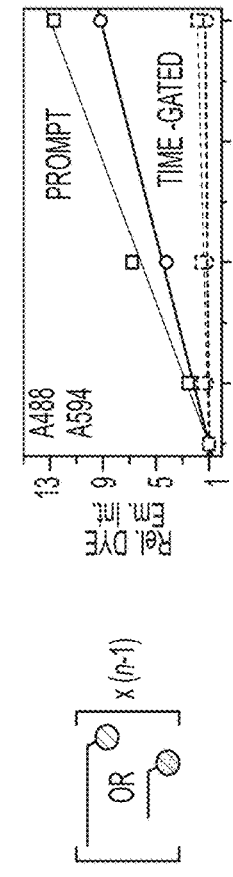
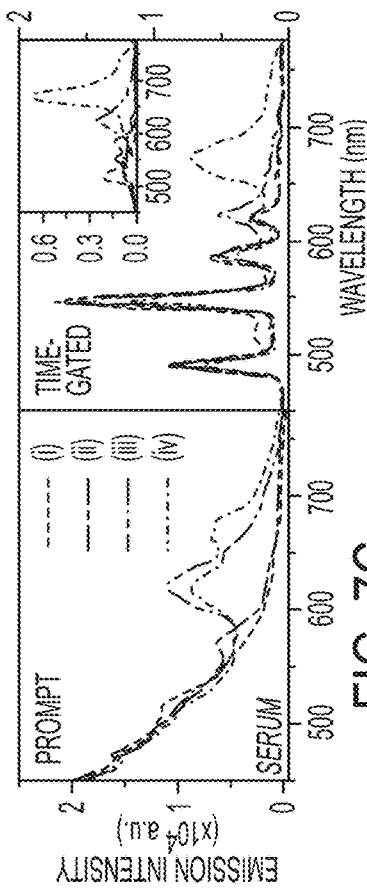
FIG. 7A
FIG. 7B
FIG. 7C

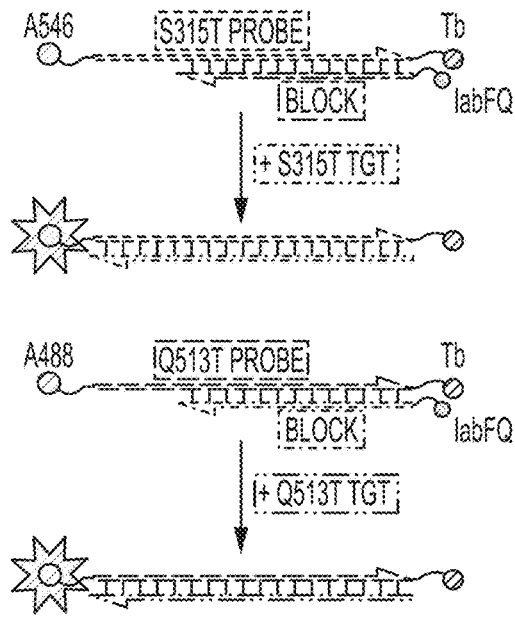
FIG. 13A
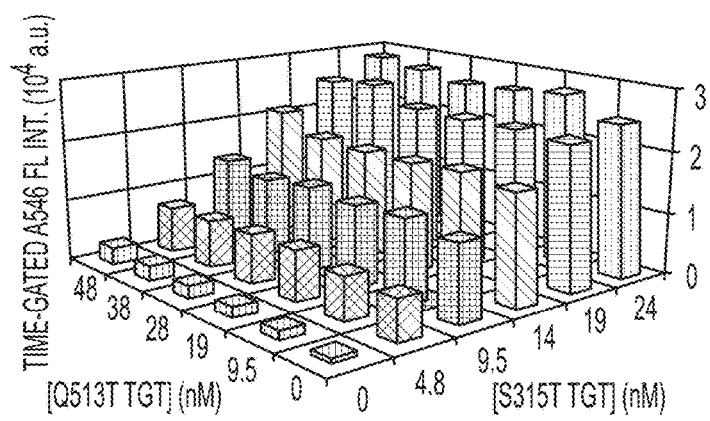
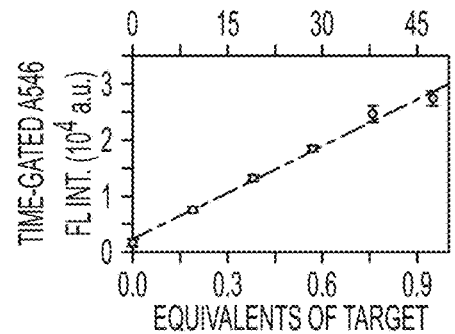
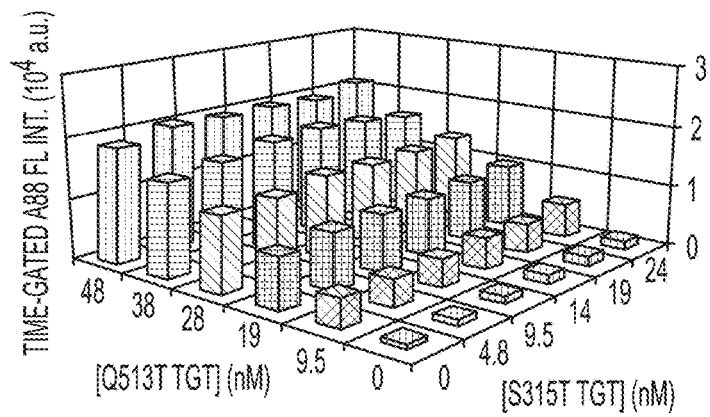
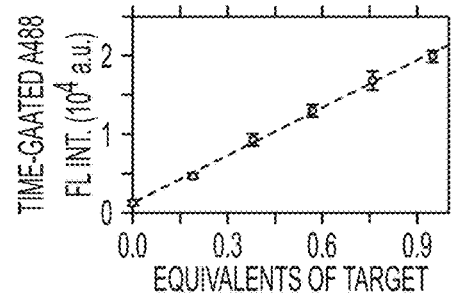
FIG. 13B
FIG. 13C

| AND | | | OR | | | NAND | | | NOR | | |
|---|---|---|---|---|---|---|---|---|---|---|---|
| INPUT 1 | INPUT 2 | OUTPUT | INPUT 1 | INPUT 2 | OUTPUT | INPUT 1 | INPUT 2 | OUTPUT | INPUT 1 | INPUT 2 | OUTPUT |
| 0 | 0 | 0 | 0 | 0 | 0 | 0 | 0 | 1 | 0 | 0 | 1 |
| 0 | 1 | 0 | 0 | 1 | 1 | 0 | 1 | 1 | 0 | 1 | 0 |
| 1 | 0 | 0 | 1 | 0 | 1 | 1 | 0 | 1 | 1 | 0 | 0 |
| 1 | 1 | 1 | 1 | 1 | 1 | 1 | 1 | 0 | 1 | 1 | 0 |

FIG. 18

PRIOR ART

| INPUT | STATE | OUTPUT |
|---|---|---|
| (0,0) | A546 — Tb — A546 / labFQ labFQ | 0 |
| (1,0) | | 0 |
| (0,1) | | 0 |
| (1,1) | | 1 |

FIG. 19

| INPUT | STATE | OUTPUT |
|---|---|---|
| (0,0) | labFQ  A546  Tb  labFQ | 0 |
| (1,0) |  | 0 |
| (0,1) |  | 0 |
| (1,1) |  | 1 |

FIG. 25

| INPUT | STATE | OUTPUT |
|---|---|---|
| (0,0) | A546 — Tb — A546 / BHQ | 0 |
| (1,0) | | 1 |
| (0,1) | | 1 |
| (1,1) | | 1 |

FIG. 27

| INPUT | STATE | OUTPUT |
|---|---|---|
| (0,0) | labFQ◯◯A546   Tb | 0 |
| (1,0) | | 1 |
| (0,1) | | 1 |
| (1,1) | | 1 |

FIG. 29

| INPUT | STATE | OUTPUT |
|---|---|---|
| (0,0) |  A546  Tb labFQ | 0 |
| (1,0) |  | 1 |
| (0,1) |  | 1 |
| (1,1) |  | 1 |

| INPUT | STATE | OUTPUT |
|---|---|---|
| (0,0) |  | 0 |
| (1,0) |  | 1 |
| (0,1) |  | 1 |
| (1,1) |  | 0 |

| INPUT | STATE | OUTPUT |
|---|---|---|
| (0,0) |  A546  Tb | 1 |
| (1,0) |  | 0 |
| (0,1) |  | 0 |
| (1,1) |  | 0 |

SEQUENCE LISTING

<160> NUMBER OF SEQ ID NOS: 59

<210> SEQ ID NO 1
<211> LENGTH: 13
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Alexa Fluor 546

<400> SEQUENCE: 1
tgcatccagt ggt                                                          13

<210> SEQ ID NO 2
<211> LENGTH: 14
<212> TYPE: DNA
<213> ORGANISM: Artificial Sequence
<220> FEATURE:
<223> OTHER INFORMATION: synthetic construct

<400> SEQUENCE: 2
tcgaaacgta gctt                                                         14

<210> SEQ ID NO 3
<211> LENGTH: 14
<212> TYPE: DNA
<213> ORGANISM: Artificial Sequence
<220> FEATURE:
<223> OTHER INFORMATION: synthetic construct

<400> SEQUENCE: 3
aggacaccat cgaa                                                         14

<210> SEQ ID NO 4
<211> LENGTH: 18
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Alexa Fluor 488

<400> SEQUENCE: 4
agctttgcat ccagtggt                                                     18

<210> SEQ ID NO 5
<211> LENGTH: 18
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Alexa Fluor 546

<400> SEQUENCE: 5
agctttgcat ccagtggt                                                     18

<210> SEQ ID NO 6
<211> LENGTH: 18
<212> TYPE: DNA
<213> ORGANISM: Artificial Sequence

```
<220> FEATURE:
<223> OTHER INFORMATION: synthetic construct
<220> FEATURE:
<221> NAME/KEY: misc_feature
<222> LOCATION: (18)..(18)
<223> OTHER INFORMATION: Alexa Fluor 546

<400> SEQUENCE: 6
agctttgcat ccagtggt                                                 18

<210> SEQ ID NO 7
<211> LENGTH: 18
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Iowa Black FQ

<400> SEQUENCE: 7
agctttgcat ccagtggt                                                 18

<210> SEQ ID NO 8
<211> LENGTH: 22
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Alexa Fluor 546

<400> SEQUENCE: 8
acgtagcttt gcatccagtg gt                                            22

<210> SEQ ID NO 9
<211> LENGTH: 18
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (18)..(18)
<223> OTHER INFORMATION: Alexa Fluor 546

<400> SEQUENCE: 9
tcgaaacgta gctttgca                                                 18

<210> SEQ ID NO 10
<211> LENGTH: 27
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Alexa Fluor 546

<400> SEQUENCE: 10
tcgaaacgta gctttgcatc cagtggt                                       27

<210> SEQ ID NO 11
<211> LENGTH: 36
<212> TYPE: DNA
```

```
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Alexa Fluor 546

<400> SEQUENCE: 11
aggacaccat cgaaacgtag ctttgcatcc agtggt                                 36

<210> SEQ ID NO 12
<211> LENGTH: 18
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Alexa Fluor 488
<220> FEATURE:
<221> NAME/KEY: misc_feature
<222> LOCATION: (18)..(18)
<223> OTHER INFORMATION: Lumi4-Tb cryptate

<400> SEQUENCE: 12
taggctcagc tggctggt                                                     18

<210> SEQ ID NO 13
<211> LENGTH: 13
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: IabFQ, A488, or A594

<400> SEQUENCE: 13
accagccagc tga                                                          13

<210> SEQ ID NO 14
<211> LENGTH: 18
<212> TYPE: DNA
<213> ORGANISM: Artificial Sequence
<220> FEATURE:
<223> OTHER INFORMATION: synthetic construct

<400> SEQUENCE: 14
accagccagc tgagccta                                                     18

<210> SEQ ID NO 15
<211> LENGTH: 18
<212> TYPE: DNA
<213> ORGANISM: Artificial Sequence
<220> FEATURE:
<223> OTHER INFORMATION: synthetic construct

<400> SEQUENCE: 15
accagccagc tgagccaa                                                     18

<210> SEQ ID NO 16
<211> LENGTH: 18
<212> TYPE: DNA
<213> ORGANISM: Artificial Sequence
<220> FEATURE:
<223> OTHER INFORMATION: synthetic construct
```

-continued

```
<220> FEATURE:
<221> NAME/KEY: misc_feature
<222> LOCATION: (1)..(1)
<223> OTHER INFORMATION: Alexa Fluor 546
<220> FEATURE:
<221> NAME/KEY: misc_feature
<222> LOCATION: (18)..(18)
<223> OTHER INFORMATION: Lumi4-Tb cryptate

<400> SEQUENCE: 16
cgtggtgatc gcgtcctt                                                 18

<210> SEQ ID NO 17
<211> LENGTH: 13
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: IabFQ, A488, or A546

<400> SEQUENCE: 17
aaggacgcga tca                                                      13

<210> SEQ ID NO 18
<211> LENGTH: 18
<212> TYPE: DNA
<213> ORGANISM: Artificial Sequence
<220> FEATURE:
<223> OTHER INFORMATION: synthetic construct

<400> SEQUENCE: 18
aaggacgcga tcaccacg                                                 18

<210> SEQ ID NO 19
<211> LENGTH: 18
<212> TYPE: DNA
<213> ORGANISM: Artificial Sequence
<220> FEATURE:
<223> OTHER INFORMATION: synthetic construct

<400> SEQUENCE: 19
aaggacgcga tcaccagc                                                 18

<210> SEQ ID NO 20
<211> LENGTH: 18
<212> TYPE: DNA
<213> ORGANISM: Artificial Sequence
<220> FEATURE:
<223> OTHER INFORMATION: synthetic construct

<400> SEQUENCE: 20
acttccggtc tcaatgaa                                                 18

<210> SEQ ID NO 21
<211> LENGTH: 37
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (18)..(18)
<223> OTHER INFORMATION: Alexa Fluor 546

<400> SEQUENCE: 21
```
taggctcagc tggctggttc gtggtgatcg cttcctt					37

<210> SEQ ID NO 22
<211> LENGTH: 13
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Iowa Black Dark Quencher

<400> SEQUENCE: 22
accagccagc tga					13

<210> SEQ ID NO 23
<211> LENGTH: 13
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (13)..(13)
<223> OTHER INFORMATION: Iowa Black Dark Quencher

<400> SEQUENCE: 23
aaggacgcga tca					13

<210> SEQ ID NO 24
<211> LENGTH: 18
<212> TYPE: DNA
<213> ORGANISM: Artificial Sequence
<220> FEATURE:
<223> OTHER INFORMATION: synthetic construct

<400> SEQUENCE: 24
accagccagc tgagccta					18

<210> SEQ ID NO 25
<211> LENGTH: 18
<212> TYPE: DNA
<213> ORGANISM: Artificial Sequence
<220> FEATURE:
<223> OTHER INFORMATION: synthetic construct

<400> SEQUENCE: 25
aaggaccgca tcaccacg					18

<210> SEQ ID NO 26
<211> LENGTH: 55
<212> TYPE: DNA
<213> ORGANISM: Artificial Sequence
<220> FEATURE:
<223> OTHER INFORMATION: synthetic construct

<400> SEQUENCE: 26
taggctcagc tggctggtaa ggacgcgatc accacgcagt gaagcggtac atagg					55

<210> SEQ ID NO 27
<211> LENGTH: 18
<212> TYPE: DNA
<213> ORGANISM: Artificial Sequence
<220> FEATURE:
<223> OTHER INFORMATION: synthetic construct
<220> FEATURE:
<221> NAME/KEY: misc_feature

```
<222> LOCATION: (18)..(18)
<223> OTHER INFORMATION: Lumi4-Tb cryptate

<400> SEQUENCE: 27
cgtggtgatc gcgtcctt                                                       18

<210> SEQ ID NO 28
<211> LENGTH: 13
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Iowa Black Dark Quencher

<400> SEQUENCE: 28
accagccagc tga                                                            13

<210> SEQ ID NO 29
<211> LENGTH: 14
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (14)..(14)
<223> OTHER INFORMATION: Iowa Black Dark Quencher

<400> SEQUENCE: 29
gtaccgcttc actg                                                           14

<210> SEQ ID NO 30
<211> LENGTH: 17
<212> TYPE: DNA
<213> ORGANISM: Artificial Sequence
<220> FEATURE:
<223> OTHER INFORMATION: synthetic construct

<400> SEQUENCE: 30
accagccagc tagccta                                                        17

<210> SEQ ID NO 31
<211> LENGTH: 19
<212> TYPE: DNA
<213> ORGANISM: Artificial Sequence
<220> FEATURE:
<223> OTHER INFORMATION: synthetic construct

<400> SEQUENCE: 31
cctatgtacc gcttcactg                                                      19

<210> SEQ ID NO 32
<211> LENGTH: 37
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (18)..(18)
<223> OTHER INFORMATION: Alexa Fluor 546

<400> SEQUENCE: 32
taggctcagc tggctggttc gtggtgatcg cttcctt                                  37
```

<210> SEQ ID NO 33
<211> LENGTH: 28
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (16)..(16)
<223> OTHER INFORMATION: Black Hole Quencher 2

<400> SEQUENCE: 33
cgcgttcacc tcgaaaccac ccacctga                                    28

<210> SEQ ID NO 34
<211> LENGTH: 18
<212> TYPE: DNA
<213> ORGANISM: Artificial Sequence
<220> FEATURE:
<223> OTHER INFORMATION: synthetic construct

<400> SEQUENCE: 34
accagccagc tgagccta                                               18

<210> SEQ ID NO 35
<211> LENGTH: 18
<212> TYPE: DNA
<213> ORGANISM: Artificial Sequence
<220> FEATURE:
<223> OTHER INFORMATION: synthetic construct

<400> SEQUENCE: 35
aaggaccgca tcaccacg                                               18

<210> SEQ ID NO 36
<211> LENGTH: 32
<212> TYPE: DNA
<213> ORGANISM: Artificial Sequence
<220> FEATURE:
<223> OTHER INFORMATION: synthetic construct

<400> SEQUENCE: 36
cgcgatcacc acgcagtgaa gcggtacata gg                               32

<210> SEQ ID NO 37
<211> LENGTH: 18
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Alexa Fluor 546
<220> FEATURE:
<221> NAME/KEY: misc_feature
<222> LOCATION: (18)..(18)
<223> OTHER INFORMATION: Lumi4-Tb cryptate

<400> SEQUENCE: 37
cgtggtgatc gcgtcctt                                               18

<210> SEQ ID NO 38
<211> LENGTH: 14
<212> TYPE: DNA
<213> ORGANISM: Artificial Sequence
<220> FEATURE:
<223> OTHER INFORMATION: synthetic construct

```
<220> FEATURE:
<221> NAME/KEY: misc_feature
<222> LOCATION: (14)..(14)
<223> OTHER INFORMATION: Iowa Black Dark Quencher

<400> SEQUENCE: 38
gtaccgcttc actg                                                         14

<210> SEQ ID NO 39
<211> LENGTH: 18
<212> TYPE: DNA
<213> ORGANISM: Artificial Sequence
<220> FEATURE:
<223> OTHER INFORMATION: synthetic construct

<400> SEQUENCE: 39
aaggacgcga tcaccacg                                                     18

<210> SEQ ID NO 40
<211> LENGTH: 19
<212> TYPE: DNA
<213> ORGANISM: Artificial Sequence
<220> FEATURE:
<223> OTHER INFORMATION: synthetic construct

<400> SEQUENCE: 40
cctatgtacc gcttcactg                                                    19

<210> SEQ ID NO 41
<211> LENGTH: 33
<212> TYPE: DNA
<213> ORGANISM: Artificial Sequence
<220> FEATURE:
<223> OTHER INFORMATION: synthetic construct

<400> SEQUENCE: 41
taggctcagc tggctggtaa ggacgctatc acc                                    33

<210> SEQ ID NO 42
<211> LENGTH: 13
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)

<400> SEQUENCE: 42
accagccagc tga                                                          13

<210> SEQ ID NO 43
<211> LENGTH: 18
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Alexa Fluor 546
<220> FEATURE:
<221> NAME/KEY: misc_feature
<222> LOCATION: (18)..(18)
<223> OTHER INFORMATION: Lumi4-Tb cryptate

<400> SEQUENCE: 43
cgtggtgatc gcgtcctt                                                     18
```

<210> SEQ ID NO 44
<211> LENGTH: 18
<212> TYPE: DNA
<213> ORGANISM: Artificial Sequence
<220> FEATURE:
<223> OTHER INFORMATION: synthetic construct

<400> SEQUENCE: 44
accagccagc tgagccta                                                   18

<210> SEQ ID NO 45
<211> LENGTH: 18
<212> TYPE: DNA
<213> ORGANISM: Artificial Sequence
<220> FEATURE:
<223> OTHER INFORMATION: synthetic construct

<400> SEQUENCE: 45
aaggaccgca tcaccacg                                                   18

<210> SEQ ID NO 46
<211> LENGTH: 36
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (18)..(18)
<223> OTHER INFORMATION: Lumi4-Tb cryptate

<400> SEQUENCE: 46
taggctcagc tggctggtcg tggtgatcgc gtcctt                               36

<210> SEQ ID NO 47
<211> LENGTH: 17
<212> TYPE: DNA
<213> ORGANISM: Artificial Sequence
<220> FEATURE:
<223> OTHER INFORMATION: synthetic construct

<400> SEQUENCE: 47
acgtaccagc cagctga                                                    17

<210> SEQ ID NO 48
<211> LENGTH: 15
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Alexa Fluor 546

<400> SEQUENCE: 48
aaggacgcta tcacc                                                      15

<210> SEQ ID NO 49
<211> LENGTH: 18
<212> TYPE: DNA
<213> ORGANISM: Artificial Sequence
<220> FEATURE:
<223> OTHER INFORMATION: synthetic construct

<400> SEQUENCE: 49
accagccagc tgagccta                                                    18

<210> SEQ ID NO 50
<211> LENGTH: 18
<212> TYPE: DNA
<213> ORGANISM: Artificial Sequence
<220> FEATURE:
<223> OTHER INFORMATION: synthetic construct

<400> SEQUENCE: 50
aaggaccgca tcaccacg                                                    18

<210> SEQ ID NO 51
<211> LENGTH: 33
<212> TYPE: DNA
<213> ORGANISM: Artificial Sequence
<220> FEATURE:
<223> OTHER INFORMATION: synthetic construct

<400> SEQUENCE: 51
taggctcagc tggctggtaa ggacgctatc acc                                   33

<210> SEQ ID NO 52
<211> LENGTH: 13
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Lumi4-Tb cryptate

<400> SEQUENCE: 52
accagccagc tga                                                         13

<210> SEQ ID NO 53
<211> LENGTH: 18
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Alexa Fluor 546

<400> SEQUENCE: 53
cgtggtgatc gcgtcctt                                                    18

<210> SEQ ID NO 54
<211> LENGTH: 18
<212> TYPE: DNA
<213> ORGANISM: Artificial Sequence
<220> FEATURE:
<223> OTHER INFORMATION: synthetic construct

<400> SEQUENCE: 54
accagccagc tgagccta                                                    18

<210> SEQ ID NO 55
<211> LENGTH: 18
<212> TYPE: DNA
<213> ORGANISM: Artificial Sequence
<220> FEATURE:
<223> OTHER INFORMATION: synthetic construct

<400> SEQUENCE: 55

```
aaggaccgca tcaccacg                                                 18

<210> SEQ ID NO 56
<211> LENGTH: 36
<212> TYPE: DNA
<213> ORGANISM: Artificial Sequence
<220> FEATURE:
<223> OTHER INFORMATION: synthetic construct

<400> SEQUENCE: 56
accactggat gcaaagctac gtttcgatgg tgtcct                             36

<210> SEQ ID NO 57
<211> LENGTH: 36
<212> TYPE: DNA
<213> ORGANISM: Artificial Sequence
<220> FEATURE:
<223> OTHER INFORMATION: synthetic construct

<400> SEQUENCE: 57
tggtgaccta cgtttcgatg caaagctacc acagga                             36

<210> SEQ ID NO 58
<211> LENGTH: 45
<212> TYPE: DNA
<213> ORGANISM: Artificial Sequence
<220> FEATURE:
<223> OTHER INFORMATION: synthetic construct

<400> SEQUENCE: 58
accactggat gcaaagctac gtttcgatgg tgtcctaggc gagca                   45

<210> SEQ ID NO 59
<211> LENGTH: 45
<212> TYPE: DNA
<213> ORGANISM: Artificial Sequence
<220> FEATURE:
<223> OTHER INFORMATION: synthetic construct

<400> SEQUENCE: 59
tggtgaccta cgtttcgatg caaagctacc acaggatccg ctcgt                   45
```

…

FLUORESCENCE-BASED COMPUTATION SYSTEM

CROSS-REFERENCE TO RELATED APPLICATIONS

This Application claims the benefit of both U.S. Provisional Application No. 62/313,205 filed on Mar. 25, 2016 and U.S. patent application Ser. No. 15/468,767 filed on Mar. 24, 2017, the entirety of each of which is incorporated herein by reference.

STATEMENT REGARDING PRIOR DISCLOSURES BY THE INVENTORS

Two prior disclosures relevant to this application were made by the joint inventors: (1) Massey et al., "Time-Gated DNA Photonic Wires with Förster Resonance Energy Transfer Cascades Initiated by a Luminescent Terbium Donor" *ACS Photonics* 2015, 2, 639-652; and (2) Massey et al., "Time-Resolved Nucleic Acid Hybridization Beacons Utilizing Unimolecular and Toehold-Mediated Strand Displacement Designs" *Anal. Chem.* 2015, 87, 11923-11931.

BACKGROUND

This invention relates to a method for detecting an analyte in a sample by time-resolved fluorescence. In particular, the invention relates to time-resolved fluorescence assays of biological materials based on time-gated DNA photonic wires, time-gated nucleic acid beacons, and time-gated DNA photonic logic operators.

BRIEF SUMMARY

In one embodiment, a photonic wire includes a first nucleic acid chain comprising a long-lifetime FRET donor with an emission lifetime of at least one millisecond, configured as a donor in a first FRET process; a second nucleic acid chain complementary to the first nucleic acid chain and paired thereto, comprising a first fluorescent dye configured as a FRET acceptor in the first FRET process and as a FRET donor in a second FRET process, wherein the paired first and second nucleic acids position the long-lifetime FRET donor and first fluorescent dye at a sweet spot distance from one another in the range of about 0.25 to 1.0 times their predicted Förster distance; and a third nucleic acid chain, also complementary to the first nucleic acid chain and paired thereto adjacent to the second nucleic acid chain, comprising a second fluorescent dye configured as a FRET acceptor in the second FRET process, wherein each of the fluorescent dyes has an emission lifetime of less than 100 nanoseconds.

In another embodiment, nucleic acid hybridization probe includes a probe oligonucleotide having a length of from 15 to 21 nucleic acids; a long-lifetime luminophore with an emission lifetime of at least one millisecond covalently attached to one end of the probe oligonucleotide, the luminophore being configured as a donor in a FRET process; and a fluorescent dye with an emission lifetime of less than 100 nanoseconds configured as an acceptor in the FRET process and covalently attached to an opposite end of the oligonucleotide.

In further embodiments, the nucleic acid hybridization probe further includes a blocker oligonucleotide complementary to and paired to said probe oligonucleotide while having four to six fewer nucleic acids, with a region of complementarity located at the end of the probe having the long-lifetime luminophore exposing a toehold region on the probe (thus exposing a toehold area on the probe), wherein the blocker comprises a quencher configured to quench fluorescence emission of the a long-lifetime luminophore.

Yet another embodiment is a system for computing logical operations including a first oligonucleotide covalently attached to a long-lifetime luminophore with an emission lifetime of at least one millisecond and configured as a donor in a FRET process; at least a second oligonucleotide complementary to the first oligonucleotide; at least one fluorescent dye with an emission lifetime of less than 100 nanoseconds configured as an acceptor in the FRET process covalently attached to one of the oligonucleotides; and, optionally, at least one quencher of fluorescence configured as a quencher of the FRET process covalently attached to one of the oligonucleotides, wherein the system is configured so that an input condition corresponding to the presence or absence of either of one or two oligonucleotide targets complementary to one of the oligonucleotides but distinct from both (in other words, neither of the previously-recited oligos serves as a target) results in an output condition based on the presence or absence of a FRET process between the a long-lifetime luminophore and the fluorescent dye.

BRIEF DESCRIPTION OF THE DRAWINGS

FIG. 1A shows the design of the Temp36 photonic wire, including the nucleotide sequences of the template and complementary segment strands; two arrangements of fluorescent dyes, (i) and (ii); and a model of the photonic wire in (ii). FIG. 1B shows the design of the Temp45 photonic wire, including the nucleotide sequences of the template and complementary segment strands; two arrangements of fluorescent dyes, (i) and (ii); and a model of the photonic wire in (ii). Boldface Arabic numbers are used to denote segment strands and Pn labels denote dye positions. FIG. 1C shows the normalized absorption (dashed lines) and emission spectra (solid lines) for the Tb and dyes used in this study. Spectral overlap functions for each donor with its potential acceptors are also shown (shaded curves). The spectral overlap functions are scaled relative to one another and color-coded by the acceptor dye. The scale bar (A594 panel) represents a magnitude of $3.5\times10^{-11}$ cm$^5$ mol$^{-1}$ and applies to all of the main panels. The insets show spectral overlap functions for a given donor on a magnified scale.

FIG. 3A shows schemata and time-gated emission spectra (32 µs lag-time; 350 µs integration time) for Temp36-(Tb) hybridized with (i) 1-(3'A488) and 1-(5'A488) to place dyes at positions P0 and P9; (ii) 2-(3'A546) and 2-(5'A546) to place dyes at positions P9 and P18; and (iii) 3-(3'A594) and 3-(5'A594) to place dyes at positions P18 and P27. Arrows indicate the approximate position of the dye emission maximum. The color of the spectra match the color of the Pn labels. FIG. 3B shows optimization of dye position for time-gated dye emission. (i) Schemata for configurations with an A546 acceptor at positions P0, P9, P13, P18, and P22 along Temp36-(Tb). The colors of the Pn labels match the corresponding (ii) time-gated emission spectra (32 µs lag-time; 350 µs integration time) and (iii) Tb PL decay curves for the configurations. The inset in panel (ii) shows the time-gated emission spectra with the Tb contribution subtracted. FIG. 3C shows an experiment analogous to that in FIG. 3B with a dark quencher rather than a fluorescent dye. (i) Schemata for configurations with an IabFQ acceptor at positions P0, P9, and P18 along Temp45-(Tb). The Pn labels match the corresponding (ii) Tb PL decay curves.

FIG. 7A shows schematic, prompt and time-gated excitation spectra for A647 during the reverse stepwise assembly of the Tb/A488-initiated photonic wire depicted in FIG. 1B(i). The time-gated settings were 40 µs lag time and 350 µs integration time. FIG. 7B shows schematic and changes in the prompt and time-gated emission intensities of A488 and A594 with the addition of excess 1=2-(5'A488) or 3-(5'A594) strands to the full Tb/A488-initiated photonic wire configuration. The lag times and integration times were 40 µs and 350 µs, and 600 µs and 500 µs, respectively, for the A488 and A594 measurements FIG. 7C shows schematic, prompt and time-gated emission spectra for stepwise assembly of the Tb/A488-initiated photonic wire in the presence of 50% bovine serum. The excitation wavelength was 355 nm. The time-gated settings were 32 µs lag time and 350 µs integration time. The inset shows the time-gated spectra without the Tb emission.

FIGS. 13A, 13B, and 13C illustrate a multiplexed toehold beacon assay. (A) Schematic of the multiplexed assay for two targets. (B) Time-gated fluorescence signals from each reporter dye in panel A for the indicated concentrations of the two targets in a mixture. (C) Average of each reporter dye signal for all data points at the indicated concentration of target, regardless of the amount of the other target. The data demonstrates independent detection of both targets.

FIG. 18 shows truth tables for AND, OR, NAND and NOR logical operators.

FIG. 19 is a truth table and schematics for the AND-I logical operator.

FIG. 25 shows truth table and schematics for the AND-II logical operator.

FIG. 27 shows a truth table and schematics for the OR-I logical operator.

FIG. 29 shows a truth table and schematics for the OR-II logical operator.

DETAILED DESCRIPTION

Definitions

Figure 2A:
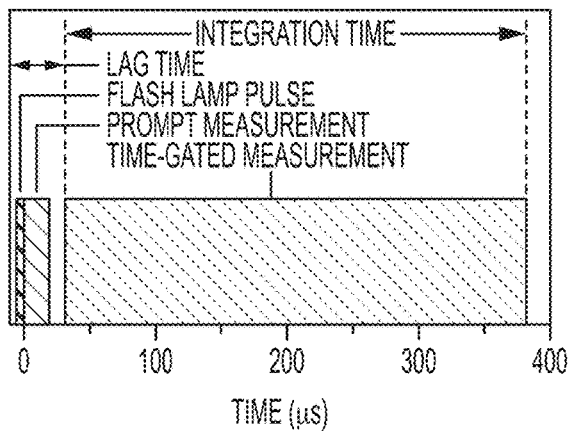
FIG. 2A is a schematic illustration of prompt and time-gated measurements, showing the pulse of light from the xenon flash lamp and signal acquisition windows, defined by the lag time and integration time, for both modes.

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used herein, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

As used herein, unless the context indicates otherwise, a value for a luminescence lifetime (alternately known as an excited state lifetime) refers to that lifetime when the luminophore is a configuration not subject to quenching nor a FRET process.

As used herein, the term "nucleic acid" encompasses both naturally occurring and nucleic acids and synthetic analogs thereof, for example locked nucleic acids.

Overview

Chapter 1 focuses on the development of time-gated DNA photonic wires. Results include the characterization of time-gated FRET and its advantages with the photonic wire configuration, as well as elucidation of a "sweet-spot" for optimum time-gated energy transfer that balances opposing technical and physical considerations.

Chapter 2 focuses on the development of time-gated DNA probes or "beacons" for the detection of target nucleic acid sequences. Results include demonstration of the sensitive, selective and multiplexed detection of target DNA using two different probe configurations in both simple and complex matrices, and characterization of the use of the "sweet spot" for signaling in fluorescent assays.

Chapter 3 is a summary of work in progress toward the design of photonic DNA-based logical operators that combine two physical binary inputs into one binary photonic output.

The procedures, various alternative embodiments, and examples described herein are given for the purposes of example and illustration only and should not be considered or construed as limiting the spirit or scope of the invention. Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way.

Thus, for example, any material with suitable emission lines and luminescence lifetimes on the order of 10 microseconds or more may be used as an FRET donor, these potential FRET donors include but are not limited to chemical compounds, which may be metal coordination complexes, comprising metal ions, metal cations, lanthanide ions, europium ions, terbium ions, terbium(III) ion, possibly in combination with organic phosphors.

Furthermore, various FRET acceptors may be used, for example, comprising fluorescent and non-fluorescent dyes, fluorescent proteins, metal complexes, metal nanoparticles, semiconductor nanoparticles, semiconducting polymer nanoparticles, alloy or oxide nanoparticles, carbon nanomaterials, or any of the former as a constituent of a host material.

Furthermore, various beacon designs may be imagined, for example, a beacon may comprise a stem-loop structure, or a beacon may not comprise a stem-loop structure.

Furthermore, the distance of the "sweet-spot" may be, for example, in the range of $0.25R_0$ to $R_0$, wherein $R_0$ is the Förster distance (typically a range between 1-20 nm, 1-15 nm, 2-12 nm, or 3-8 nm), and the "sweet spot" may be approached from the left or from the right, meaning from a value lower or higher than the "sweet spot". Numeric ranges are inclusive of the numbers defining the range.

Furthermore, various biological materials may be imaged, for example, comprising various conjugates, DNA, RNA, conjugates of DNA, conjugates of RNA, oligonucleotides, single nucleotides, proteins, polypeptides, peptides, and single amino acids.

Chapter 1: Time-Gated DNA Photonic Wires with Förster Resonance Energy Transfer Cascades Initiated by a Luminescent Terbium Donor 1.1 SUMMARY Functional DNA nanotechnology is a rapidly growing area of research with many prospective photonic applications, including roles as wires and switches, logic operators, and smart biological probes and delivery vectors. Photonic wire constructs are one such example and comprise a Förster resonance energy transfer (FRET) cascade between fluorescent dyes arranged periodically along a DNA scaffold. To date, the majority of research on photonic wires has focused on setting new benchmarks for efficient energy transfer over more steps and across longer distances, using almost exclusively organic fluorescent dyes and strictly DNA structures. Here, we expand the range of materials utilized with DNA photonic wires by demonstrating the use of a luminescent terbium complex (Tb) as an initial donor for a four-step FRET cascade along a ~15 nm long DNA/locked nucleic acid (LNA) photonic wire. The inclusion of LNA nucleotides increases the thermal stability of the photonic wires while the Tb affords time-gated emission measurements and other optical benefits. Time-gating minimizes unwanted background emission, whether from direct excitation of fluorescent dyes along the length of the photonic wire, from excess dye-labeled DNA strands in the sample, or from a biological sample matrix. Observed efficiencies for Tb-to-dye energy transfer are also closer to the predicted values than those for dye-to-dye energy transfer, and the Tb can be used as an initial FRET donor for a variety of next-in-line acceptors at different spectral positions. We show that the key to using the Tb as an effective initial donor is to optimally position the next-in-line acceptor dye in a so-called "sweet spot" where the FRET efficiency is sufficiently high for practicality, but not so high as to suppress time-gated emission by shortening the Tb emission lifetime to within the instrument lag or delay time necessary for measurements. Overall, the initiation of a time-gated FRET cascade with a Tb donor is a very promising strategy for the design, characterization, and application of DNA-based photonic wires and other functional DNA nanostructures.

1.2 BACKGROUND

DNA represents an exciting and promising approach to the bottom-up assembly of nanoscale devices for applications such as light harvesting, optical computing, and biological probes.[1-4] As a building block, DNA is advantageous because of its availability, versatility, and programmability. Long lengths of DNA can be obtained from natural sources, then amplified and modified enzymatically, whereas oligonucleotides can be made by solid-phase chemical synthesis or obtained from commercial vendors with terminal or internal modifications such as functional linkers and fluorescent dyes. Complementary DNA sequences predictably and spontaneously hybridize into relatively rigid double helical structures (persistence length ~50 nm), and the rise of the helix (~0.34 nm per base pair) affords sub-nanometer control over length.[1, 4-5] Many years of research on DNA assembly has led to creation of a toolbox with concepts such as DNA origami and DNA tiles that enable the sequence-directed construction of complex, multidimensional structures based on the Watson-Crick double-helix.[6-10] When decorated with optically active materials such as fluorescent dyes or metal nanoparticles, such DNA nanostructures can serve as scaffolds for optical devices and circuits that range in complexity from one-dimensional wires to two-dimensional "motherboards" or "peg-boards," to more complex 3-dimensional photonic architectures.[3, 11-16] Many recent reviews have highlighted DNA nanotechnology and its prospective applications.[2, 6, 9, 11, 17-24]

An important thrust of DNA nanotechnology research has been the development of DNA-based photonic wires and switches that operate via Förster resonance energy transfer (FRET) cascades.[3-4, 24] In these configurations, double-stranded DNA is used as a template to organize a linear array of fluorophores to accept a photon input at one terminus and emit a photon output at the opposite terminus.[1] Excitonic energy is transferred non-radiatively along the length of the wire through a series of n FRET steps, typically between n+1 different fluorophores ordered from shortest to longest wavelengths of absorbance and emission. For example, early work by Kawahara et al. demonstrated 2-step energy transfer along a DNA wire over ~8 nm.[25] Subsequent work by Ohya et al.[26] and Heilemann et al.[27-28] demonstrated 3-step and 4-step energy transfer over distances of ~10 nm and ~13 nm, respectively. More recently, Spillman et al. demonstrated a DNA photonic wire with 6-step energy transfer over >16 nm.[29] Dynamic DNA structures or "switches" that can interrupt or redirect the flow of energy have also been developed by combining multi-step FRET with toe-hold mediated strand invasion.[30] As a potential mechanism for the transmission of information, FRET is advantageous in that it is not diffraction-limited, occurring through-space over nanometer distances, typically on the timescale of nanoseconds or less. However, current DNA-organized FRET-based photonic wires are often non-ideal in that they suffer from photobleaching of the constituent dyes, undesirable direct excitation of dyes downstream from the initial dye in the wire, relative orientations of dyes that are neither optimal nor randomized, lower than predicted transfer efficiencies, and sensitivity to partially formed structures in ensemble measurements.[27, 29, 31] Despite these challenges, the combination of DNA templates, fluorescent dyes and FRET remains one of the most tractable and promising approaches for designing photonic architectures. One strategy to address the limitations associated with fluorescent dyes is the utilization of alternative materials, which, to date, has largely focused on using semiconductor quantum dots (QDs) as both initial input fluorophores and central scaffolds for integrating multiple photonic wires.[32-33] QDs can potentially confer greater resistance to photobleaching, increase the efficiency and flexibility of photonic input through their spectrally broad and strong absorption, and improve the first energy transfer step through their unique characteristics as FRET donors.[34] To date, most other photoluminescent materials remain largely unexplored in photonic wire configurations.

Here, we expand the range of materials utilized in DNA-based photonic wires by utilizing a luminescent terbium complex as the initial donor for a multi-step FRET cascade along a mixed DNA/LNA wire. It is believed that previously, only single-step FRET with terbium complexes has been studied with DNA structures.[35] Luminescent lanthanide complexes are interesting optical materials because of their multiple, narrow emission lines, unpolarized emission, and luminescence lifetimes on the order of microseconds to milliseconds.[36-37] Lanthanide complexes have also been reported to have greater photostability than fluorescent dyes.[38-39] Homogeneous time-resolved fluorescence assays have long taken advantage of the extended luminescence lifetimes of terbium(III) and europium(III) complexes to reject short-lifetime background fluorescence from measurements and eliminate the need for washing steps to remove excess detection reagents.[40-41] More recent work has demonstrated high levels of multiplexing by pairing different FRET acceptors with the various emission lines of terbium (III) complexes.[42-43] In the context of photonic wires, the unique emission properties of luminescent lanthanide complexes can address some of the limitations of configurations that rely exclusively on conventional organic fluorophores. Using a brightly luminescent terbium(III) cryptate (abbreviated Tb) developed by Raymond's group,[44] we show that a luminescent lanthanide complex can enable time-gated, four-step FRET cascades over DNA photonic wires ~15 nm in length. The goal was not to set a new benchmark for the FRET cascade between conventional organic dyes, but rather to evaluate the utility of an initial Tb donor. The versatility of the multiple emission lines of the Tb is demonstrated by initiating the FRET cascade at two different spectral positions, and the time-gating enables minimization of unwanted background emission from direct excitation of non-initial dyes, from excess dye-labeled DNA strands, or from the sample matrix itself. Another important result is the identification of a "sweet spot" for initiating a time-gated FRET cascade along the photonic wire. This sweet spot represents an optimum balance between either excessive or deficient FRET efficiencies for time-gated measurements with good signal-to-background ratios. The incorporation of locked nucleic acid (LNA) residues into our DNA photonic wire has the primary benefit of increasing thermal stability. Overall, we find that the Tb-initiated DNA/LNA photonic wire is an advantageous and highly promising strategy for the design, characterization, and application of DNA nanostructures such as photonic wires.

1.3 EXPERIMENTAL

Materials. Dye-labeled and unlabeled DNA oligonucleotides were from Integrated DNA Technologies (Coralville, Iowa). DNA/LNA template oligonucleotides were from Exiqon (Woburn, Mass.). Lumi4-Tb-NHS was from Lumiphore (Berkeley, Calif.). Modified oligonucleotides were HPLC purified by the manufacturer and used as received. Sequences and modifications are shown in FIGS. 1A-B and listed Table 1.2. Buffer salts were from Sigma-Aldrich (Oakville, ON). All buffers were filter-sterilized prior to use.

Labeling DNA with Tb.

DNA/LNA oligonucleotide template (45.9-65.4 nmol) was dissolved in 250 µL of borate buffer (100 mM, pH 8.5) and 100 µL of DMSO was added. Lumi4-Tb-NHS (0.95-1.14 µmol) was dissolved in 150 µL DMSO and then added to the DNA/LNA oligonucleotide solution (a final ratio of 1:1 buffer:DMSO). After mixing at room temperature for 14 h, the reaction was diluted with 4 mL of buffer. Oligonucleotide and unreacted Lumi4-Tb-NHS were extracted onto Amberchrom CG300M resin, eluted with 70% v/v acetonitrile (aq), and dried in a vacuum centrifuge. The residue was then dissolved in 0.2 M triethylamine-acetate buffer (TEAA; pH 7), and the oligonucleotide purified from excess Lumi4-Tb by gel filtration chromatography with Bio Gel P4 media (Bio-Rad, Mississauga, ON). The eluent was concentrated in a vacuum centrifuge, then further purified with a NAP-10 column (GE Health Care, Baie-d'Urfe, QC) using 0.2 M TEAA buffer as the eluent. UV-visible spectrophotometry was used to confirm a Lumi4-Tb:oligonucleotide labeling ratio of ~1:1 and to quantify the amount of product, which was concentrated to dryness and stored at −20° C. until needed.

Hybridization of the Photonic Wire.

DNA/LNA and DNA oligonucleotides (i.e., template and complementary segments) were mixed at 1 µM each in g-borate saline (TB S) hybridization buffer (90 mM tris-borate, 137 mM NaCl, 2.7 mM KCl, pH 7.6), heated to 95° C. for 5 min, then cooled slowly to room temperature. In experiments where dye-labeled oligonucleotides were omitted, unlabeled oligonucleotide segments were used so that the full length of the template was always double-stranded.

Emission Measurements.

Absorption, excitation, and emission spectra were acquired using a Tecan Infinite M1000 Pro multifunction fluorescence plate reader (Tecan Ltd., Morrisville, N.C.) using 96-well plates. This instrument utilizes monochromators to select the excitation and emission wavelengths and can vary the lag and integration time (between 0-2000 µs and 20-2000 µs, respectively). The excitation wavelength was 355 nm for measurement of prompt and time-gated emission spectra. Lag times were varied depending on the intensity of the prompt background (longer lag times were used for more intense prompt emission) and integration times were varied to maximize signal-to-noise ratios. Typical lag times were between 30-50 µs, although some experiments utilized lag times on the order of hundreds of microseconds. In each case, the lag time was found empirically as the minimum time needed to suppress background from prompt dye fluorescence to negligible levels. Integration times were typically hundreds of microseconds (the maximum 2000 µs lag times did not necessarily provide the best signal-to-noise ratios). Specific values for these parameters in a given experiment are indicated in the text or figure captions. The M1000 was also used for measurements of Tb emission decays using a modification of the boxcar method[45].

Data Analysis.

The time-gated emission intensities from each individual dye were determined by spectral decomposition. The base Tb spectrum was scaled using the sample emission intensity between 470-490 nm, which originated exclusively from the Tb, and subtracted to yield the dye-only time-gated emission spectra. The peak emission intensities from each dye were determined from their peak emission wavelengths with crosstalk corrections for the emission tails of preceding dyes in the FRET cascade series.

1.4 RESULTS

Photonic Wire Configurations and Fluorescent Dyes.

Photonic wires were assembled using long Tb-labeled DNA/LNA template strands in combination with two series of shorter, dye-labeled DNA strands that were complementary to segments of the template strand. A 36 nucleotide (nt) template sequence, denoted Temp36 (SEQ ID No: 12), and a 45 nt template sequence, Temp45 (SEQ ID No: 13), were used in the experiments. Temp45 was analogous to Temp36 except for an additional 9 nt appended at the 3' end of the sequence. Each template was obtained with an aminoalkyl linker at its 5' terminus for labeling with Tb. FIGS. 1A-B illustrate the design of the Temp36 and Temp45 sequences and their complementary DNA segment strands. Each complementary DNA segment strand was 9 nt in length, and these strands aligned end-to-end along the template strands. Temp36 thus had four complementary segments and Temp45 had five complementary segments (the first two of which were combined into a single 18 nt complement). The segments are numbered 1 through 5 and were labeled at either their 3' or 5' terminus with a fluorescent dye (combined segments are indicated with an arrow; e.g., 1⇒3 is a 27-mer combining segments 1, 2 and 3). The sequence of each segment along the template included a central block of 3 nt, of which 2-3 DNA bases were replaced by LNA bases, and two flanking blocks of 3 nt that included two G/C bases and terminal A/T bases (see FIGS. 1A-B). The goal of incorporating LNA bases into Temp36 and Temp45 was to stabilize the duplexes formed between the templates and their complementary segment strands, thereby stabilizing the photonic wire structure. Apparent melt temperatures were ≥4° C. higher for Temp45 containing LNA bases than those without (see Section 1.8, FIG. 1.A2). Neglecting the flexibility of the linkers between the DNA backbone and a fluorescent dye label, and using canonical double-stranded B-DNA as a structural model, the fluorescent dye labels on two adjacent DNA segments were hypothetically positioned ca. 3.2-3.3 nm apart.

The fluorescent dyes used in this work were Alexa Fluor 488 (A488), Alexa Fluor 546 (A546), Alexa Fluor 594 (A594), Alexa Fluor 647 (A647), and Cyanine 5.5 (Cy5.5). Pertinent photophysical properties of these dyes are listed in Table 1.1, and absorption and emission spectra for each dye are shown in FIG. 1C with the corresponding spectral overlap functions for each FRET pair in this study. Förster distances for the FRET pairs are also listed in Table 1.1 and were calculated with the assumption that the dipole orientation factor for energy transfer ($\kappa^2$) is equal to 2/3. For this assumption to hold, fast isotropic motions of the dyes are required.[46] In the photonic wire configurations, the fluorescent dyes are located at the positions shown in FIGS. 1A-B. These positions are referred to as Pn, where n represents the number of nucleotides between the attachment position of the Tb and the attachment position of the dye (e.g., P9 refers to a separation of 9 nt between the Tb and the dye). It should be noted that, with the exception of the termini of a template sequence, dyes can be located in a given position by labeling either the 5' terminus of one complementary segment or the 3' position of the adjacent complementary segment. In the full photonic wire configurations, the ca. 3.2-3.3 nm separation between nearest-neighbor dyes is predicted to yield FRET efficiencies >95%. When necessary for experiments, different dye-dye or Tb-dye combinations were isolated by using unlabeled template or unlabeled complementary segment strands, thereby maintaining consistent double-stranded structure along the entire length of the DNA photonic wire. In the following sections, photonic wire configurations and their components will often be referenced using the template abbreviations, numbered segments, dye abbreviations, and Pn dye positions.

Figure 2B:
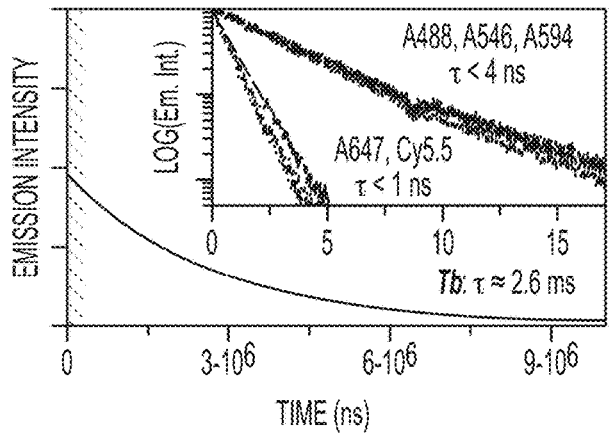
FIG. 2B shows time-resolved emission decay curves for the Tb (main panel; calculated from experimental data) and fluorescent dyes (inset; experimental data). The time-gated acquisition window is shown in the main panel (blue shaded region) for reference. The prompt window is not visible on this scale.
Figure 2C:
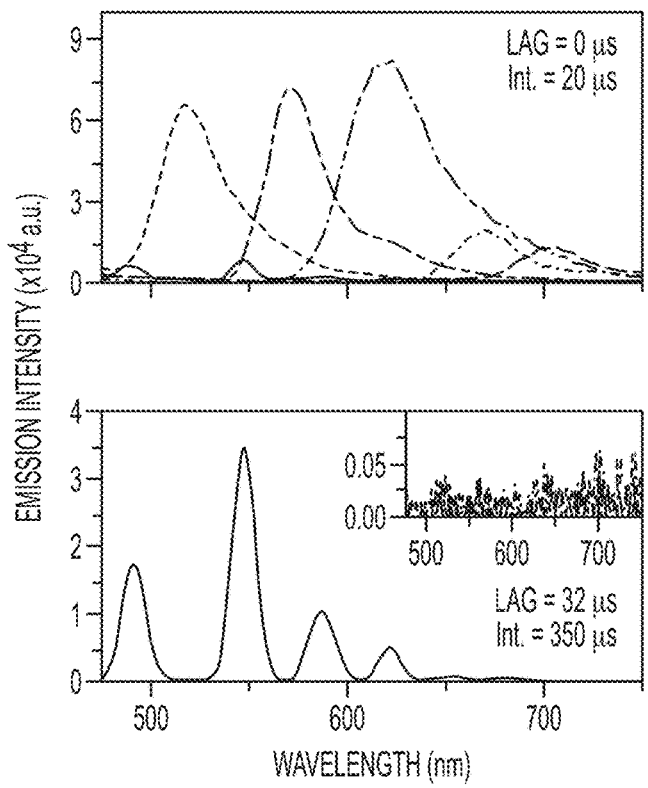
FIG. 2C shows how prompt measurements are sensitive to directly excited dye fluorescence (top), whereas time-gated measurements are sensitive to Tb emission and reject directly excited dye fluorescence (bottom). The inset shows a close up of the time-gated dye emission (i.e., baseline noise).
Figure 2C:
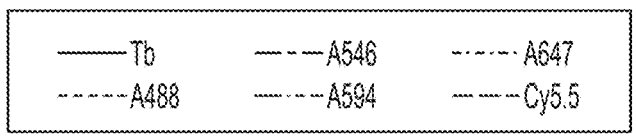

Another important feature of the current photonic wire design is the mismatch between the ~2.6 ms emission lifetime of the Tb[47] and the <4 ns lifetimes of the fluorescent dyes. It is the extraordinarily long lifetime of the Tb that permits time-gated measurements, the concept of which is illustrated in FIG. 2A. A pulse of light from a xenon flash lamp excites the sample and emission is measured after a defined delay or lag time, for a duration defined by the integration time, where both quantities are on the order of tens to hundreds of microseconds. FIG. 2B shows the time-resolved emission decays for the Tb and fluorescent dyes, with the precise lifetimes listed in Table 1.1. FIG. 2C illustrates the effect of time-gating. Prompt, directly-excited emission from the dyes in the photonic wire (defined here as being measured with a 0 μs lag-time and a 20 μs integration time) is much more intense than the Tb emission, even when excited at 355 nm, which is not an optimal wavelength for maximum excitation of the dyes (see FIG. 1C). The Tb emission is weak because its emission is spread over milliseconds. With time-gating (32 μs lag-time) and a longer integration time (350 μs integration time), the Tb emission is measured with much improved signal-to-noise, and the directly excited dye emission decreases to background levels. The prompt measurement captures an estimated 0.7% of the total native Tb emission (i.e., unquenched by FRET) whereas the above time-gated measurement captures ~12% of the total emission. It should be noted that the 32 μs lag time is needed to allow not only the prompt emission to reach background levels, but also to allow the flash lamp afterglow and residual detector signal from the intense prompt emission to subside.[48] The prompt measurement captures ~100% of the native dye emission (i.e., not FRET-sensitized) and the time-gated measurement captures ~0%.

TABLE 1.1

Photophysical properties of the fluorescent dyes used in this study.

| Dye | $\lambda_{max,abs.}$[a] (nm) | $\varepsilon (\lambda_{max,abs.})$[b] ($M^{-1} cm^{-1}$) | $\lambda_{max,em.}$[c] (nm) | $\Phi$[d] | $\tau_0$[e] (ns) | $R_0$ (nm)[f] | | | | |
|---|---|---|---|---|---|---|---|---|---|---|
| | | | | | | A488 | A546 | A594 | A647 | Cy5.5 |
| Tb | 340 | 26 000 | 492, 545 | 0.77 | 2.6 × 10⁶ | 4.8 | 5.5 | 5.4 | 5.4 | 5.1 |
| A488 | 496 | 73 000 | 519 | 0.92 | 3.1 | — | 5.5 | 5.2 | 4.8 | — |
| A546 | 556 | 112 000 | 573 | 0.79 | 3.6 | — | — | 6.0 | 6.1 | 5.7 |
| A594 | 590 | 92 000 | 617 | 0.66 | 3.5 | — | — | — | 6.9 | 6.6 |

TABLE 1.1-continued

Photophysical properties of the fluorescent dyes used in this study.

| Dye | $\lambda_{max,abs.}{}^a$ (nm) | $\varepsilon\ (\lambda_{max,abs.})^b$ ($M^{-1}\ cm^{-1}$) | $\lambda_{max,em.}{}^c$ (nm) | $\Phi^d$ | $\tau_0{}^e$ (ns) | $R_0$ (nm)$^f$ | | | | |
|---|---|---|---|---|---|---|---|---|---|---|
| | | | | | | A488 | A546 | A594 | A647 | Cy5.5 |
| A647 | 650 | 270 000 | 665 | 0.33 | 0.74 | — | — | — | — | 6.5 |
| Cy5.5 | 673 | 209 000 | 707 | 0.30 | 0.92 | — | — | — | — | — |

$^a$Wavelength of absorption maximum (for Tb, this value corresponds to the Lumi4 ligand);
$^b$molar absorption coefficient at $\lambda_{max,abs.}$;
$^c$wavelength of emission maximum (only the two most important peaks are listed for Tb);
$^d$dye quantum yield (reported by the manufacturer); for Tb, this value corresponds to the $Tb^{3+}$ ion;
$^e$emission lifetime;
$^f$calculated Forster distance for the donor-acceptor pair indicated.

Optimal Position of the Initial Dye.

To enhance time-gated sensitization of the dye-to-dye FRET cascade along the photonic wire, our first inclination was to maximize the FRET efficiency between the initial Tb donor and the first fluorescent dye in the series by minimizing their separation distance. To this end, Temp36-(Tb) (see FIG. 1A) was hybridized with segment 1-(3'A488) so as to place the dye at position P0, or segment 1-(5'A488) so as to place the dye at position P9, where all other segment strands were unlabeled. As shown FIG. 3A(i), both of these configurations quenched the time-gated Tb emission intensity by >80%. No detectable time-gated A488 emission was observed from 1-(3'A488), and only a miniscule amount was observed from 1-(5'A488), which placed the dye at position P9. FIG. 1.3A(ii) shows that segment 2-(3'A546), which also placed the dye at position P9, quenched the time-gated Tb emission by ~70% but still yielded only a small amount of time-gated A546 emission. In contrast, 2-(5'A546) and 3-(3'A594), which placed dyes at position P18, yielded intense time-gated dye emission, as shown in FIG. 1.3A(ii, iii). At the subsequent P27 position along Temp36-(Tb), segment 3-(5'A594) also yielded significant time-gated dye emission, as shown in FIG. 1.3A(iii). Apparent quenching of the time-gated Tb emission was notably less (≤10%) in the configurations with significant time-gated dye emission.

Given the foregoing data, and the absence of any anomalous quenching of the prompt A488 and A546 emission when located at positions P0 and P9, we hypothesized that FRET was too efficient for time-gated measurements when acceptor dyes were located at these positions. As the FRET efficiency, E, increases, the Tb donor emission lifetime is expected to decrease according to eqn. 1, where $\tau_{DA}$ and $\tau_D$ are the Tb lifetimes in the presence and absence of dye acceptor.[46]

$$E=1-(\tau_{DA}/\tau_D) \quad (1)$$

The Tb is reported to have an unquenched lifetime of ~2.6 ms[47] and, according to eqn. 1, a FRET efficiency greater than 95% would reduce the Tb lifetime to less than 100 μs. Under these conditions, a majority of the Tb emission would then occur within the measurement lag time rather than the integration time. Since the emission lifetimes of the dyes were less than 4 ns, the Tb lifetime determines the timescale of FRET-sensitized, time-gated dye emission. Acceptor dye emission within the lag-time rather than the integration time is consistent with the negligible time-gated emission from 1-(3'A488) (dye at P0) and minimal time-gated emission from 1-(5'A488) and 2-(3'A546) (dye at P9), as observed in FIG. 1.3. Consideration of the integration time and lag time with respect to eqn. 1 also provides an explanation for the minimal quenching of the Tb emission in configurations with significant FRET-sensitized dye emission (vide infra).

To test the above hypothesis, a set of configurations were prepared where A546 was moved along Temp36-(Tb) from position P0 stepwise through to position P22, using the complementary segment strands 1⇒2-(3'A546), 2⇒3-(3'A546), 1.5-(5'A546), 1⇒2-(5A546) and 1⇒2.5-(5'A546), as shown in FIG. 3B(i). The half-segment numbers refer to sequences that were extended by less than a 9 nt unit (see Table 1.2 for sequences). Combining the segments as single dye-labeled complementary strands of at least 14 nt simplified the experiment and increased duplex stability. Unlabeled segments were used to complete the double-stranded structure along Temp36-(Tb). The time-gated A546 emission (32 μs lag, 350 μs integration time), shown in FIG. 1.3B(ii), scaled as P13>P18>P22>>P9>P0. In contrast, quenching of the Tb emission scaled as P0>P9>>all other positions, consistent with the hypothesis that very efficient FRET can shift sensitized A546 emission to shorter times that are outside of the measurement window.

To directly confirm significant shortening of the Tb lifetime with FRET, the PL decay of Tb was measured for each configuration in FIG. 3B(i). As shown in FIG. 1.3B(iii), the Tb had a lifetime of ~2.7 ms in the absence of A546, consistent with previous measurements.[47] With 1⇒2.5-(5'A546) at P22 and 1⇒2-(5'A546) at P18, the Tb lifetime decreased to ~1.7 ms and ~1.2 ms, respectively, and retained monoexponential character. Interestingly, for 1.5-(5'A546) at P13, the Tb PL decay had biexponential character with a ~380 μs component (73%) and a residual 2.7 ms component (27%). As the A546 was moved closer to the Tb with 2⇒3-(3'A546) at P9 and 1⇒2-(3'A546) at P0, the strongly quenched Tb emission returned to an apparent monoexponential decay with lifetimes >2 ms. The strong quenching of the Tb is hidden within the first few microseconds of the decay curve and the time-gate. This result is consistent with previous observations of quenching of Tb PL via FRET with a residual native Tb lifetime component.[42-43, 47, 49-50]

For FRET associated with 1⇒2-(5'A546) at P18 and 1⇒2.5-(5'A546) at P22, the faster decay of the Tb in FIG. 1.3B(ii) was such that a greater percentage of the total Tb PL was within the integration time. For the unquenched Tb, the lag time and integration time combination measured ~12% of the total Tb PL, whereas ~18% and ~24% of Tb PL were measured for A546 at P22 and P18, respectively. Some of the FRET-induced quenching of the Tb was thus offset, and the measured Tb PL intensities for A546 at P18 and P22 were expected to be within 10% of the Tb alone, as observed experimentally. For 1.5-(5'A546), ~30% quenching of Tb PL was expected to be observed in time-gated measurements, albeit that this quenching was convoluted with residual unquenched Tb PL and some overlap with A546 emission in FIG. 1.3B(ii).

To ensure the generality of the above results, a similar experiment was done with Iowa Black FQ (IabFQ), a dark quencher, instead of A546, where the Förster distance for the Tb-IabFQ FRET pair was 5.1 nm (cf. 5.5 nm for Tb-A546). As shown in FIG. 1.3C, a similar trend in the Tb lifetime was observed when Temp45-(Tb) was hybridized with 1-(3'IabFQ), 1-(5'IabFQ), and 1⇒2-(5'IabFQ), placing the IabFQ quencher at P0, P9, and P18, respectively. The 1-(3'IabFQ) at P0 had strongly quenched Tb emission with a lifetime (2.9 ms) indistinguishable from the Tb alone (2.9 ms), the 1-(5'IabFQ) at P9 had a biexponential Tb decay with a fast FRET-quenched component (280 µs, 53%) and a residual native component (2.9 ms, 47%), and the 1⇒2-(5'IabFQ) at P18 had a quenched apparent monoexponential Tb decay (2.8 ms). The onset of the biexponential decay at a shorter donor-acceptor distance than with A546 (P9 vs. P13) is consistent with the shorter Förster distance associated with IabFQ.

Lastly, the Tb and A546 emission was measured as a function of lag time (with a fixed 50 µs integration time) for Temp36-(Tb) hybridized with 1-(5'A546), 1⇒2-(5'A546), 1⇒3-(5'A546), and 1⇒4-(5'A546), corresponding to dye positions P9, P18, P27, and P36. The trends in the data (see Section 1.8, FIG. 1.A3) were analogous to the trends in the Tb lifetime data (FIG. 3B), with the important observation that the A546 emission tracked with the Tb emission, as was expected given the million-fold difference in lifetime. Although there was virtually no A546 emission with 1-(5'A546) at P9 after a 50 µs lag time, the prompt A546 emission from 1-(5'A546) was more intense than for the other segments at lag times <30 µs. This result was consistent with efficient FRET-sensitized emission from 1-(5'A546) being convoluted with directly excited prompt 1-(5'A546) emission over the prompt timescale (0 µs lag; 20 µs integration time) of our instrument.

Cumulatively, the above data confirms that highly efficient FRET between Tb and dyes at positions P0 and P9 reduces the Tb emission lifetime to a timescale comparable to the instrument response to prompt emission, thereby preventing resolution of time-gated Tb-sensitized emission from the acceptor dyes. Positioning the first acceptor dye further from the Tb, at position P13 or P18, overcomes this problem. These results will be discussed below in the context of a "sweet spot" for energy transfer.

Assembly of the Time-Gated Photonic Wires.

As shown in FIG. 1B, two different photonic wires were assembled with the initial acceptor dye at position P18. Although position P13 yielded greater FRET, position P18 was utilized in photonic wire experiments to permit use of interchangeable 9 nt oligonucleotide segments. The first of the photonic wires, shown in FIG. 1B(i), features a FRET cascade, Tb→A488→A546→A594→A647, where the arrow indicates the direction of energy transfer. The second of these wires, shown in FIG. 1B(ii), features a FRET cascade from Tb→A546→A594→A647→Cy5.5. These configurations differed only in the selection and positioning of the dye labels, as the same template and segment strand sequences were utilized. For brevity, the configuration in FIG. 1B(i) is referred to as the Tb/A488-initiated wire, and the configuration in FIG. 1B(ii) is referred to as the Tb/A546-initiated wire.

Figure 4:
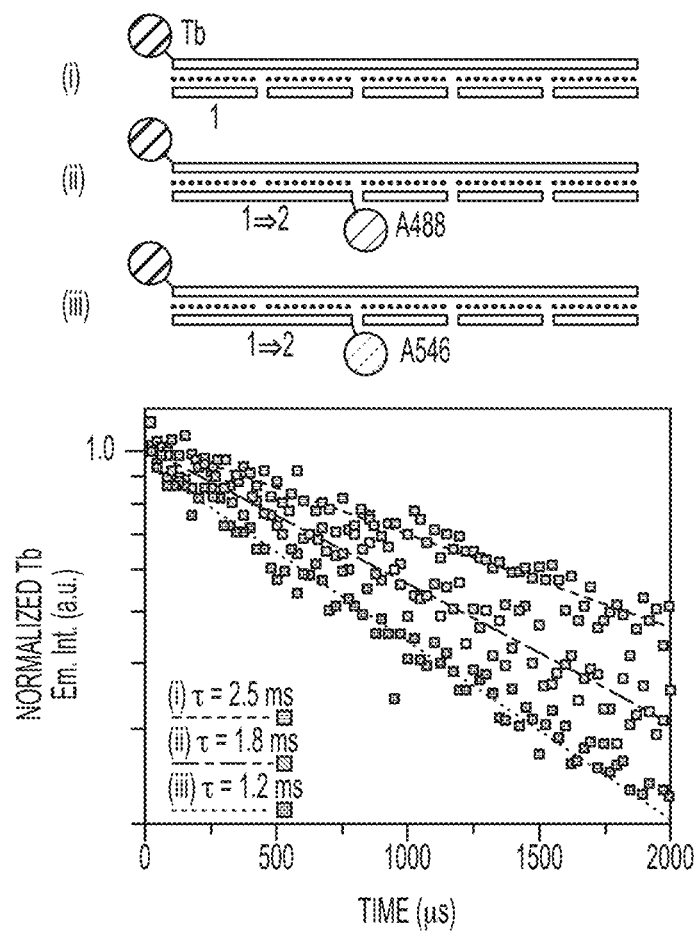
FIG. 4 shows schemata and decay curves for configurations with (i) only Tb, or a single energy transfer step from the Tb to (ii) A488 or (iii) A546 at P18.

The first energy transfer step in the photonic wire is from the Tb to the first fluorescent dye down the length of the template. For the two configurations in FIG. 1.1B, the first dye is either (i) A488 or (ii) A546. To estimate the FRET efficiency from the Tb to the first dye, the change in the decay rate of the Tb was measured. Previous studies have found that quenching of the Tb PL intensity is not necessarily a reliable measure of FRET efficiency because the lag time and integration time do not capture the full decay of the Tb emission, whereas changes in lifetime are reliable.[34, 37, 42-43, 47, 49-50] FIG. 4 shows changes in the Tb emission decay upon the addition of an initial A488 or A546 acceptor, measured using the aforementioned boxcar technique. In this experiment, the Tb emission lifetime was calculated to be ~2.5 ms for the Temp45-(Tb) conjugate, consistent with FIG. 1.3B and the 2.6 ms lifetime previously reported.[47] The Tb lifetime decreased to ~1.8 ms and ~1.2 ms with A488 and A546 acceptors, respectively, corresponding to FRET efficiencies of ~28% and ~52% (calculated via eqn. 1). These FRET efficiencies translate into average donor-acceptor separations of ~5.6 nm and ~5.4 nm, which are in reasonable agreement with the ~6.0 nm separation distance expected from simple geometric considerations for B-DNA (without considering the flexibility of the linkers between the dyes and the oligonucleotides). The larger FRET efficiency of for the Tb-A546 pair arises from the larger spectral overlap integral and longer Förster distance (see Table 1.1).

Figure 5A:
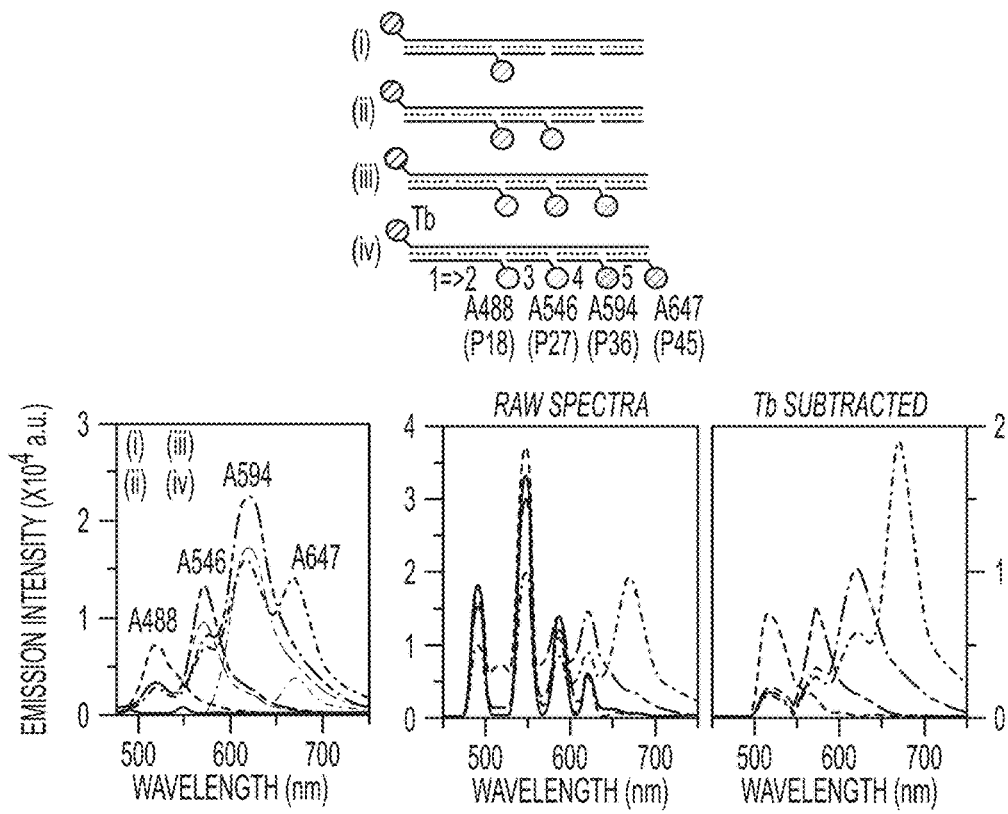
FIG. 5A shows evolution of the FRET-cascade in the Tb/A488-initiated photonic wire depicted in FIG. 1B(i) from left to right: stepwise assembly of the full photonic wire; representative prompt emission spectra (estimated direct excitation components are shown as dashed lines and arise from the UV absorption of the dyes); representative raw time-gated emission spectra, and corresponding Tb-subtracted time-gated emission spectra. The colors of the spectra correspond to the colors of the lowercase Roman numeral labels.
Figure 5B:
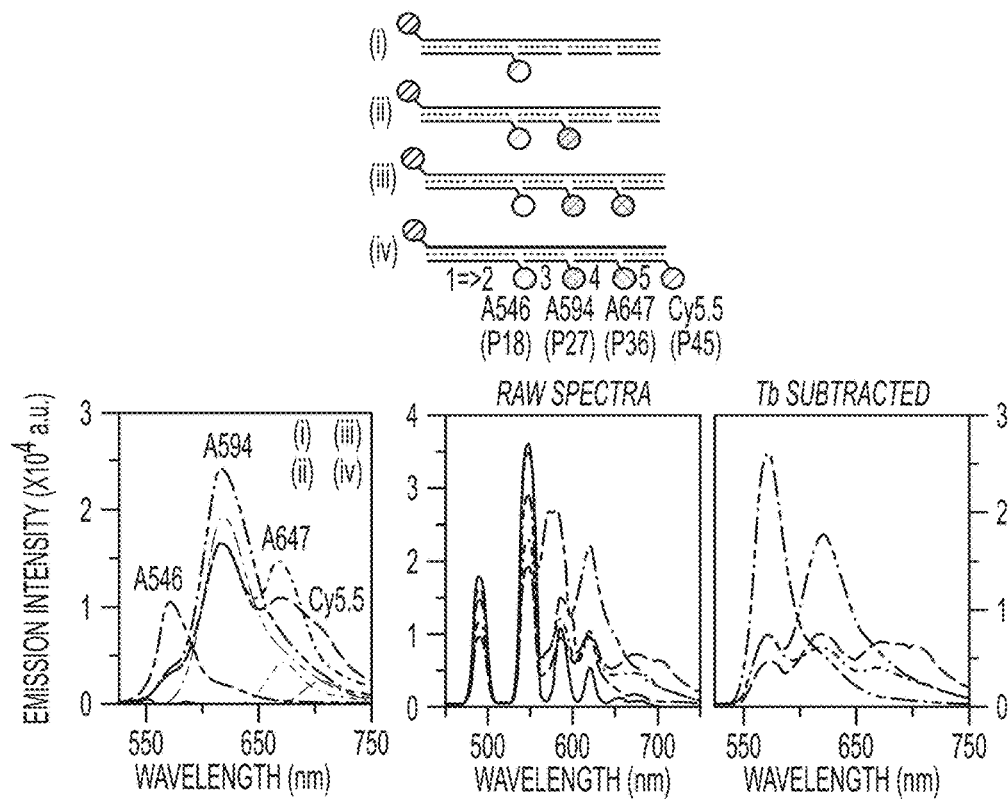
FIG. 5B shows analogous data for the FRET-cascade in the Tb/A546-initiated photonic wire depicted in FIG. 1B(ii). In both cases, the lag time and integration time were 32 µs and 350 µs, respectively, for time-gated measurements. A 20 µs integration time was used for prompt measurements.

FIGS. 5A and B show changes in the prompt (0 µs lag-time, 20 µs integration time) and time-gated emission spectra (32 µs lag-time, 350 µs integration time) with stepwise assembly of both the Tb/A488-initiated and Tb/A546-initiated photonic wire configurations. The prompt spectra show quenching of each $n^{th}$ dye with the addition of the $(n+1)^{th}$ dye along Temp45, and concomitant sensitized emission from the $(n+1)^{th}$ dye. The latter is mixed with directly excited $(n+1)^{th}$ dye emission, estimates of which were obtained from samples with only one dye-labeled segment strand and are also. The time-gated spectra show a similar progression of FRET-induced quenching and sensitization of the $n^{th}$ and $(n+1)^{th}$ dyes, which is more readily apparent when the Tb emission has been subtracted from the overall spectrum. In the case of time-gating, there is no directly excited dye emission (vide infra), and thus the time-gated emission spectra have a different shape than the corresponding prompt spectra (i.e., different magnitudes of emission from each dye). The time-gated spectra are reflective of end-to-end energy transfer along the photonic wire, whereas the prompt spectra represent a composite of energy transfer resulting from energy input at multiple points along the wire.

Figure 6A:
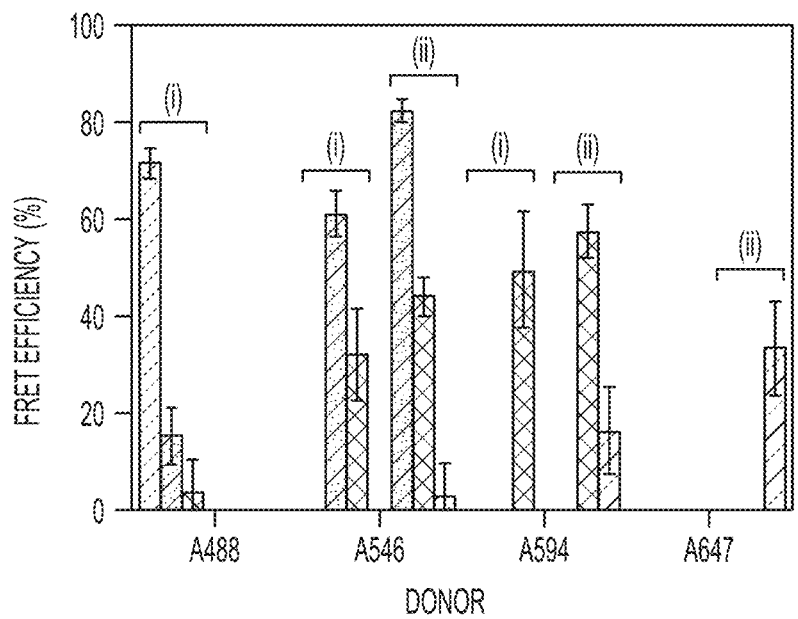
FIG. 6A illustrates efficiencies for time-gated FRET between dyes in the photonic wire configurations. The labels (i) and (ii) indicate the configuration in FIG. 1B. For reference, the Tb→A488 and Tb→A546 FRET efficiencies are 28% and 52%, respectively.
Figure 6B:
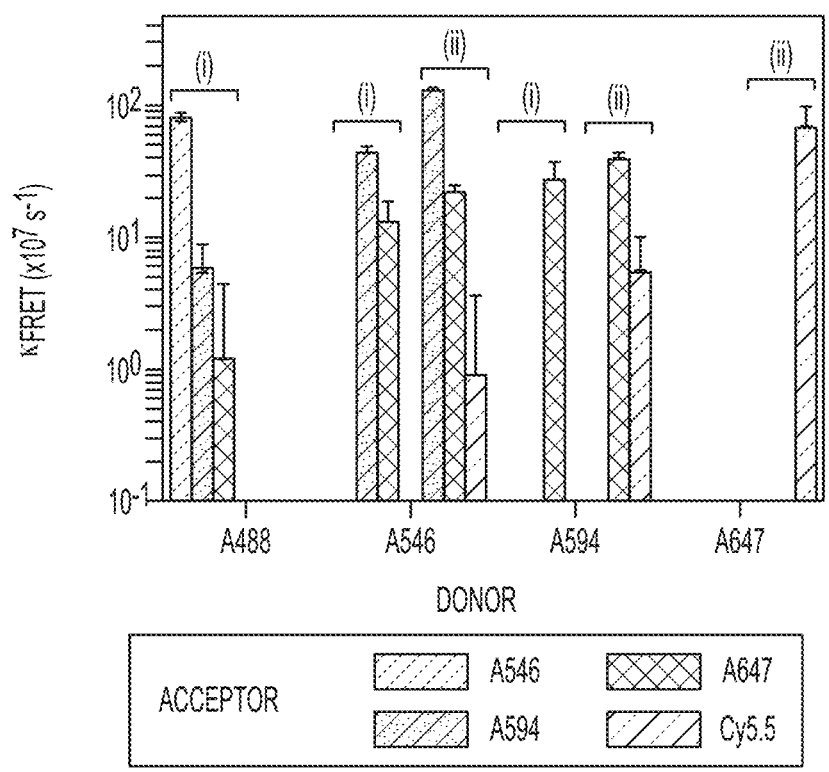
FIG. 6B illustrates rates of FRET between the dyes in the photonic wire configurations. For reference, the Tb→A488 and Tb→A546 FRET rates are 150 s$^{-1}$ and 400 s$^{-1}$, respectively.

To further characterize the photonic wires, time-gated emission spectra were measured, in triplicate, for each permutation of the two configurations. These permutations included 4 variations with one dye, 6 variations with two dyes, 4 variations with three dyes, and the full configuration with four dyes in series. FRET efficiencies between the various dyes were calculated, using Eqn. 2,[46] from the quenching of their time-gated intensities, Ix, when an acceptor (DA) was added to an otherwise analogous configuration (D). The various donor-acceptor efficiencies are plotted in FIG. 6A. Quenching of the time-gated fluorescence intensity of dye donors provides an accurate measure of the FRET efficiency between dyes because their decay occurs within a time period $>10^4$-fold shorter than the integration time. Within the precision of the experiments, the apparent FRET efficiency between the $n^{th}$ and $(n+1)^{th}$ dye were insensitive to the presence or absence of the $(n+2)^{th}$ dye. For example, in the case of the Tb/A488-initiated wire, quenching of A488 by A546 with energy transfer between positions P18 and P27 was not significantly affected by the presence of A594 at position P36. The nearest-neighbor FRET efficiencies ranged from ca. 30-80%, most of which were markedly less than the ~95% quenching efficiency predicted from Förster distances and positioning along the dsDNA helix. The end-to-end FRET efficiency from the dye at P18 to the dye at P45 (~9 nm) was 22±6% for the Tb/A488-initiated wire and 16±5% for the Tb/A546-initiated wire. These values decreased to 6±2% and 8±3%, respectively, when considering energy transfer from the Tb at P0 to the dye at P45 (~15 nm). Rates of FRET, $k_{FRET}$, were calculated from Eqn. 3,[46] and are summarized in FIG. 1.6B. These rates varied from $10^8$-$10^9$ s$^{-1}$ for nearest-neighbor FRET pairs, and $10^7$-$10^8$ s$^{-1}$ for next-nearest-neighbor FRET pairs. For comparison, the calculated rates for the initial Tb→A488 and Tb→A456 energy transfer steps were ca. 150 s$^{-1}$ and 400 s$^{-1}$, respectively, because of the long lifetime of the Tb excited state.

$$E = 1 - (I_{DA}/I_D) \quad (2)$$

$$k_{FRET} = \frac{E}{\tau_0(1-E)} \quad (3)$$

Rejection of Background Signals by Time-Gating.

Unwanted background fluorescence during the measurement of photonic wire emission can arise from multiple sources. One such example is the direct excitation of dyes along the photonic wire that are not the initial donor, resulting in a heterogeneous distribution of FRET cascades initiated at different points along the wire. In addition, directly excited fluorescence from excess dye molecules (i.e., not integrated into a photonic wire structure) may distort or swamp out measured emission spectra. Background fluorescence may also be associated with the medium for the photonic wire. As illustrated in FIGS. 7A-7C, time-gated emission measurements can help ameliorate each of these three potential issues. FIG. 7A shows prompt and time-gated excitation spectra for the terminal A647 acceptor as the Tb/A488-initiated photonic wire is assembled in reverse; that is, starting from the terminal A647 acceptor with the progressive addition of each dye before it in the FRET cascade, with the initial Tb donor present in all cases. The prompt spectra show a progressive convolution of the excitation spectra of each dye, demonstrating the potential initiation of the FRET cascade at multiple points along the photonic wire. In contrast, the time-gated excitation spectra show only the excitation profile of the Tb, which generally increases in magnitude as the wire is assembled in full, consistent with initiation of the time-gated FRET cascade only at the Tb. FIG. 7B shows changes in the prompt and time-gated A488 or A594 emission as 1⇒2-(5'A488) or 3-(5'A594) was mixed with the other components of the Tb/A488-initiated photonic wire (FIG. 1.1B) at ratios of 1:1, 2:1, 4:1 and 8:1. Ideally, a 1:1 ratio corresponds to the stoichiometric assembly of the photonic wire. Over this range of stoichiometry, the prompt A488 and A594 emission increased by close to an order of magnitude; however, the time-gated A488 and A594 emission increased by less than two-fold. Finally, FIG. 1.7C shows the prompt and time-gated emission spectra for the stepwise assembly of the A488-initiated photonic wire in 50% v/v serum. The prompt spectra show the emission of the dyes superimposed on a background of serum autofluorescence that is comparable in magnitude. In contrast, the time-gated spectra have a near-zero background with no detectable autofluorescence from the serum.

1.5 DISCUSSION

Time-Gated FRET "Sweet Spot."

One of the most interesting aspects of this study was finding a "sweet spot" along the photonic wire for time-gated energy transfer between the Tb and the initial dye in the FRET cascade. Specifically, this sweet spot appeared to be between dye positions P9 and P18 in FIG. 1.1. Although other dye positions are in closer proximity to the Tb, the increased FRET efficiency yields a drastic reduction in the Tb lifetime, resulting in sensitized dye emission within the lag time of the instrument used for time-gated measurements. Use of a shorter lag time is precluded by the residual signal from the intense prompt dye emission. Such residual signal is not unique to our fluorescence plate reader, but was also observed with a streak camera system, and has been reported in the literature with other instruments.[48] Conversely, positions further away from the Tb than position P18 yield much smaller amounts of time-gated dye emission because of the distance dependence of FRET. The optimum balance between these two opposing effects can be predicted from Förster theory using eqns. 4 and 5, where D* and A* are the probabilities that the Tb donor and dye acceptor are in an excited state, T is an excited state lifetime, and $\gamma \equiv (R_0/r)^6$ is the Förster coupling. The time-gated dye emission and its dependence on lag time and integration time can be predicted by solving these equations with suitable initial conditions.

$$\frac{dD^*}{dt} = -\frac{D^*}{\tau_D}(1+\gamma) \quad (4)$$

$$\frac{dA^*}{dt} = -\frac{A^*}{\tau_A} + \frac{\gamma D^*}{\tau_D} \quad (5)$$

Figure 8A:
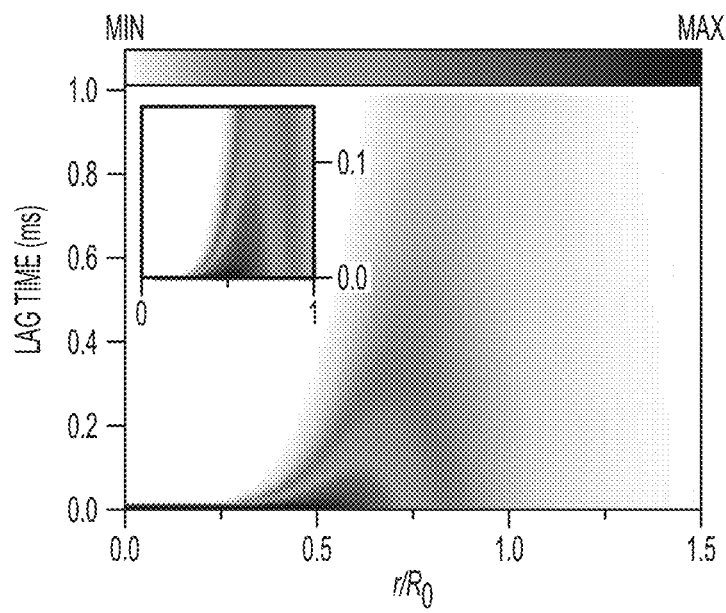
FIG. 8A is a plot of the predicted time-gated A546 emission intensity as a function of lag time and Tb-A546 separation, $r/R_0$, for an integration time of 350 µs. The model clearly predicts a "sweet spot." The inset shows a close up of short lag times and small relative donor-acceptor separations.
Figure 8B:
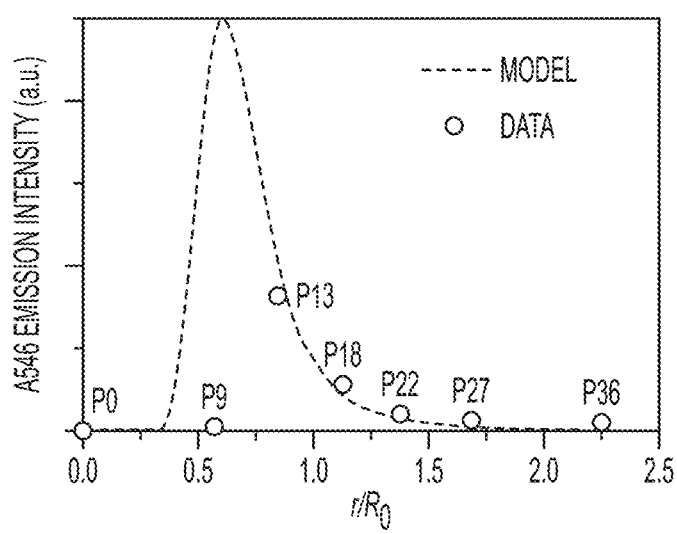
FIG. 8B is a plot of the experimentally measured time-gated A546 emission intensities (points; error bars from three replicate data sets are too small to see). The dashed line shows the prediction from panel A for a lag time of 32 µs (to match the experiment).

FIG. 8A shows the predicted dye emission as a function of lag time and relative donor-acceptor separation, $r/R_0$. The experimental data in FIG. 3B is compared to the prediction in FIG. 8B. The prediction shows good agreement with the data for dye positions P13 through P36 ($r/R_0 > 0.75$), but overestimates the emission observed at shorter distances, specifically position P9 ($r/R_0 \approx 0.6$), which has almost no time-gated emission. The discrepancy in the case of P9 may be because the actual Tb-dye separation is smaller than the nominal ~3.2 nm, perhaps as a result of the linker lengths (~1 nm) and molecular dimensions (~1 nm) allowing the Tb and dye to approach one another more closely or even associate. At such close proximity, there are two prospective FRET pathways that could shift the sensitized dye emission within the instrument lag time. The first of these pathways is the lanthanide-to-dye energy transfer discussed to this point, which would approach 99% efficiency and reduce the Tb lifetime to <30 μs at separations <2.6 nm (a mere 0.6 nm less than the nominal distance). The second of these FRET pathways is direct cryptand-to-dye energy transfer, which would bypass the lanthanide ion and occur within nanoseconds rather than over microseconds or milliseconds. Contributions from this pathway would increase as the Tb-dye separation distance decreases. The balance of the competition between lanthanide-to-dye energy transfer and hypothetical cryptand-to-dye energy transfer is a topic for future research.

More generally, "sweet spots" should be expected in many other time-gated FRET configurations, especially if the lanthanide complexes (or other initial donors) have shorter lifetimes than the Tb(III) cryptate used here. In addition to the idea of a time-gated photonic wire, this concept has important implications for the design of time-resolved assays, biosensors, and diagnostics. The closest possible proximity between donor and acceptor may not maximize time-gated signal, which is counter to typical strategies for maximizing prompt FRET. The "sweet spot" effect, which we have shown to be largely predictable from Förster theory, may have received little attention to date because large lanthanide donor-dye acceptor distances have been unavoidably imposed by proteins in time-resolved assays,[41, 43] and by nanoparticle radii in other recent studies.[42, 51]

Inclusion of LNA Bases.

The photonic wire used to evaluate time-gating with an initial Tb donor was simple in its design. Dye-labeled complementary segments were 9 nt in length to provide close proximity between adjacent dyes in the FRET cascade and still permit a single terminal label per oligonucleotide. LNA was incorporated into the template oligonucleotides as an a priori measure to improve the thermal stability of the short double-stranded hybrid segments, and to help ensure hybridization of complementary segments exclusively at the intended positions along the template. LNA bases restrain the conformational freedom of DNA strands through a methylene bridge between the 2' oxygen and 4' carbon of the ribose ring, resulting in better selectivity against mismatched sequences and tighter binding between complementary sequences ($T_m$ increases by 1-8° C. per LNA nucleotide).[52] To date, LNA and other xeno nucleic acids such as peptide nucleic acid (PNA) have received little attention in the context of DNA nanotechnology, but their structural and functional differences versus DNA (e.g., thermal stability, resistance to enzymatic degradation, degree of tolerance for mismatches)[53-54] could provide important new opportunities. We demonstrated that inclusion of LNA bases in the photonic wire template strand afforded greater thermal stability to the hybrid segments than a DNA-only template (Section 1.8 FIG. 1.A2). Although statistically significant differences in FRET efficiency or acceptor/donor emission ratios were not observed between LNA/DNA and DNA-only templates at room temperature, significant differences were observed at elevated temperature (e.g., physiological temperature; see Section 1.8, FIG. 1.A2). Inclusion of LNA bases in photonic wires is also expected to increase their resistance to nuclease degradation.[55-56] Given our focus on time-gating, more detailed experiments investigating the effect of LNA on formation of the photonic wire were beyond our scope. Nonetheless, the utility of LNA in photonic wires and other DNA nanostructures warrants further investigation in future studies. LNA bases could, for example, allow the formation of photonic wires at lower ionic strength, higher temperatures, or with shorter oligonucleotide segments.

FRET Along the Photonic Wires.

Our results clearly demonstrate that Tb can initiate a FRET cascade between a series of fluorescent dyes. It is surprising, given the Tb-dye separation that corresponds to the "sweet spot," that the efficiency of the initial Tb-to-dye FRET step was not limiting. For the A546-initiated wire, the ~52% Tb→A546 energy transfer efficiency was comparable to the efficiencies for nearest-neighbor A594→A647 FRET, and better than the efficiency for A647→Cy5.5. This efficiency was also better than the next-nearest-neighbor FRET efficiencies between dyes, despite occurring over the same putative donor-acceptor separation. Similarly, for the A488-initiated wire, the ~28% Tb→A488 energy transfer is comparable to that observed for A647→Cy5.5, even though the latter occurs over half the distance. These results suggest that the Tb is relatively well behaved as a FRET donor, whereas the fluorescent dyes underperform in the two FRET cascades. Dye performance less than predicted has been reported in prior studies of photonic wires without time-gating, only some of which can be attributed to incompletely formed structures across an ensemble.[27-29, 32-33] Given that FIG. 1.A2 suggests no large differences in room temperature hybridization efficiency between the 1+2 segment and the 3, 4 or 5 segments, we speculate that the unpolarized emission dipole of the Tb yields more favorable orientation factors for Tb-dye FRET pairs than is possible for dye-dye FRET pairs, which may be constrained in their relative orientations. The general and often unjustified assumption of an orientation factor of $\kappa^2=2/3$ for dynamically random dye orientations may be an overestimate if the fluorescent dyes physically associate with the DNA photonic wire,[57] or have sterically restricted motion. In contrast, the transition dipole of the Tb is random, irrespective of the orientation of the complex itself.

Advantages and Limitations of Tb.

Three important advantages afforded by the initial Tb donor have been demonstrated. First, with a sufficient lag-time, the time-gated emission observed is exclusively the product of energy transfer from the Tb and along the FRET cascade down the photonic wire. In contrast, the prompt dye emission includes both FRET-sensitized and directly excited contributions, such that the prompt measurements will reflect a heterogeneous distribution of FRET cascades initiated at different points along the wire. Although judicious selection of excitation wavelength will change the magnitude of the directly excited emission from each dye, the small Stokes shifts of most dyes, their spectral widths, and the required spectral overlap for efficient FRET will generally preclude exclusive excitation of the initial donor dye in the photonic wire. Although a non-issue for light harvesting applications, direct excitation of multiple dyes is a potential complicating factor for studies of FRET in multidimensional networks and structures, and for biophotonic logic and diagnostic applications. Time-gating avoids these complications. Second, time-gating minimizes the emission signals from fluorescent dyes that are not part of the photonic wire structure. Whereas prompt measurements of emission are overwhelmed by fluorescence from excess dyes, time-gated measurements largely avoid this problem because only dyes in proximity to Tb can sustain emission after the lag time has passed. This feature may be advantageous if assembling complex three-dimensional DNA structures that have modest assembly efficiencies or, more generally, under dilute conditions, where excess strands may help drive nanostructure formation. A third and similar advantage is that background emission from the sample matrix itself can be rejected by time-gating, as demonstrated here by mixing the photonic wires with serum. This capability is highly advantageous for applications in real biological samples because FRET cascades spanning the visible spectrum are typically initiated with blue or violet excitation light, which generates more intense background from sample matrices than longer excitation wavelengths (which afford fewer energy transfer steps). Tb-initiated FRET cascades thus have great promise for prospective biophotonic logic, diagnostic and imaging applications.

Although the advantages afforded by the initial Tb donor are of great value, there are trade-offs associated with its use. The molar absorption coefficient of the Tb is relatively modest compared to many fluorescent dyes and quantum dots, limiting the overall brightness of the photonic wire, albeit compensated by the high quantum yield of the Tb and an improved signal-to-background ratio with time-gated measurements. The multiple emission lines of the Tb permit pairing with many possible dye acceptors but necessitate another level of spectral decomposition to analyze the dye emission, although greatly facilitated by their narrow spectral width. Finally, and similar to previous reports,[51] there is some evidence that Tb can non-specifically associated with some fluorescent dyes. Some limited time-gated emission from all of the dye-labeled DNA strands was observed when mixed with the free Tb complex at sufficiently high concentration (this data is available in the provisional patent application). Such interactions may be responsible for (i) the anomalously high levels of time-gated A647 emission and Tb quenching in the Tb/A488-initiated photonic wire in FIG. 1.5A and FIG. 1.7A, and (ii) the small increases in time-gated A488 and A594 emission in FIG. 1.7B when an 8-fold excess of the corresponding segment strand is added to the template. The precise nature of these putative interactions is beyond our scope here, but may be driven, at least in part, by the mutual hydrophobicity of the Tb and fluorescent dyes. The extent of non-specific association appears to vary with the selection of fluorescent dyes and their accessibility within a DNA nanostructure. For example, the Tb/A546-initiated photonic wire does not show anomalously high levels of emission from the A647 at an internal position (cf. the anomalously high emission when at a terminal position in the Tb/A488-initiated wire). These interactions can likely be avoided by working at sub-micromolar concentrations with carefully selected dyes. Overall, these few drawbacks are quite minor and would be far outweighed by the significant benefits afforded by the Tb and time-gated measurements.

1.6 CONCLUSIONS

We have demonstrated that a luminescent terbium complex (Tb) can be used to initiate a time-gated FRET-cascade along a DNA/LNA photonic wire. The inclusion of the LNA nucleotides increased the thermal stability of the photonic wire structure, and the millisecond-scale emission lifetime of the Tb and its multiple, narrow emission lines provided several additional advantages. The long lifetime permitted time-gated measurements that minimized unwanted background emission from directly excited fluorescent dyes, whether from non-initial positions in the photonic wire or from excess strands. Time-gating also permitted rejection of background from biological sample matrices, and the multiple emission lines permitted initial energy transfer steps to a variety of fluorescent dyes across the visible spectrum. Moreover, observed efficiencies for Tb-to-dye energy transfer were closer to the predicted values than dye-to-dye energy transfer, which are postulated to be a consequence of the unpolarized emission of the Tb resulting in more favorable dipole orientation factors. The key to using the Tb as an effective initial donor was to position the next-in-line acceptor dye in a so-called "sweet spot." When the Tb and its next-in-line acceptor dye were too closely spaced, the high FRET efficiency decreased the Tb donor lifetime to an extent that Tb-sensitized emission shifted into the lag or delay time required for time-gated measurements. Conversely, too far a spacing between the Tb and its acceptor dye resulted in low energy transfer efficiencies and low levels of FRET-sensitized time-gated emission. Optimization of the spacing permitted time-gated emission measurements with high signal-to-background ratios. Overall, initiation of a time-gated FRET cascade with a Tb donor is a very promising strategy for the fundamental design and characterization of photonic wires and other functional DNA nanostructures because it can improve signal-to-background in several ways, as demonstrated here along with the important design consideration of the "sweet spot."

Oligonucleotide Sequences

Figure 9:
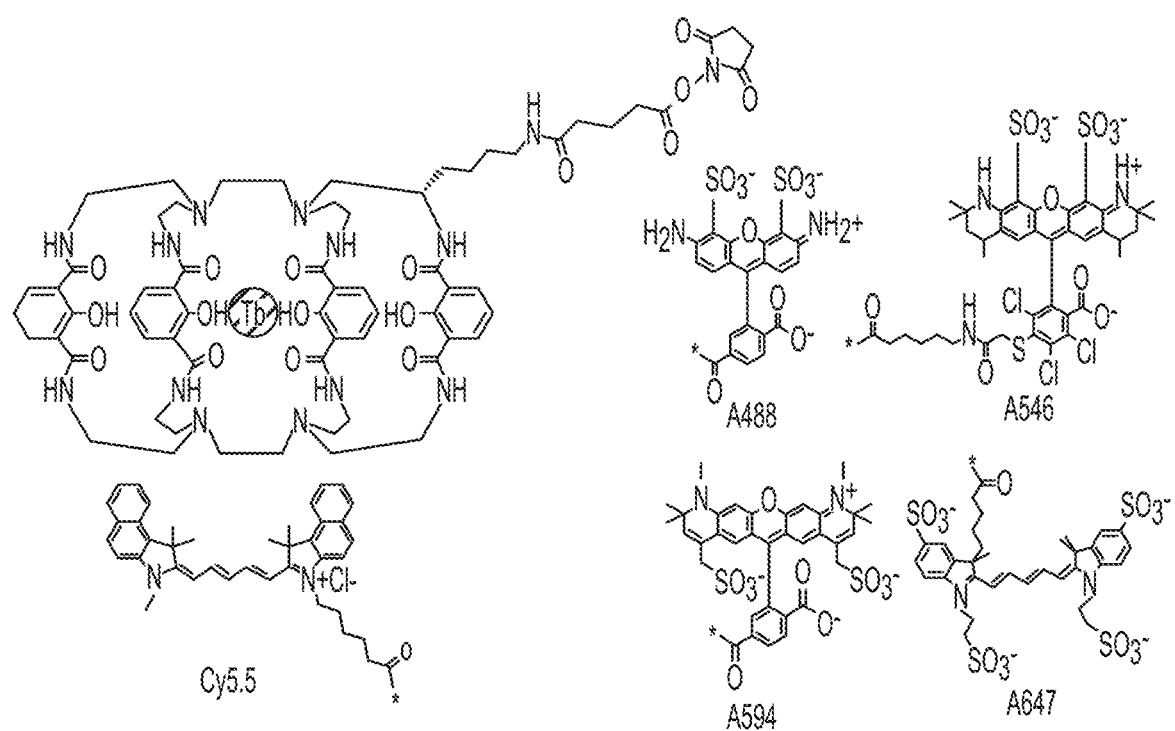
FIG. 9 illustrates the structures of the Tb(III) cryptate (Tb) and the fluorescent dyes used.

The complete set of oligonucleotide sequences and modifications are listed in Table 1.2. Structures of the dyes and Tb are shown in FIG. 9. Dye- and linker-modified oligonucleotides were HPLC purified by the manufacturer (Integrated DNA Technologies, Coralville, Iowa, USA).

1.7 EXEMPLARY MATERIALS

TABLE 1.2

Oligonucleotide sequences and modifications.

| Segment | 5' mod. | Sequence (5'→3') | 3' mod. |
|---|---|---|---|
| 1 | — | TCC AGT GGT | — |
| 1 | A488 | TCC AGT GGT | — |
| 1 | — | TCC AGT GGT | A488 |
| 1 | IabFQ | TCC AGT GGT | — |
| 1 | — | TCC AGT GGT | IabFQ |
| 1 | A546 | TCC AGT GGT | — |
| 1 | — | TCC AGT GGT | A546 |
| 1.5 | A546 | TGC ATC CAG TGG T (SEQ ID NO. 1) | — |
| 2 | — | AGC TTT GCA | — |
| 2 | A546 | AGC TTT GCA | — |
| 2 | — | AGC TTT GCA | A546 |
| 3 | — | TCG AAA CGT | — |
| 3 | A546 | TCG AAA CGT | — |

TABLE 1.2-continued

Oligonucleotide sequences and modifications.

| Segment | 5' mod. | Sequence (5'→3') | 3' mod. |
|---|---|---|---|
| 3 | A594 | TCG AAA CGT | — |
| 3 | — | TCG AAA CGT | A594 |
| 3.5 | — | TCG AAA CGT AGC TT (SEQ ID NO. 2) | — |
| 4 | — | AGG ACA CCA CCA | — |
| 4 | A594 | AGG ACA | — |
| 4 | A647 | AGG ACA CCA | — |
| 4 | — | AGG ACA CCA | A647 |
| 4.5 | — | AGG ACA CCA TCG AA (SEQ ID NO. 3) | — |
| 5 | — | TGC TCG CCT | — |
| 5 | A647 | TGC TCG CCT CCT | — |
| 5 | Cy5.5 | TGC TCG | — |
| 1 ⇒ 2 | A488 | AGC TTT GCA TCC AGT GGT (SEQ ID NO. 4) | — |
| 1 ⇒ 2 | A546 | AGC TTT GCA TCC AGT GGT (SEQ ID NO. 5) | — |
| 1 ⇒ 2 | — | AGC TTT GCA TCC AGT GGT (SEQ ID NO. 6) | A546 |
| 1 ⇒ 2 | IabFQ | AGC TTT GCA TCC AGT GGT (SEQ ID NO.) | — |
| 1 ⇒ 2.5 | A546 | ACG TAG CTT TGC ATC CAG TGG T (SEQ ID NO. 8) | — |
| 2 ⇒ 3 | — | TCG AAA CGT AGC TTT GCA (SEQ ID NO. 9) | A546 |
| 1 ⇒ 3 | A546 | TCG AAA CGT AGC TTT GCA TCC AGT GGT (SEQ ID NO. 10) | — |
| 1 ⇒ 4 | A546 | AGG ACA CCA TCG AAA CGT AGC TTT GCA TCC AGT GGT (SEQ ID. No: 11) | — |

A488 = Alexa Fluor 488; A546 = Alexa Fluor 546; A594 = Alexa Fluor 594; A647 = Alexa Fluor 647; Cy5.5 = Canine 5.5; IabFQ = Iowa Black FQ.

1.8 REFERENCES (1) Garcia-Parajo, M. F.; Hernando, J.; Mosteiro, G. S.; Hoogenboom, J. P.; van Dijk, E.; van Hulst, N. F., Energy Transfer in Single-Molecule Photonic Wires. *Chem. Phys. Chem.* 2005, 6, 819-827.
(2) Pinheiro, A. V.; Han, D. R.; Shih, W. M.; Yan, H., Challenges and Opportunities for Structural DNA Nanotechnology. *Nat. Nanotechnol.* 2011, 6, 763-772.
(3) Teo, Y. N.; Kool, E. T., DNA-Multichromophore Systems. *Chem. Rev.* 2012, 112, 4221-4245.
(4) Tinnefeld, P.; Heilemann, M.; Sauer, M., Design of Molecular Photonic Wires Based on Multistep Electronic Excitation Transfer. *Chem. Phys. Chem.* 2005, 6, 217-222.
(5) Su, W.; Bonnard, V.; Burley, G. A., DNA-Templated Photonic Arrays and Assemblies: Design Principles and Future Opportunities. *Chem. Eur. J.* 2011, 17, 7982-7991.
(6) Nangreave, J.; Han, D. R.; Liu, Y.; Yan, H., DNA Origami: A History and Current Perspective. *Curr. Opin. Chem. Biol.* 2010, 14, 608-615.
(7) Rothemund, P. W. K.; Andersen, E. S., Nanotechnology: The Importance of Being Modular. *Nature* 2012, 485, 584-585.
(8) Seeman, N. C., DNA Nanotechnology: Novel DNA Constructions. *Annu. Rev. Biophys. Biomol. Struct.* 1998, 27, 225-248.
(9) Seeman, N. C., Nanomaterials Based on DNA. *Annu. Rev. Biochem.* 2010, 79, 65-87.
(10) Kuzuya, A.; Komiyama, M., DNA Origami: Fold, Stick, and Beyond. *Nanoscale* 2010, 2, 310-322.
(11) Tan, L. H.; Xing, H.; Lu, Y., DNA as a Powerful Tool for Morphology Control, Spatial Positioning, and Dynamic Assembly of Nanoparticles. *Acc. Chem. Res.* 2014, 47, 1881-1890.
(12) Kuzuya, A.; Ohya, Y., DNA Nanostrutures as Scaffolds for Metal Nanoparticles. *Polymer J.* 2012, 44, 452-460.
(13) Matczyszyn, K.; Olesiak-Banska, J., DNA as Scaffolding for Nanophotonic Structures. *J. Nanophotonics* 2012, 6.
(14) Yu, X.; Lei, D. Y.; Amin, F.; Hartmann, R.; Acuna, G. P.; Guerrero-Martinez, A.; Maier, S. A.; Tinnefeld, P.; Carregal-Romero, S.; Parak, W. J., Distance Control In-Between Plasmonic nanoparticles via Biological and Polymeric Spacers. *Nano Today* 2013, 8, 480-493.
(15) Buckhout-White, S.; Spillmann, C. M.; Algar, W. R.; Khachatrian, A.; Melinger, J. S.; Goldman, E. R.; Ancona, M. G.; Medintz, I. L., Assembling Programmable FRET Based Photonic Networks Using Designer DNA Scaffolds. *Nat. Commun.* 2014, 5, in press.
(16) LaBoda, C.; Duschl, H.; Dwyer, C. L., DNA-Enabled Integrated Molecular Systems for Computation and Sensing. *Acc. Chem. Res.* 2014, 47, 1816-1824.

(17) Jester, S. S.; Famulok, M., Mechanically Interlocked DNA Nanostructures for Functional Devices. *Acc. Chem. Res.* 2014, 47, 1700-1709.

(18) Kuzuya, A.; Ohya, Y., Nanomechanical Molecular Devices made of DNA Origami. *Acc. Chem. Res.* 2014, 47, 1742-1749.

(19) Rangnekar, A.; LaBean, T. H., Building DNA Nanostructures for Molecular Computation, Templated Assembly, and Biological Applications. *Acc. Chem. Res.* 2014, 47, 1778-1788.

(20) Tsukanov, R.; Tomov, T. E.; Liber, M.; Berger, Y.; Nir, E., Developing DNA Nanotechnology Using Single-Molecule Fluorescence. *Acc. Chem. Res.* 2014, 47, 1789-1798.

(21) Wang, Z. G.; Ding, B. Q., Engineering DNA Self-Assemblies as Templates for Functional Nanostructures. *Acc. Chem. Res.* 2014, 47, 1654-1662.

(22) Yang, D. Y.; Hartman, M. R.; Derrien, T. L.; Hamada, S.; An, D.; Yancey, K. G.; Cheng, R.; Ma, M. L.; Luo, D., DNA Materials: Bridging Nanotechnology and Biotechnology. *Acc. Chem. Res.* 2014, 47, 1902-1911.

(23) Sacca, B.; Niemeyer, C. M., DNA Origami: The Art of Folding DNA. *Angew. Chem. Int. Ed.* 2012, 51, 58-66.

(24) Albinsson, B.; Hannestad, J. K.; Borjesson, K., Functionalized DNA Nanostructures for Light Harvesting and Charge Separation. *Coord. Chem. Rev.* 2012, 256, 2399-2413.

(25) Kawahara, S.; Uchimaru, T.; Murata, S., Sequential Multistep Energy Transfer: Enhancement of Efficiency of Long-Range Fluorescence Resonance Energy Transfers. *Chem. Commun.* 1999, 563-564.

(26) Ohya, Y.; Yabuki, K.; Hashimoto, M.; Nakajima, A.; Ouchi, T., Multistep Fluorescence Resonance Energy Transfer in Sequential Chromophore Array Constructed on Oligo-DNA Assemblies. *Bioconjugate Chem.* 2003, 14, 1057-1066.

(27) Heilemann, M.; Kasper, R.; Tinnefeld, P.; Sauer, M., Dissecting and Reducing the Heterogeneity of Excited-State Energy Transport in DNA-Based Photonic Wires. *J. Am. Chem. Soc.* 2006, 128, 16864-16875.

(28) Heilemann, M.; Tinnefeld, P.; Mosteiro, G. S.; Garcia-Parajo, M.; Van Hulst, N. F.; Sauer, M., Multistep Energy Transfer in Single Molecular Photonic Wires. *J. Am. Chem. Soc.* 2004, 126, 6514-6515.

(29) Spillmann, C. M.; Buckhout-White, S.; Oh, E.; Goldman, E. R.; Ancona, M. G.; Medintz, I. L., Extending FRET Cascades on Linear DNA Photonic Wires. *Chem. Commun.* 2014, 50, 7246-7249.

(30) Graugnard, E.; Kellis, D. L.; Bui, H.; Barnes, S.; Kuang, W.; Lee, J.; Hughes, W. L.; Knowlton, W. B.; Yurke, B., DNA-Controlled Excitonic Switches. *Nano Lett.* 2012, 12, 2117-2122.

(31) Sanchez-Mosteiro, G.; van Dijk, E.; Hernando, J.; Heilemann, M.; Tinnefeld, P.; Sauer, M.; Koberlin, F.; Patting, M.; Wahl, M.; Erdmann, R.; van Hulst, N. F.; Garcia-Parajo, M. F., DNA-based Molecular Wires: Multiple Emission Pathways of Individual Constructs. *J. Phys. Chem. B* 2006, 110, 26349-26353.

(32) Boeneman, K.; Prasuhn, D. E.; Blanco-Canosa, J. B.; Dawson, P. E.; Melinger, J. S.; Ancona, M.; Stewart, M. H.; Susumu, K.; Huston, A.; Medintz, I. L., Self-Assembled Quantum Dot-Sensitized Multivalent DNA Photonic Wires. *J. Am. Chem. Soc.* 2010, 132, 18177-18190.

(33) Spillmann, C. M.; Ancona, M. G.; Buckhout-White, S.; Algar, W. R.; Stewart, M. H.; Susumu, K.; Huston, A. L.; Goldman, E. R.; Medintz, I. L., Achieving Effective Terminal Exciton Delivery in Quantum Dot Antenna-Sensitized Multistep DNA Photonic Wires. *ACS Nano* 2013, 7, 7101-7118.

(34) Algar, W. R.; Kim, H.; Medintz, I. L.; Hildebrandt, N., Emerging Non-Traditional Förster Resonance Energy Transfer Configurations with Semiconductor Quantum Dots: Investigations and Applications. *Coord. Chem. Rev.* 2014, 263-264, 65-85.

(35) Selvin, P. R.; Rana, T. M.; Hearst, J. E., Luminescence Resonance Energy Transfer. *J. Am. Chem. Soc.* 1994, 116, 6029-6030.

(36) Armelao, L.; Quici, S.; Barigelletti, F.; Accorsi, G.; Bottaro, G.; Cavazzini, M.; Tondello, E., Design of Luminescent Lanthanide Complexes: From Molecules to Highly Efficient Photo-Emitting Materials. *Coord. Chem. Rev.* 2010, 254, 487-505.

(37) Hildebrandt, N.; Wegner, K. D.; Algar, W. R., Luminescent Terbium Complexes: Superior Förster Resonance Energy Transfer Donors for Flexible and Sensitive Multiplexed Biosensing. *Coord. Chem. Rev.* 2014, 273-274, 125-138.

(38) Bunzli, J. C. G., Lanthanide Luminescent Bioprobes (LLBs). *Chem. Lett.* 2009, 38, 104-109.

(39) Marriott, G.; Heidecker, M.; Diamandis, E. P.; Yanmarriott, Y., Time-resolved Delayed Luminescence Image Microscopy Using an Europium Ion Chelate Complex. *Biophys. J.* 1994, 67, 957-965.

(40) Hemmila, I.; Laitala, V., Progress in Lanthanides as Luminescent Probes. *J. Fluoresc.* 2005, 15, 529-542.

(41) Hagan, A. K.; Zuchner, T., Lanthanide-based Time-Resolved Luminescence Immunoassays. *Anal. Bioanal. Chem.* 2011, 400, 2847-2864.

(42) Geißler, D.; Charbonnière, L. J.; Ziessel, R. F.; Butlin, N. G.; Löhmannsröben, H. G.; Hildebrandt, N., Quantum Dot Biosensors for Ultra-Sensitive Multiplexed Diagnostics. *Angew. Chem. Int. Ed.* 2010, 49, 1396-1401.

(43) Geißler, D.; Stufler, S.; Löhmannsröben, H. G.; Hildebrandt, N., Six-Color Time-Resolved Förster Resonance Energy Transfer for Ultrasensitive Multiplexed Biosensing. *J. Am. Chem. Soc.* 2013, 135, 1102-1109.

(44) Xu, J.; Corneillie, T. M.; Moore, E. G.; Law, G. L.; Butlin, N. G.; Raymond, K. N., Octadentate Cages of Tb(III) 2-Hydroxyisophthalamides: A New Standard for Luminescent Lanthanide Labels. *J. Am. Chem. Soc.* 2011, 133, 19900-19910.

(45) James, D. R.; Siemiarczuk, A.; Ware, W. R., Stroboscopic Optical Boxcar Technique for Determination of Fluorescence Lifetimes. *Rev. Sci. Inst.* 1992, 63, 1710-1716.

(46) Lakowicz, J. R., *Principles of Fluorescence Spectroscopy*. 3rd ed.; Springer Science+Business Media: New York, 2007.

(47) Algar, W. R.; Wegner, D.; Huston, A. L.; Blanco-Canosa, J. B.; Stewart, M. H.; Armstrong, A.; Dawson, P. E.; Hildebrandt, N.; Medintz, I. L., Quantum Dots as Simultaneous Acceptors and Donors in Time-Gated Förster Resonance Energy Transfer Relays: Characterization and Biosensing. *J. Am. Chem. Soc.* 2012, 134, 1876-1891.

(48) Cywiński, P. J.; Hammann, T.; Hühn, D.; Parak, W. J.; Hildebrandt, N.; Löhmannsröben, H. G., Eurpoium-Quantum Dot Nanobioconjugates as Luminescent Probes for Time-Gated Biosensing. *J. Biomed. Opt.* 2014, 19, 101506.

(49) Wegner, K. D.; Morgner, F.; Oh, E.; Goswami, R.; Susumu, K.; Stewart, M. H.;

Medintz, I. L.; Hildebrandt, N., Three-Dimensional Solution-Phase Förster Resonance Energy Transfer Analysis of Nanomolar Quantum Dot Bioconjugates with Subnanometer Resolution. *Chem. Mater.* 2014, 26, 4299-4312.
(50) Wegner, K. D.; Lanh, P. T.; Jennings, T.; Oh, E.; Jain, V.; Fairclough, S. M.; Smith, J. M.; Giovanelli, E.; Lequeux, N.; Pons, T.; Hildebrandt, N., Influence of Luminescence Quantum Yield, Surface Coating, and Functionalization of Quantum Dots on the Sensitivity of Time-Resolved FRET Bioassays. *ACS Appl. Mater. Interfaces* 2013, 5, 2881-2892.
(51) Algar, W. R.; Malanoski, A. P.; Susumu, K.; Stewart, M. H.; Hildebrandt, N.; Medintz, I. L., Multiplexed Tracking of Protease Activity Using a Single Color of Quantum Dot Vector and a Time-Gated Förster Resonance Energy Transfer Relay. *Anal. Chem.* 2012, 84, 10136-10146.
(52) Petersen, M.; Wengel, J., LNA: A Versatile Tool for Therapeutics and Genomics. *Trends Biotechnol.* 2003, 21, 74-81.
(53) Karkare, S.; Bhatnagar, D., Promising Nucleic acid Analogs and Mimics: Characteristic Features and Applications of PNA, LNA, and Morpholino. *Appl. Microbiol. Biotechnol.* 2006, 71, 575-586.
(54) Briones, C.; Moreno, M., Applications of Peptide Nucleic Acids (PNAs) and Locked Nucleic Acids (LNAs) in Biosensor Development. *Anal. Bioanal. Chem.* 2012, 402, 3071-3089.
(55) Wang, L.; Yang, C. J.; Medley, C. D.; Benner, S. A.; Tan, W., Locked Nucleic Acid Molecular Beacons. *J. Am. Chem. Soc.* 2005, 127, 15664-15665.
(56) Wengel, J., Synthesis of 3'-C- and 4'-C-Branched Oligodeoxynucleotides and the Development of Locked Nucleic Acid (LNA). *Acc. Chem. Res.* 1999, 32, 301-310.
(57) Mikheikin, A. L.; Zhuze, A. L.; Zasedatelev, A. S., Binding of Symmetrical Cyanine Dyes into the DNA Minor Groove. *J. Biomol. Struct. Dyn.* 2000, 18, 58-72.

Chapter 2: Time-Gated Nucleic Acid Hybridization Probes

2.1 SUMMARY

Nucleic acid hybridization probes are sought after for numerous assay and imaging applications. These probes are often limited by the properties of fluorescent dyes, prompting the development of new probes where dyes are paired with novel or nontraditional luminescent materials. Luminescent terbium complexes are an example of such a material, and these complexes offer several unique spectroscopic advantages. Here, we demonstrate two nonstem-loop designs for light-up nucleic acid hybridization beacons that utilize time-resolved Förster resonance energy transfer (TR-FRET) between a luminescent Lumi4-Tb cryptate (Tb) donor and a fluorescent reporter dye, where time-resolved emission from the dye provides an analytical signal. Both designs are based on probe oligonucleotides that are labeled at their opposite termini with Tb and a fluorescent reporter dye. In one design, a probe is partially blocked with a quencher dye-labeled oligonucleotide, and target hybridization is signaled through toehold-mediated strand displacement and loss of a competitive FRET pathway. In the other design, the intrinsic folding properties of an unblocked probe are utilized in combination with a temporal mechanism for signaling target hybridization. This temporal mechanism is based on a recently elucidated "sweet spot" for TR-FRET measurements and exploits distance control over FRET efficiencies to shift the Tb lifetime within or outside the time-gated detection window for measurements. Both the blocked and unblocked beacons offer nanomolar (femtomole) detection limits, response times on the order of minutes, multiplexing through the use of different reporter dyes, and detection in complex matrices such as serum and blood. The blocked beacons offer better mismatch selectivity, whereas the unblocked beacons are simpler in design. The temporal mechanism of signaling utilized with the unblocked beacons also plays a significant role with the blocked beacons and represents a new and effective strategy for developing FRET probes for bioassays.

2.2 BACKGROUND

Nucleic acid assays and imaging probes are of widespread interest for biomedical diagnostics, genomics research, environmental monitoring, food and water quality assessment, and many other applications.[1] Targets of interest include specific sequences of genomic DNA, protein-coding mRNA, and regulatory RNA such as microRNA, among others.[2-4] Oligonucleotide probes are almost exclusively used for these assays because of their inherently selective and high-affinity binding to complementary sequences and the widely available chemical synthesis of oligonucleotide probes with modifications such as unnatural bases and backbones, linkers, and fluorescent dyes.[5,6] Fluorescence-based hybridization assays with oligonucleotide probes, including those utilizing Förster resonance energy transfer (FRET),[7,8] are among the most popular assay formats because they offer high sensitivity, multiplexing capability, multimodal detection (e.g., intensity, lifetime, polarization), and measurement-at-a-distance. Nonetheless, these assays have often been limited by the shortcomings of fluorescent dyes, prompting the development of assays with novel or nontraditional luminescent materials such as fluorescent polymers,[9,10] quantum dots,[11,12] metal nanoclusters,[13,14] upconversion nanoparticles[15,16] luminescent lanthanide complexes (LLCs),[17-23] and combinations of these materials.[24,25] These materials can either replace fluorescent dyes or be used in tandem with dyes to enhance assay capabilities.

LLCs offer several advantages as labels for luminescence assays, including spectrally narrow emission lines, large spectral separation between excitation and emission, and excited state lifetimes of hundreds of microseconds up to milliseconds.[26-28] These long lifetimes enable time-gated luminescence measurements with microsecond delays between flash excitation and measurement of emission. Time-gating permits efficient rejection of unwanted background signals, such as scattered excitation light and sample autofluorescence, which typically decay within nanoseconds to microseconds.[26] LLCs, and terbium complexes in particular, also have unique characteristics as donors in time-resolved FRET (TR-FRET) assays.[26,29,30] Their multiple emission lines can sensitize multiple acceptor dyes in multiplexed assays; their unpolarized emission restricts the orientation between 1/3 and 4/3, and time-gated measurements can reject unwanted direct excitation of acceptor fluorescence.[26] As described in several reviews,[26,28,31-33] a wide variety of TR-FRET assays with lanthanide donors have been developed, including commercial assay systems.[34,35] Hybridization assays with LLCs have generally taken the form of conventional stem-loop molecular beacons with dark quenchers,[17,19] proximity assays where separate probe sequences with an LLC donor and fluorescent acceptor dye hybridize adjacent to one another,[20,21,23] or a combination of these two formats.[22]

Recently, we utilized a luminescent terbium cryptate as a donor to sensitize a DNA photonic wire, where the well-defined structure of the DNA permitted elucidation of an optimum efficiency or "sweet spot" for TR-FRET measurements.[36] When the FRET efficiency was very high, the terbium lifetime was shortened to a degree where most of the emission occurred within the delay between flash excitation and measurement. When the efficiency was too low, the small magnitude of the FRET-sensitized acceptor emission was limiting. In both cases, time-gated acceptor emission was weak or not observed. An intermediate efficiency, obtained through control of the donor-acceptor distance via the DNA scaffold, provided sufficiently intense acceptor emission and sufficiently long delay times for effective time-gated measurements. This "sweet spot" is a temporal effect that is unique to the long lifetimes of LLCs and is a potential tool for designing novel FRET assays. Whereas most FRET-based assays with fluorescent acceptors have an off-state with low/negligible energy transfer efficiency, the temporal effect can generate an off-state through high-efficiency energy transfer. This capability potentially adds a new dimension to signal modulation in FRET assays.

Figures 10A, 10B:
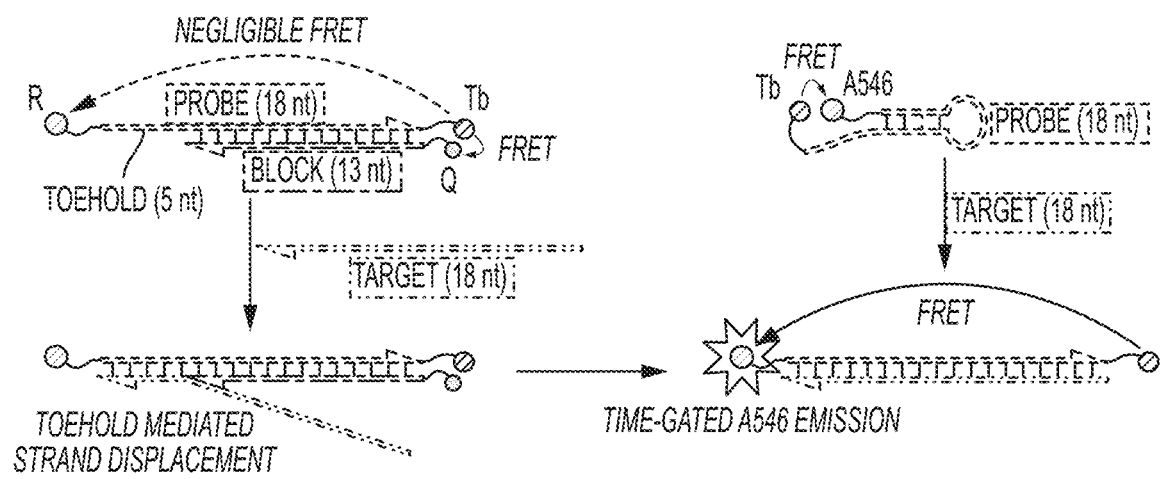
FIGS. 10A and 10B illustrate (A) toehold/blocked time-gated beacon, and (B) unblocked time-gated beacon. Hybridization of target DNA is signaled via time-gated reporter (R) emission, sensitized by energy transfer from the Tb, where R=A488 or A546, and Q is frequently IabFQ, but can also be A488, A546, or Alexa Fluor 594.

Here, we exploit the "sweet spot" temporal effect to develop light-up oligonucleotide beacons for the detection of unlabeled DNA targets. An 18 nucleotide (nt) probe sequence is labeled at its 3' terminus with Lumi4-Tb, a luminescent terbium(III) cryptate (Tb),[37] and labeled at its 5' terminus with a fluorescent reporter dye such as Alexa Fluor 546 (A546) or Alexa Fluor 488 (A488). In one design, shown in FIG. 10A, this probe is hybridized with a 13 nt blocking sequence that is labeled at its 5' terminus with a quencher dye. The quencher may be either a fluorescent dye or a nonfluorescent dye such as Iowa Black FQ (IabFQ). Both the reporter and quencher dyes are FRET acceptors for the Tb donor; however, FRET to the quencher dye dominates because of its close proximity to the Tb, and the high FRET efficiency creates an initial dark state for time-gated measurements. The 5 nt unhybridized region of the probe sequence serves as a toehold for complementary target to bind and displace the blocking sequence, and a significant increase in time-gated reporter dye emission provides an analytical signal. A second functional design, shown in FIG. 10B, is the doubly labeled probe itself. Even without a blocking sequence, an increase in time-gated reporter dye emission signals target hybridization. This signaling is attributed to the formation of an initial folded probe structure that places the Tb and reporter dye in close proximity, with a FRET efficiency sufficiently high to create an initial dark state. We show that both the blocked and unblocked time-gated beacons are capable of quantitative, selective, and multiplexed detection, characterize their signaling mechanisms, and demonstrate their utility with complex sample matrices such as serum and blood. Overall, the properties of the Tb and the unique temporal signaling mechanism endow these beacons with several novel features and a distinct set of analytical advantages.

2.3 EXPERIMENTAL SECTION

Materials and Instruments.

Oligonucleotides were from Integrated DNA Technologies (Coralville, Iowa). If modified with a linker or fluorescent dye, the oligonucleotides were HPLC purified by the manufacturer. Amine-reactive Lumi4-Tb-NHS was from Lumiphore (Berkeley, Calif.). Alexa Fluor dyes were from Life Technologies (Carlsbad, Calif.). Oligonucleotide sequences and modifications are listed in Table 2. Melt temperatures, $T_m$, were calculated using UNAFold.[38, 39] All buffers were filter-sterilized prior to use. Bovine serum was from Sigma-Aldrich (Oakville, ON, Canada), and defibrinated bovine blood was from Hemostat Laboratories (Dixon, Calif.). All emission measurements were made with an Infinite M1000 Pro multifunction plate reader (Tecan US Inc., Morrisville, N.C.) and black, nonbinding 96-well microtiter plates (Corning Inc., Corning, N.Y.). In addition to monochromator-based selection of excitation and emission wavelengths, this instrument was capable of time-gated measurements with control of the lag time (i.e., delay between flash excitation and acquisition of signal) and the detector integration time.

TABLE 2

| name | sequence[a] | $T_m$ (° C.)[b] |
|---|---|---|
| A488-Q513L-Tb Probe | A488-5'-TAG GCT CAG CTG GCT GGT-3'-Tb (SEQ ID NO. 12) | |
| Q513L Block | Q1-5'-ACC AGC CAG CTG A-3' (SEQ ID NO. 13) | 48 |
| Q513L TGT | 5'-ACC AGC CAG CTG AGC CTA-3' (SEQ ID NO. 14) | 60 |
| Q513L 1 bpm | 5'-ACC AGC CAG CTG AGC CAA-3' (SEQ ID NO. 15) | 58 |
| A546-S315T-Tb Probe | A546-5'-CGT GGT GAT CGC GTC CTT-3'-Tb (SEQ ID NO. 16) | |
| S315T Block | Q2-5'-AAG GAC GCG ATC A-3' (SEQ ID NO. 17) | 43 |
| S315T TGT | 5'-AAG GAC GCG ATC ACC ACG-3' (SEQ ID NO. 18) | 58 |
| S315T 2 bpm | 5'-AAG GAC GCG ATC ACC AGC-3' (SEQ ID NO. 19) | 52 |
| NC | 5'-ACT TCC GGT CTC AAT GAA-3' (SEQ ID NO. 20) | |

[a]Tb = Lumi4-Tb cryptate; Q1 = IabFQ, A488, or A594; Q2 = IabFQ, A488, or A546; A488 = Alexa Fluor 488; A546 = Alexa Fluor 546; A594 = Alexa Fluor 594; IabFQ = Iowa Black FQ dark quencher; TGT = target; N bpm = N base pair mismatched target; NC = noncomplementary sequence. Mismatches are indicated in bold.
[b]Calculated melt temperature when hybridized with probe in TBS buffer.

Oligonucleotide Labeling.

Probe oligonucleotides were obtained with 5' thiol linker and 3' amine linker modifications. The 5'-thiol linker was labeled with maleimide-functionalized A488 or A546 dye, and the dye-labeled oligonucleotide was purified by size exclusion chromatography (SEC). The 3'amine linker of the dye-labeled oligonucleotide was subsequently labeled with Lumi4-Tb-NHS, and the dual-labeled oligonucleotide was purified by SEC. A DNA/dye/Tb ratio of ~1:1:1 was verified using UV-visible absorption spectrophotometry. The detailed protocol can be found in the Supporting Information of Massey et al., "Time-Resolved Nucleic Acid Hybridization Beacons Utilizing Unimolecular and Toehold-Mediated Strand Displacement Designs" *Anal. Chem.* 2015, 87, 11923-11931, incorporated herein by reference for the purpose of disclosing oligonucleotide labeling techniques.

Assays.

Except when otherwise indicated, assays were done in tris-borate saline (TBS) buffer (90 mM tris-borate, 137 mM NaCl, 2.7 mM KCl, pH 7.6). For the toehold beacons, block sequences were annealed to probe sequences by mixing the two sequences at a 1:1 ratio, diluting with TBS, and heating to 95° C. with subsequent slow cooling to room temperature. For unblocked beacons, an annealing step was not necessary. The A488-Q513L-Tb and A546-S315T-Tb toehold beacon concentrations in assays were 50 and 25 nM, respectively, unless otherwise noted. Target oligonucleotides were added to the samples at room temperature and allowed to stand for 45-60 min (unless kinetics were measured). Time-gated emission spectra were measured with excitation at 355 nm (20 nm bandwidth) and with emission at 520 nm for A488 and 572 nm for A546 (5 nm bandwidth). For measurement of hybridization kinetics, time-gated emission was measured at 15 or 30 s intervals for 30-45 min. The lag/integration times were 50 μs/500 μs for measurements in buffer. Multiplexed assays were done as described above, where both the A488-Q513L-Tb and A546-S315T-Tb probes were present in the same sample. A546 emission was corrected for crosstalk with A488 emission as described in the previously-cited Supporting Information of Massey et al., "Time-Resolved Nucleic Acid Hybridization Beacons Utilizing Unimolecular and Toehold-Mediated Strand Displacement Designs" Anal. Chem. 2015, 87, 11923-11931, incorporated herein by reference for the purpose of disclosing techniques for this correction. Assays in serum and blood were done using the same procedure with small differences: dilution of probes with TBS was minimized to ensure >90% v/v serum or blood in the final samples, the A488-Q513L-Tb and A546-S315T-Tb concentrations were both 0.25 μM, and the lag time and integration time for time-gated emission measurements were both 2000 μs.

2.4 RESULTS AND DISCUSSION

Donor-Acceptor Pairs.

Figure 11:
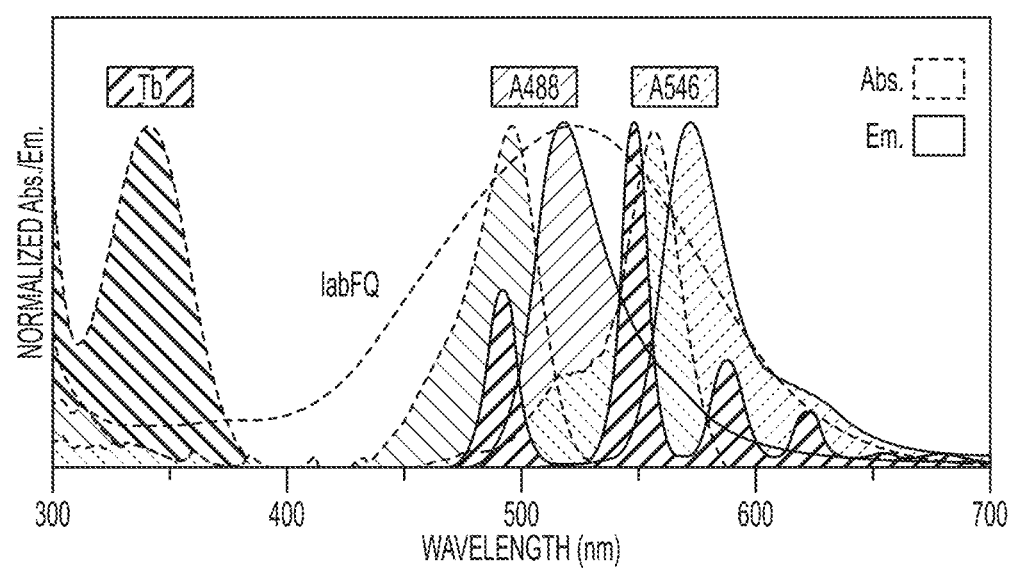
FIG. 11 shows normalized absorption and emission spectra for the Tb and A488, A546, and IabFQ dyes.

The Tb donor is Lumi4-Tb, an octadentate luminescent terbium(III) cryptate originally developed in the Raymond Group.[37] The Tb is paired with A488, A546, and IabFQ as three main acceptor dyes in the study. FIG. 11 shows the normalized absorption and emission spectra for the Tb, A488, A546, and IabFQ. The estimated Förster distances are 5.4 nm for the Tb-A488 pair, 6.2 nm for the Tb-A546 pair, and 5.7 nm for the Tb-IabFQ pair. Additional details and data for these FRET pairs, and a Tb-Alexa Fluor 594 (A594) FRET pair, can be found in the previously cited Supporting Information of Massey et al., "Time-Resolved Nucleic Acid Hybridization Beacons Utilizing Unimolecular and Toehold-Mediated Strand Displacement Designs" Anal. Chem. 2015, 87, 11923-11931.

Toehold (Blocked) Beacon Assays.

Figure 12A:
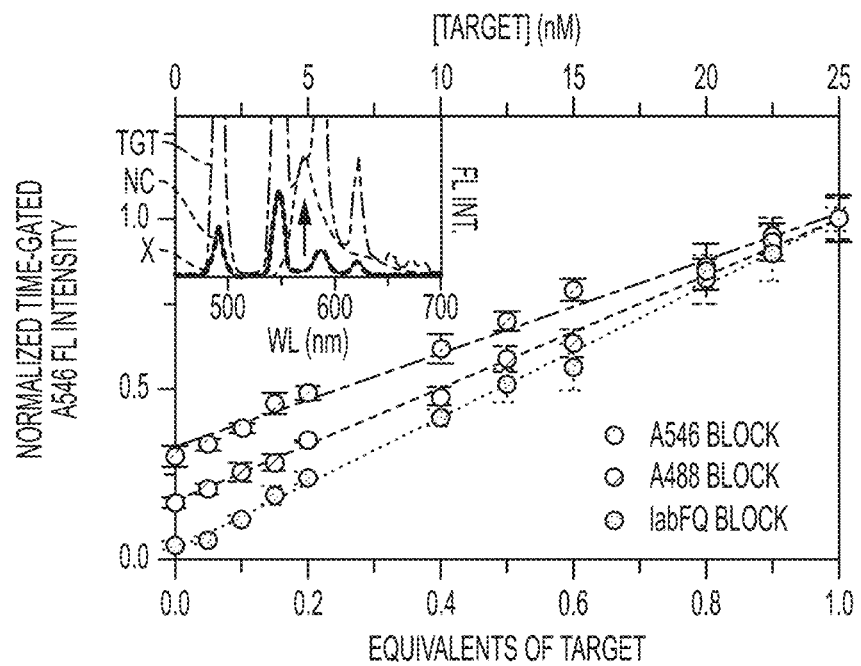
FIGS. 12A and 12B are calibration plots for (A) A546-S315T-Tb and (B) A488-Q513L-Tb toehold beacons with different Q labels on the corresponding blocking sequence. The insets show time-gated spectra for samples with only beacon (X), non-complementary DNA (NC), and complementary target DNA (TGT). There is a large increase in intensity upon hybridization of the beacons with complementary target.
Figure 12B:
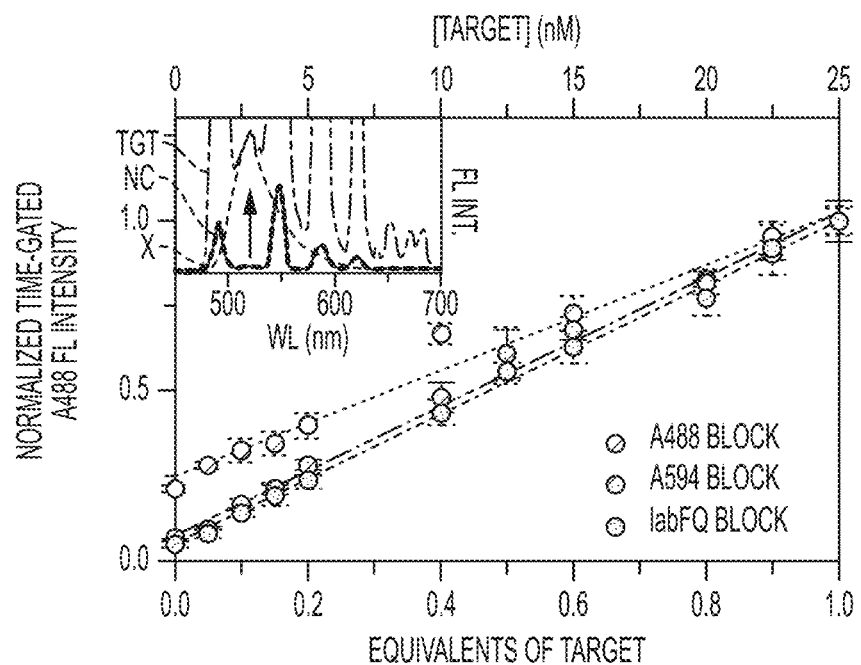

FIG. 12 shows the response of the blocked A488-Q513L-Tb and A546-S315T-Tb toehold beacons to an increasing amount of unlabeled, complementary target DNA. The two probe sequences are complementary to genetic markers for drug-resistant tuberculosis.[40-43] Upon hybridization with target, the time-gated fluorescence intensity of the A488 or A546 reporter dye, measured at the wavelength minima between the three Tb emission lines at 490, 550, and 590 nm, increased between 4.7-21-fold for A488 and 3.6-24-fold for A546 depending on the identity of the quenching dye attached to the blocking sequence. There was no detectable response to non-complementary DNA. FIG. 12 includes calibration curves for block sequences labeled with A488, A546, A594, and IabFQ dyes. In each case, the time-gated acceptor dye fluorescence intensity increased linearly with increasing amounts of target up to one equivalent and was saturated at close to one equivalent. Comparable limits of detection (LOD) were obtained for all three blocking configurations with 25 nM A546-S315T-Tb probe: 1.6 nM (120 fmol), 2.1 nM (160 fmol), and 1.2 nM (90 fmol) for blocking sequences with A488, A546, and IabFQ, respectively. The corresponding LODs for 50 nM A488-Q513L-Tb probe were 4.0 nM (300 fmol), 1.2 nM (90 fmol), and 1.8 nM (135 fmol) for blocking sequences with A488, A594, and IabFQ, respectively. The LOD was defined as three standard deviations above the average blank signal.

The data in FIG. 12 illustrates that there are two synergistic signaling mechanisms for the toehold beacons. First, when the quencher was a dark quencher such as IabFQ, or a fluorescent dye that was different from the reporter dye on the probe strand, the reporter dye emission was quenched by competitive energy transfer to the quencher. That is, the Tb preferentially transferred its energy to the quencher dye rather than the reporter dye, and the time-gated reporter dye fluorescence intensity was diminished. A theoretical calculation suggests that energy transfer to the quencher should exceed 97% efficiency, whereas energy transfer to the reporter would be less than 1%. Second, and regardless of the identity of the quencher dye, the total time-gated emission from the beacon was decreased because the high-efficiency energy transfer shortened the Tb lifetime from its native value of ~2.6 ms to less than ~0.2 ms, such that most of the Tb emission and FRET-sensitized reporter emission was within the instrument lag time rather than the detector integration time. It is for this reason that both the Tb and reporter dye emission increase in the insets of FIG. 12. Moreover, it is because of this temporal effect that A488 and A546 can be simultaneously used as both the reporter and quencher within the same beacon. The sensitivity and LODs of the calibration curves in FIG. 12 were limited by residual background emission from A488 and A546. This background was minimized with a nonfluorescent dark quencher such as IabFQ and with A594, which had emission at wavelengths longer than the A488 reporter. With the A546-S315T-Tb, the A488 was better as a quencher than A546, because it had lower residual emission at the A546 wavelength, but worse than IabFQ because the long-wavelength tail of its emission was still nonzero at the A546 wavelength (see FIG. 11). Thus, although the temporal effect permitted the use of the same fluorescent dye as both reporter and quencher, the lower background achievable with competitive energy transfer to a dark quencher provided the best analytical figures of merit.

Multiplexed Toehold Beacon Assay.

The A488-Q513L-Tb and A546-S315T-Tb probes were orthogonal to one another in nucleotide sequence, potentiating their simultaneous use in the multiplexed assay depicted in FIG. 13A without interference from cross-hybridization. From a detection stand-point, multiplexing was possible because the A488 and A546 fluorescence were mostly resolved from one another and from the Tb emission lines. A two-plex assay was done with a constant mixture of 50 nM (4 pmol) A488-Q513L-Tb and 25 nM (2 pmol) A546-S315T-Tb toehold beacons, both with IabFQ-labeled blocks. Varying amounts of the two DNA targets (final concentrations of 9.5-47.5 nM Q513L target and 4.8-23.8 nM S315T target) were added to the beacons, and the time-gated A488 and A546 fluorescence intensities were measured. The A546 measurement was corrected for 16% crosstalk from the tail of the A488 emission. As shown in FIGS. 13B and 13C, selective and nearly orthogonal detection of each target was possible for every combination of targets tested. The signals measured for one target, in the presence of six different amounts of the other target, were approximately constant and agreed with relative standard deviations for the average signals between 5% and 10%. The toehold beacons thus functioned independently in two-plex assays.

Unblocked Beacon Assays.

Figure 14A:
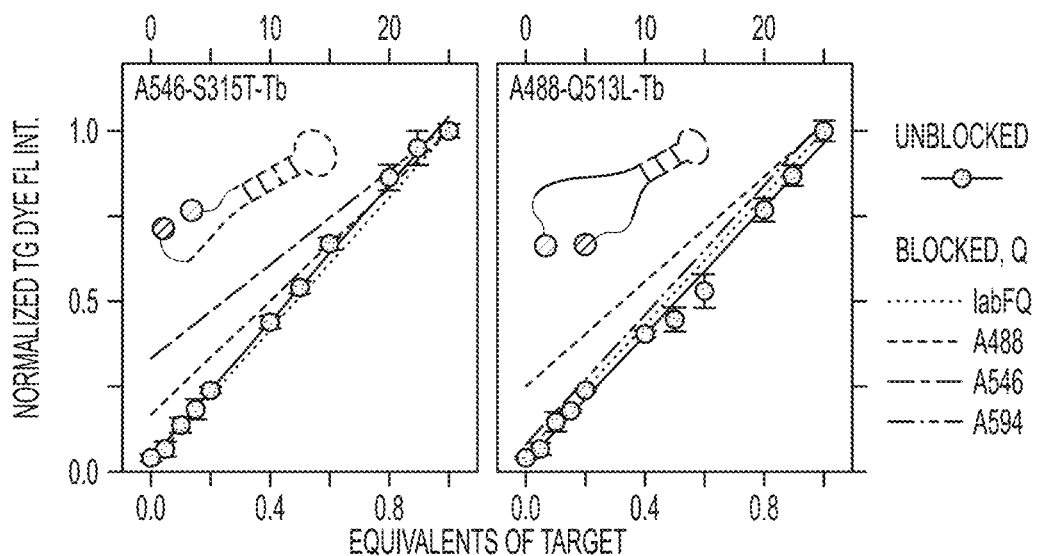
FIGS. 14A and 14B show assays with unblocked beacons. (A) Time-gated reporter dye fluorescence of from beacon (without blocking sequence) in response to different amounts of its complementary target. Analogous data for blocked (toehold) beacons are shown for comparison (data from FIG. 2.1). (B) Multiplexed assay for two targets. The column plots summarize the time-gated fluorescence signals from each reporter dye in response to the indicated concentrations of the two targets in a mixture. The line plot is an average of each reporter dye signal for all data points at the indicated concentration of target, regardless of the amount of the other target. The data demonstrates independent detection of both targets.
Figure 14B:
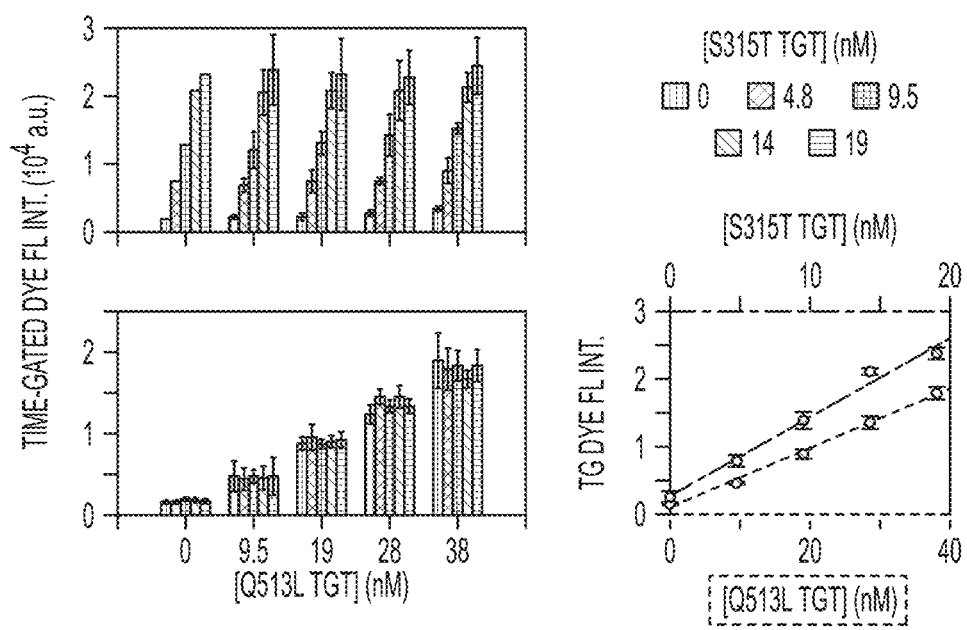

A particularly interesting finding was that the A488-Q513L-Tb and A546-S315T-Tb probes without the block sequence also functioned as time-gated beacons for the detection of their respective DNA targets. As shown in FIG. 14A, the time-gated emission from the reporter dyes was near background levels in the absence of target but increased significantly with the addition of complementary target, reaching a maximum at approximately one equivalent relative to the probe (data not shown). The calibration curves for the unblocked beacons had sensitivity comparable to that of the IabFQ-blocked toehold beacons, with LODs of 0.9 nM for both the A488-Q513L-Tb and A546-S315T-Tb. FIG. 14B shows that two-plex assays were also possible with the unblocked beacons, again with nearly orthogonal detection of the two targets (relative standard deviations for the average signals were between 5% and 10%).

Mechanism of Signaling with Unblocked Beacons.

With the unblocked beacons, the signaling mechanism was entirely temporal. There was no quencher dye for competitive energy transfer; the Tb emission intensity was insensitive to hybridization state, and the A488 and A546 reporter dyes retained their prompt emission intensity, ruling out formation of a nonfluorescent complex or other quenching mechanisms in the absence of hybridization with a blocking or target sequence. If the unhybridized probes were linear, the separation between the Tb and reporter dye would have been in the vicinity of the "sweet spot" for optimum signal intensity in TR-FRET, and the reporter dyes would have exhibited much larger time-gated fluorescence signals. It was therefore postulated that the reporter dyes and Tb were brought close enough together to support a temporal signaling effect (i.e., too high a FRET efficiency for time-gated measurements) through either the secondary structure of the single-stranded probe or spontaneous physical association between the Tb and reporter dye. Secondary structure predictions showed that both the S315T and Q513L probes had folded, hairpin-like structures with dangling ends that could place the reporter dye and Tb in close proximity. The predicted melt temperature values, $T_m$[38,39] for these secondary structures in TBS were ca. 40° C. and 43° C. for S315T and Q513L, respectively. To test the secondary structure hypothesis, solutions of A546-S315T-Tb probe were mixed with 17 different solvents, surfactants, and other additives. Of these additives, only formamide (60% v/v), dimethylformamide (DMF; 60% v/v), and cetyltrimethylammonium bromide (CTAB; 0.1% w/v) induced an increase in the time-gated dye emission intensity. Each of these additives is known to affect DNA structure: formamide disrupts hydrogen bonding in DNA;[44] DMF affects DNA hydration and counterions;[45] CTAB, a cationic surfactant, has electrostatic interactions with the DNA backbone.[46] These results suggested a role for the secondary structure of the probes in signaling. The effect of formamide was then further studied through a titration of the A546-S315T-Tb and A488-Q513L-Tb probes. An increase in time-gated reporter dye emission intensity was not observed until >50% v/v formamide was added. Formamide has been reported to decrease DNA duplexes by 0.65° C. per percent formamide added (or 2.4-2.9° C./M formamide).[47-50] The estimated $V_m$ values in experiments were 65-70% v/v, where $V_m$ is the percentage (v/v) of formamide at which half the probes have a random coil structure at room temperature. The expected $V_m$, extrapolated from the predicted $T_m$ or the probe secondary structures, was only 30% v/v. Even allowing for a reduced effect of formamide on interstrand folding versus two-strand hybridization, the value of $V_m$ was expected to be <50% v/v, suggesting that there was additional stabilization of the folded state of the unblocked beacons. As we have previously observed indications of nonspecific interactions between the Tb and various dyes in bulk solution,[36] it is likely that van der Waals interactions between the Tb and the reporter dyes provided this additional stabilization. Such interactions imply very close proximity between the dye and Tb, which is consistent with the low levels of background from the dye in the absence of target (comparable to blocked beacons with IabFQ quencher) and the high signal contrast via the temporal effect upon addition of target.

Hybridization Kinetics and Selectivity.

Figure 15:
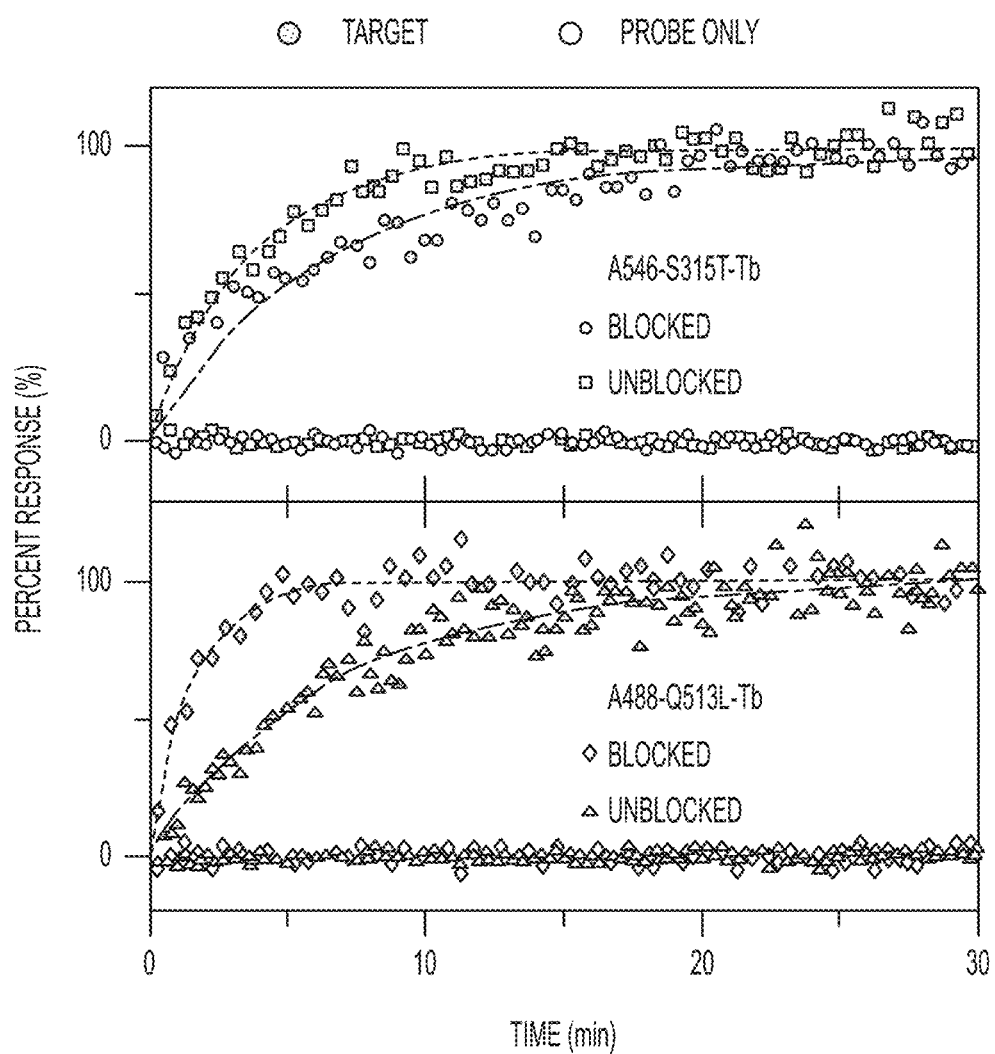
FIG. 15 shows hybridization kinetics for the A546-S315T-Tb and A488-Q513L-Tb probes, in the blocked (toehold) and unblocked configurations, with 0.4 equivalents of target. The concentration of the A546-S315T-Tb probe was 25 nM and the concentration of the A488-Q513L-Tb probe was 50 nM.

FIG. 15 shows progress curves for the hybridization of 0.4 equivalents of unlabeled target with both blocked (i.e., toehold) and unblocked A488-Q513L-Tb and A546-S315T-Tb beacons. Response times (90% of the maximum signal change) were in the range of 5-10 min for unblocked probes and 15-20 min for blocked probes. Analogous results were obtained with 0.2 and 0.7 equivalents of target (data not shown). The slower hybridization kinetics associated with the blocked beacons were expected given that a blocking sequence had to be displaced with these probes but not with the unblocked probes.

Figure 16A:
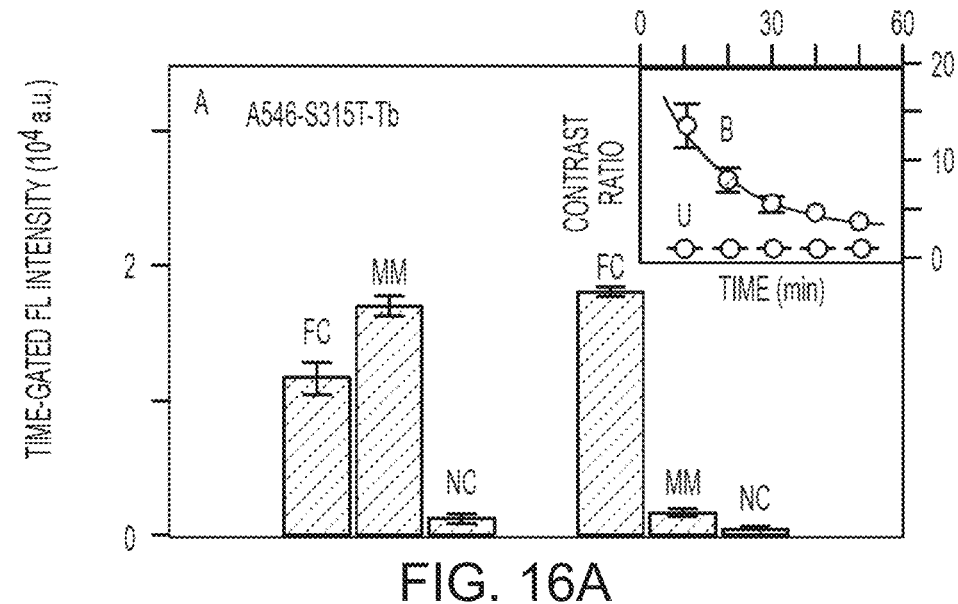
FIGS. 16A and 16B illustrate the selectivity of (A) A546-S315T-Tb and (B) A488-Q513L-Tb beacons in the blocked (toehold) and unblocked configurations toward fully complementary (FC) target sequences, mismatched sequences (MM), and non-complementary sequences (NC). For A546-S315T-Tb the mismatch is 2 bpm; for A488-Q513L-Tb the mismatch is 1 bpm. The insets show the contrast ratio between time-gated reporter fluorescence signals as a function of hybridization time. The main panel is for a hybridization time of 10 min.
Figure 16B:
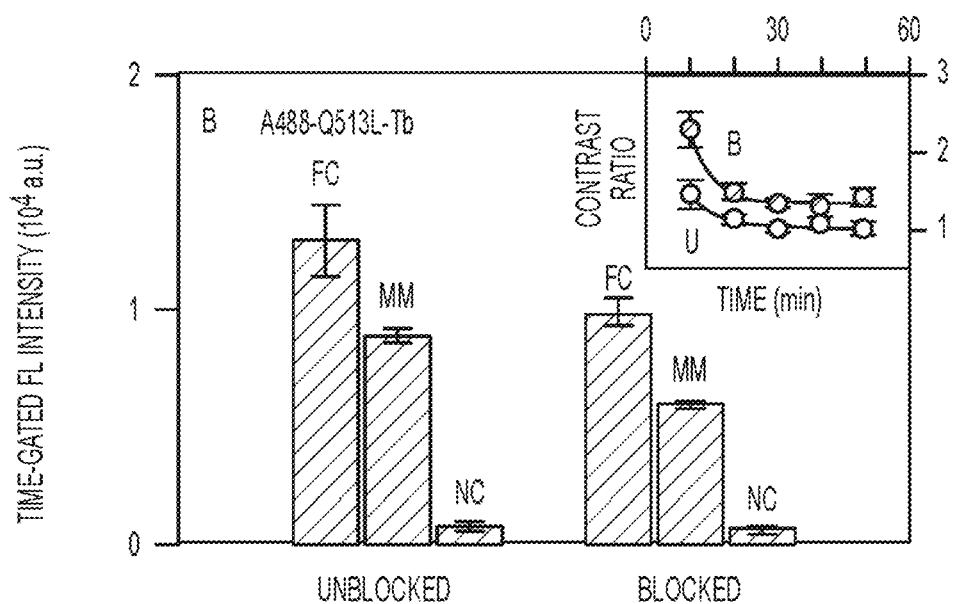

Although the blocked and unblocked A488-Q513L-Tb and A546-S315T-Tb beacons had comparable hybridization kinetics, their selectivity differed. The selectivity of the Q513L and S315T probes was tested using clinically relevant mismatched target sequences,[40-43] which had a one base pair mismatch (1 bpm) and two base pair mismatches (2 bpm), respectively, in the toehold region of the probe. FIG. 16 shows that both unblocked beacons were unable to distinguish between fully complementary target and the mismatched sequences. This result was expected given that the predicted $T_m$ values[38,39] for the mismatched hybrids were 58 and 52° C. for the Q513L and S315T, respectively. In contrast, FIG. 2.7 shows that the toehold/blocked beacons were able to provide some selectivity, with the signal contrast between fully complementary and mismatched target decreasing as a function of assay time. For the Q513L 1 bpm, the contrast was a modest 2.3:1 at 10 min hybridization time and decreased to 1.3:1 (almost no contrast) by 30 min. For the S315T 2 bpm, the contrast was 13:1 at 10 min and decreased to 4:1 at 50 min. The percent response to target at 10 min is approximately 75% for both blocked probes. These trends in selectivity agree with expectations. As indicated by the $T_m$ values, both the fully complementary target and mismatched sequences will have stable equilibrium hybridization under the assay conditions. Displacement of the blocking sequence of the toehold beacons provides a kinetic barrier to initial hybridization of the target and mismatched sequences, as well as a competitive hybridization equilibrium, thus providing greater selectivity than the unblocked beacons. The toehold beacon selectivity decreased with time as the kinetic barrier was overcome. Mismatches in the 5 nt toehold region of the probe slow down displacement of the blocking sequences to a degree proportional to the number of mismatches, as demonstrated by the much better selectivity against the S315T 2 bpm versus the Q513L 1 bpm.

Assays in Complex Matrices.

Figure 17A:
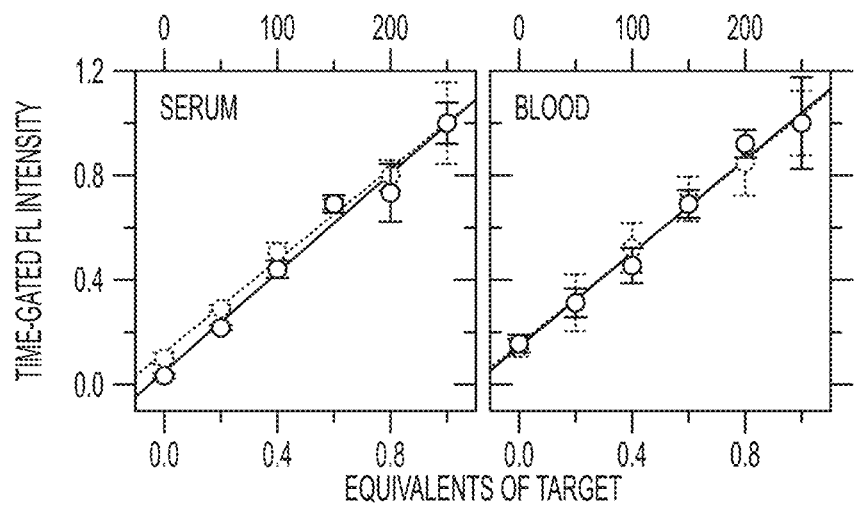
FIGS. 17A and 17B are calibration plots for (A) A546-S315T-Tb and (B) A488-Q513L-Tb beacons in serum and blood, for both the blocked and unblocked configurations.
Figure 17B:
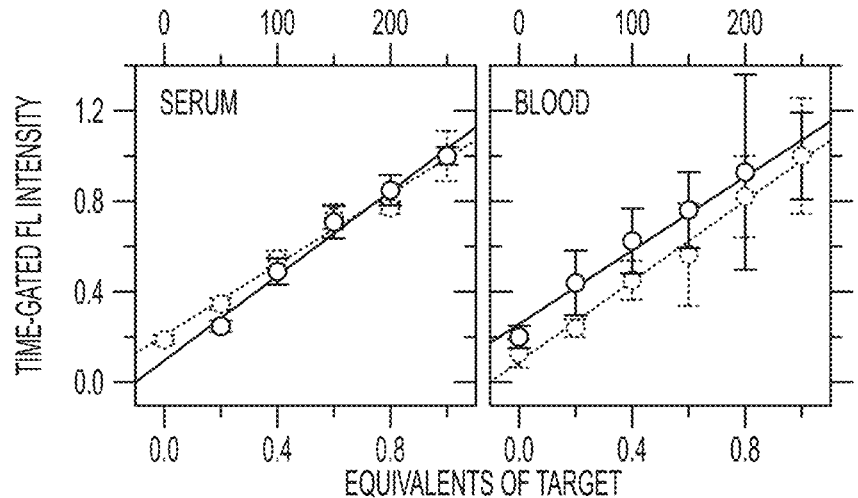

As noted above, the millisecond-scale excited state lifetime of the Tb enables time-gated measurements. This measurement modality permits temporal effect-based signaling via energy transfer, rejection of directly excited dye emission that provides unwanted back-ground signal in energy transfer assays, and rejection of background scatter and autofluorescence from complex bio-logical sample matrices. To demonstrate detection in complex sample matrices, the A488-Q513L-Tb and A546-S315T-Tb beacons, both blocked and unblocked, were tested in serum and blood matrices (>90% v/v). The working concentration of the probes was increased to 250 nM to compensate for attenuation of excitation light and emission through scatter and absorption by the sample matrices (less attenuation was observed with dilution of the serum with buffer). Standard curves are shown in FIG. 17 for complementary target spiked into serum and blood and have a linear trend similar to those in FIGS. 12 and 14, albeit with a reduction in precision for the blood matrix. Selectivity against mismatches was somewhat reduced in serum, likely due to its higher ionic strength than TBS. Contrast ratios were again time dependent, higher for the S315T 2 bpm than the Q513L 1 bpm, and had maximum values of 4:1 and 1.8:1, respectively, at 5 min for the blocked beacons. Overall, it was clear that both the blocked and unblocked beacons retained their functionality in serum and blood matrices.

Discussion.

The blocked and unblocked beacons offered a unique set of advantages for optical nucleic acid detection: single-step, light-up, time-gated, and multiplexed detection of unlabeled targets in blood and serum matrices, all while utilizing only a single excitation wavelength. These cumulative advantages cannot be matched by probes utilizing only fluorescent dyes, and the unblocked beacons remarkably provide these advantages as a unimolecular probe. The nanomolar detection limits for the blocked and unblocked beacons are competitive with other nonenzymatic, ensemble light-up assays[11,14,15,19,24] and are likely scalable to lower levels. The detection limit is determined, in part, by the background signal from the probe in its initial state, which scales with probe concentration. The dynamic range was from ca. 3-5% of the probe concentration up to 100%, and more sensitive instrumentation (e.g., utilizing a pulsed laser excitation source instead of a flash lamp) would permit the use of lower probe concentrations and thus provide lower absolute detection limits. Importantly, time-gating will permit the use of higher intensity excitation sources with biological sample matrices without large increases in back-ground. In addition, multiplexed assays for three targets should be possible with both blocked and unblocked beacons, as the multiple emission lines of Tb support energy transfer to longer-wavelength dyes (e.g., A647) that are spectrally resolved from A488 and A546. Crosstalk corrections may even permit a six-color multiplexed assay, as previously demonstrated for TR-FRET sandwich immunoassays.[51] Comparing the two configurations, the unblocked beacons had similar figures of merit versus the blocked beacons in all sample matrices and were only at a disadvantage in terms of selectivity against mismatched targets. In the case of the blocked beacons, greater selectivity toward a 1 bpm may be obtainable by reducing the length of the toehold region (at the potential expense of slower displacement kinetics) or by increasing the stringency of the assay conditions (e.g., lower ionic strength, higher temperature, added formamide, etc.).

Whereas the blocked beacons were rationally designed, our experiments showed that the unblocked beacons relied on the intrinsic secondary structure of the probe sequences, as well as putative van der Waals interactions between the Tb and reporter dye, to generate an initial state with low time-gated fluorescence from the reporter dye. In contrast to other FRET assay formats, the increase in reporter dye fluorescence was the result of a decrease in the efficiency of FRET from the Tb donor, so as to better align with the aforementioned "sweet spot" for TR-FRET measurements. Importantly, the probe sequences were clinically relevant, targeting genetic markers for tuberculosis, and were not intentionally designed to have a folded secondary structure. Many other probe sequences will have similar intrinsic secondary structure motifs, such that the unblocked configuration is likely applicable with a variety of targets. More generally, conventional molecular beacons could also be designed. Conventional molecular beacons consist of a stem-loop structure with no dangling ends, where the loop is a probe sequence and the stem segments are rationally designed additions to the probe sequence that close it into a loop. Although the structure switching upon target hybridization is similar between the unblocked beacons and conventional molecular beacons, the unblocked beacons differ from molecular beacons in that they fold into hairpin structures with small loops and dangling ends according to the probe sequence and are stabilized by some natural self-complementarity (and interactions between the Tb and dye) rather than rationally designed stem segments. The "beacon" terminology is retained in our study to indicate light-up signaling of target hybridization. To date, the temporal quenching effect may have been underappreciated in conventional LLC-based molecular beacons, as there seems to be few, if any, reports where a LLC has been paired with a fluorescent dye. The performance of our unblocked beacons indicate that such a configuration would be effective and that a dark quencher would not be required. Although the foregoing concepts are likely to be generally applicable with LLCs, one caveat is that superior analytical performance will be obtained with very bright and stable LLCs. The Lumi4-Tb cryptate[37] satisfies these criteria better than several more common terbium(III) and europium(III) chelates (e.g., those based on terpyridine ligands). Other promising LLCs based on europium(III) have also been reported in the literature.[52]

Beyond DNA detection, both the blocked and unblocked configurations are expected to be suitable for RNA detection, and protein detection may also be possible in blocked or unblocked formats by using an aptamer as the probe sequence. Moreover, it may be possible to design peptide or other biomolecular probes that signal their targets through the temporal quenching effect that was critical to the unblocked beacons. Functional DNA nanotechnology, such as FRET-based logic gates,[53] may also benefit from the addition of the unblocked beacon signaling mechanism to its photonic toolbox.

2.5 CONCLUSIONS

We have demonstrated two nonstem-loop designs for TR-FRET-based nucleic acid hybridization beacons. Both designs utilized a probe oligonucleotide labeled at its opposite termini with Lumi4-Tb and a fluorescent reporter dye, where time-gated emission from the dye provided a signal proportional to the amount of target. The first design was a blocked beacon that signaled target binding through toehold-mediated strand displacement of a quencher dye-labeled blocking sequence, whereas the second design was an unblocked beacon that relied on the intrinsic folding properties of the probe, stabilized by putative dye-Tb interactions, for signaling target. Both beacon designs offered nanomolar (femtomole) detection limits, response times on the order of minutes, multiplexing through different reporter dyes, and detection in complex biological matrices such as serum and blood. The unblocked beacons were particularly remarkable in their analytical performance, falling short of the blocked beacons only in terms of selectivity toward partially mismatched targets. The unblocked beacons also demonstrated the viability and effectiveness of a new temporal mechanism for light-up signaling in TR-FRET assays. This temporal mechanism, which also contributed to signaling with the blocked beacons, has prospective applications in other bioassay formats and in functional DNA nanotechnology.

2.6 REFERENCES (1) Cagnin, S.; Caraballo, M.; Guiducci, C.; Martini, P.; Ross, M.; SantaAna, M.; Danley, D.; West, T.; Lanfranchi, G. *Sensors* 2009, 9, 3122-3148.
(2) Johnson, B. N.; Mutharasan, R. *Analyst* 2014, 139, 1576-1588.
(3) Bao, G.; Rhee, W. J.; Tsourkas, A. *Annu. Rev. Biomed. Eng.* 2009, 11, 25-47.
(4) Juskowiak, B. *Anal. Bioanal. Chem.* 2011, 399, 3157-3176.
(5) Wetmur, J. G.; Fresco, *J. Crit. Rev. Biochem. Mol. Biol.* 1991, 26, 227-259.
(6) Sassolas, A.; Leca-Bouvier, B. D.; Blum, L. J. *Chem. Rev.* 2008, 108, 109-139.
(7) Marti, A. A.; Jockusch, S.; Stevens, N.; Ju, J. Y.; Turro, N. J. *Acc. Chem. Res.* 2007, 40, 402-409.
(8) Marras, S. A. E.; Tyagi, S.; Kramer, F. R. *Clin. Chim. Acta* 2006, 363, 48-60.
(9) Doré K.; Dubus, S.; Ho, H. S.; Levesque, I.; Brunette, M.; Corbeil, G.; Boissinot, M.; Boivin, G.; Bergeron, M. G.; Boudreau, D.; Leclerc, M. *J. Am. Chem. Soc.* 2004, 126, 4240-4244.
(10) Gaylord, B. S.; Massie, M. R.; Feinstein, S. C.; Bazan, G. C. *Proc. Natl. Acad. Sci. U.S.A.* 2005, 102, 34-39.
(11) Algar, W. R.; Krull, U. J. *Anal. Chem.* 2009, 81, 4113-4120.
(12) Zhang, C.-Y.; Hu, J. *Anal. Chem.* 2010, 82, 1921-1927.
(13) Yeh, H. C.; Sharma, J.; Han, J. J.; Martinez, J. S.; Werner, J. H. *Nano Lett.* 2010, 10, 3106-3110.
(14) Zhang, Y.; Zhu, C. F.; Zhang, L.; Tan, C. L.; Yang, J.; Chen, B.; Wang, L. H.; Zhang, H. *Small* 2015, 11, 1385-1389.
(15) Zhou, F.; Krull, U. J. *Anal. Chem.* 2014, 86, 10932-10939.
(16) Ye, W. W.; Tsang, M. K.; Liu, X.; Yang, M.; Hao, J. H. *Small* 2014, 10, 2390-2397.
(17) Krasnoperov, L. N.; Marras, S. A. E.; Kozlov, M.; Wirpsza, L.; Mustaev, A. *Bioconjugate Chem.* 2010, 21, 319-327.
(18) Lehmusvuori, A.; Kiviniemi, M.; Ilonen, J.; Soukka, T. *Anal. Biochem.* 2014, 465, 6-11.
(19) Li, J.; Zhou, W.; Ouyang, X.; Yu, H.; Yang, R.; Tan, W.; Yuan, J. *Anal. Chem.* 2011, 83, 1356-1362.
(20) Lopez-Crapez, E.; Bazin, H.; Andre, E.; Noletti, J.; Grenier, J.; Mathis, G. *Nucleic Acids Res.* 2001, 29, e70.
(21) Sueda, S.; Yuan, J. L.; Matsumoto, K. *Bioconjugate Chem.* 2000, 11, 827-831.
(22) Tsourkas, A.; Behlke, M. A.; Xu, Y. Q.; Bao, G. *Anal. Chem.* 2003, 75, 3697-3703.
(23) Jin, Z.; Geißler, D.; Qiu, X.; Wegner, K. D.; Hildebrandt, N. *Angew. Chem., Int. Ed.* 2015, 54, 10024-10029.
(24) Qiu, X.; Hildebrandt, N. *ACS Nano* 2015, 9, 8449-8457.
(25) Doughan, S.; Uddayasankar, U.; Krull, U. J. *Anal. Chim. Acta* 2015, 878, 1-8.
(26) Hildebrandt, N.; Wegner, K. D.; Algar, W. R. *Coord. Chem. Rev.* 2014, 273-274, 125-138.
(27) Amoroso, A. J.; Pope, S. J. A. *Chem. Soc. Rev.* 2015, 44, 4723-4742.
(28) Bünzli, J.-C. G. *Chem. Rev.* 2010, 110, 2729-2755.
(29) Selvin, P. R.; Hearst, J. E. *Proc. Natl. Acad. Sci. U.S.A* 1994, 91, 10024-10028.
(30) Selvin, P. R.; Rana, T. M.; Hearst, J. E. *J. Am. Chem. Soc.* 1994, 116, 6029-6030.
(31) Hagan, A. K.; Zuchner, T. *Anal. Bioanal. Chem.* 2011, 400, 2847-2864.
(32) Hemmila, I.; Laitala, V. *J. Fluoresc.* 2005, 15, 529-542.
(33) Gudgin Dickson, E. F.; Pollak, A.; Diamandis, E. P. *J. Photochem. Photobiol., B* 1995, 27, 3-19.
(34) Degorce, F. *Expert Opin. Drug Discovery* 2006, 1, 753-764.
(35) Carlson, C. B.; Robers, M. B.; Vogel, K. W.; Machleidt, T. *J. Biomol. Screening* 2009, 14, 121-132.
(36) Massey, M.; Ancona, M. G.; Medintz, I. L.; Algar, W. R. *ACS Photonics* 2015, 2, 639-652.
(37) Xu, J.; Corneillie, T. M.; Moore, E. G.; Law, G. L.; Butlin, N. G.; Raymond, K. N. *J. Am. Chem. Soc.* 2011, 133, 19900-19910.
(38) Markham, N. R.; Zuker, M. *Nucleic Acids Res.* 2005, 33, W577-W581.
(39) Markham, N. R.; Zuker, M. *Methods Mol. Biol.* 2008, 453, 3-31.
(40) Dubiley, S.; Mayorova, A.; Ignatova, A.; Kirillov, E.; Stepanshina, V.; Kolesnikov, A.; Shemyakin, I. *Clin. Chem.* 2005, 51, 447-450.
(41) Sougakoff, W.; Rodrigue, M.; Truffot-Pernot, C.; Renard, M.; Durin, N.; Szpytma, M.; Vachon, R.; et al. *Clin. Microbiol. Infect.* 2004, 10, 289-294.
(42) Yu, S.; Girotto, S.; Lee, C.; Magliozzo, R. S. *J. Biol. Chem.* 2003, 278, 14769-14775.
(43) Byrom, M.; Bhadra, S.; Jiang, Y. S.; Ellington, A. D. *Nucleic Acids Res.* 2014, 42, e120.
(44) Blake, R. D.; Delcourt, S. G. *Nucleic Acids Res.* 1996, 24, 2095-2103.
(45) Sen, A.; Nielsen, P. A. *Nucleic Acids Res.* 2007, 35, 3367-3374.
(46) Liu, Q.; Li, J.; Tao, W.; Zhu, Y.; Yao, S. *Bioelectrochemistry* 2007, 70, 301-307.
(47) McConaughy, B. L.; Laird, C. D.; McCarthy, B. I. *Biochemistry* 1969, 8, 3289-3295.
(48) Record, M. T., Jr. *Biopolymers* 1967, 5, 975-992.
(49) Casey, J.; Davidson, N. *Nucleic Acids Res.* 1977, 4, 1539-1552.
(50) Hutton, J. R. *Nucleic Acids Res.* 1977, 4, 3537-3555.
(51) Geißler, D.; Stufler, S.; Löhmannsröben, H. G.; Hildebrandt, N. *J. Am. Chem. Soc.* 2013, 135, 1102-1109.
(52) Walton, J. W.; Bourdolle, A.; Butler, S. J.; Soulie, M.; Delbianco, M.; McMahon, B. K.; Pal, R.; Puschmann, H.; Zwier, J. M.; Lamarque, L.; Maury, O.; Andraud, C.; Parker, D. *Chem. Commun.* 2013, 49, 1600-1602.
(53) LaBoda, C.; Duschl, H.; Dwyer, C. *Acc. Chem. Res.* 2014, 47, 1816-1824.

Chapter 3: Time-Gated DNA Photonic Logic Operators

3.1 BACKGROUND

Boolean logic processes information in terms of true and false, terms that are often represented by 1 and 0 bits in electronic devices that operate using binary. True or false statements of information can be combined using logical operators. Although there are several logical operators, the most basic and intuitive operators are AND and OR. NAND and NOR gates are universal logic gates, and can be used to construct all other logic gates. These operators have two inputs and one output, all of which can take on values of either 0 or 1. For an AND operator, both inputs must have a value of 1 for the output to have a value of 1. In contrast, for an OR operator, only one input must have a value of 1 for its output to have a value of 1. A NAND operator returns an output of 0 when both inputs are 1, and NOR only returns an output of 1 when both inputs are 0. Truth tables that tabulate input versus output of these operators are shown in FIG. 18.

Physical manifestations of logical operators are the underpinnings of modern digital electronic technology. In this case, circuits are designed to produce either a high or low voltage output in response to either high or low voltage inputs. There has been significant interest in duplicating this process at the molecular level. Molecular logic devices (MLDs)[1-9] differ from digital logical devices in that the inputs are chemical or biochemical in nature, and the outputs tend to be photonic or electrochemical, but otherwise aim to have input/output characteristics that are analogous to the truth tables for their digital logic counterparts. For example, a molecular AND operator will only produce a photonic output if it receives two appropriate biochemical inputs. In this context, MLDs are promising components for the assembly of non-traditional information processing systems that function on the nanoscale and in biological environments. A particularly interesting application of such information processing is rapid diagnostic screening, where a MLD-based computation generates a true or false output for the health state of an individual, where the false output would be an indicator for further biomedical testing. By looking at multiple biochemical bits of information, and computing a single output, a MLD can make possible a fast, simple, and economical screening assay that can be conducted by an unskilled or minimally-skilled technician.

Here, we evaluate the potential for DNA-based logical operators that utilize the concepts of time-gated Förster resonance energy transfer already described in Chapters 1 and 2 above. These operators are composed of two or more oligonucleotides hybridized together in specific arrangements, accept two complementary oligonucleotides as inputs with values of 1, and convert that information into a photonic output of time-gated fluorescence intensity. The AND and OR operators were selected for initial development because of their fundamental roles in Boolean logic and their clear applicability to downstream health care applications. Two prospective AND operators, three prospective OR operators, and both NAND and NOR operators were designed and tested experimentally, as described in the following sub-sections. The results show that functional DNA-based photonic AND, OR, NAND, and NOR operators can be constructed, and we identify some of the requirements and limitations in designing these operators.

3.2 EXPERIMENTAL SECTION

Oligonucleotide Sequences.

Table 3 lists the oligonucleotide sequences used in the assembly of the logical operators.

Labeling of Oligonucleotide Probes.

Oligonucleotides were labeled with two dyes and Lumi4-Tb, one dye and Lumi4-Tb, or only Lumi4-Tb according to the sequences listed in Table 3. The oligonucleotides were obtained from the manufacturer (Integrated DNA Technologies, Coralville, Iowa) with thiol- and amine-terminated linkers at the appropriate position to construct the probe conjugates. In the cases where oligonucleotide sequences were labeled with dye or quencher only, the oligonucleotides were purchased with the dye label already conjugated. For in-house labeling, the probes were labeled with maleimide-functionalized dye by reducing the disulfide protecting group of the oligonucleotide linker to a reactive thiol group using tris(2-carboxyethyl)phosphine (TCEP). Probe oligonucleotides (45-50 nmol) were dissolved in 92 µL of Ultra-Pure water (Amresco, Solon, Ohio), and 8 µL of a 150 mM TCEP solution prepared in UltraPure water was added. The solution was mixed for 1 h, after which time the TCEP was removed using a NAP-10 size exclusion column (GE Healthcare, Baie-D'Urfé, QC, Canada) with elution using 4-(2-hydroxyethyl)-1-piperazineethanesulfonic acid (HEPES) buffer (100 mM, 50 mM NaCl, pH 7). The eluate (600 µL) was immediately mixed with 20 µL of dye dissolved in DMSO (12.5 mg/mL solution). The reaction was mixed overnight and subsequently purified using Bio-Gel P-4 (Bio-Rad, Mississauga, ON, Canada) size exclusion chromatography with triethylammonium acetate buffer (0.2 M TEAA, pH 7) as the eluent. A dye:DNA coupling ratio of ~1:1 was verified using UV-visible absorption spectrophotometry, with the exception of the AND FOR I probe, where a dye:DNA coupling ratio of ~2:1 was verified using UV-visible absorption spectrophotometry. The purified samples were dried in a vacuum centrifuge.

The DNA-dye conjugates were subsequently labeled at their amine linker (either at the 3' end or at an internal position according to the Tb labeling position shown in Table 3) using succinimidyl ester-functionalized Lumi4-Tb. A 5 mg/mL solution of Lumi4-Tb-NHS was prepared by dissolving ~1 mg of Lumi4-Tb-NHS in 200 µL of DMSO. The DNA-dye conjugates were dissolved in 150 µL of borate buffer (100 mM, pH 8.5), and 50 µL of DMSO was added to the solution. To this mixture, 100 µL of the Lumi4-Tb-NHS solution was added so that the final solvent was a 1:1 mixture (v/v) of DMSO and buffer. The reaction was mixed overnight and then diluted to 4 mL with 0.2 M TEAA buffer. The Tb-DNA-dye conjugates were concentrated on Amberchrom CG300M resin, then eluted using 70% v/v (aq) acetonitrile and dried in a vacuum centrifuge. The product was re-dissolved in 8 µL of DMSO, diluted to 50 µL with 0.2 M TEAA, and purified using size exclusion chromatography (Bio-Gel P-4) with 0.2 M TEAA as the eluent. A Tb:DNA:dye ratio of ~1:1:1 (or 1:2:1 in the case of the AND FOR I probe) was verified using UV-visible absorption spectrophotometry. DNA-Tb conjugates without a dye label were prepared in the same manner.

Assays and Emission Measurements.

DNA logical operators were assembled by mixing equivalent amounts of the constituent oligonucleotides in tris-borate saline (TBS) buffer (90 mM tris-borate, 137 mM NaCl, 2.7 mM KCl, pH 7.6). These samples were heated to 95° C. for 5 min, then cooled slowly to room temperature. Hybridization times for input oligonucleotides were 75 min. Luminescence measurements were made with a 2000 µs lag time and 2000 µs integration time unless otherwise noted.

Data Analysis.

The time-gated A546 PL intensity was processed as measured intensities in arbitrary units or, more commonly, normalized to the intensity measured for the sample with both target oligonucleotides added. This process is useful because the output for the (1, 1) input state will always be a value of 1, and is ideal for AND and OR operators. The effectiveness of the operator is then easily assessed based on how close the other output values are to 0 or 1, as appropriate.

For the A546-IabFQ pathway, the 0 output arises only from physical quenching of the A546 fluorescence emission.

AND-I Logical Operator.

FIG. 19 shows the AND-I photonic logical operator concept. The operator consists of two 19 nt probe arms joined through an internal amine linker that is labeled with Tb. The 3' and 5' termini of the probe are labeled with A546.

TABLE 3

Oligonucleotide sequences.

| Operator | Role | Sequence |
|---|---|---|
| AND-I | Probe | A546-5'-TAG GCT CAG CTG GCT GGT-(Tb)-TC GTG GTG ATC GCT TCC TT-3'-A546 (SEQ ID NO. 21) |
| | Block A | IabFQ-5'-ACC AGC CAG CTG A-3' (SEQ ID NO. 22) |
| | Block B | 5'-AAG GAC GCG ATC A-3'-IabFQ (SEQ ID NO. 23) |
| | Target A | 5'-ACC AGC CAG CTG AGC CTA-3' (SEQ ID NO. 24) |
| | Target B | 5' AAG GAC CGC ATC ACC ACG 3' (SEQ ID NO. 25) |
| AND-II | Probe | 5'-TAG GCT CAG CTG GCT GGT AAG GAC GCG ATC ACC ACG CAG TGA AGC GGT ACA TAG G-3' (SEQ ID NO. 26) |
| | Reporter | A546-5'-CGT GGT GAT CGC GTC CTT-3'-Tb (SEQ ID NO. 27) |
| | Block A | IabFQ-5'-ACC AGC CAG CTG A-3' (SEQ ID NO. 28) |
| | Block B | 5'-GTA CCG CTT CAC TG-3'-IabFQ (SEQ ID NO. 29) |
| | Target A | 5'-ACC AGC CAG CT AGC CTA-3' (SEQ ID NO. 30) |
| | Target B | 5'-CCT ATG TAC CGC TTC ACT G-3' (SEQ ID NO. 31) |
| OR-I | Probe | A546-5'-TAG GCT CAG CTG GCT GGT-(Tb)-TC GTG GTG ATC GCT TCC TT-3'-A546 (SEQ ID NO. 32) |
| | Block | 5'-CGC GTT CAC CTC GA-(BHQ2)-A ACC ACC CAC CTG A-3' (SEQ ID NO. 33) |
| | Target A | 5'-ACC AGC CAG CTG AGC CTA-3' (SEQ ID NO. 34) |
| | Target B | 5'-AAG GAC CGC ATC ACC ACG-3' (SEQ ID NO. 35) |
| OR-II | Probe | 5' CGC GAT CAC CAC GCA GTG AAG CGG TAC ATA GG-3' (SEQ ID NO. 36) |
| | Reporter | A546-5'-CGT GGT GAT CGC GTC CTT-3'-Tb (SEQ ID NO. 37) |
| | Block | 5'-GTA CCG CTT CAC TG-3'-IabFQ (SEQ ID NO. 38) |
| | Target A | 5'-AAG GAC GCG ATC ACC ACG 3' (SEQ ID NO. 39) |
| | Target B | 5'-CCT ATG TAC CGC TTC ACT G-3' SEQ ID NO. 40) |
| OR-III | Template | 5' TAG GCT CAG CTG GCT GGT AAG GAC GC*T* ATC ACC 3' (SEQ ID NO. 41) |
| | Block | IabFQ-5'-ACC AGC CAG CTG A-3' (SEQ ID NO. 42) |
| | Reporter | A546-5'-CGT GGT GAT CGC GTC CTT-3'-Tb (SEQ ID NO. 43) |
| | Target A | 5'-ACC AGC CAG CTG AGC CTA-3' (SEQ ID NO. 44) |
| | Target B | 5' AAG GAC CGC ATC ACC ACG 3' (SEQ ID NO. 45) |
| NAND | Template | 5'-TAG GCT CAG CTG GCT GGT - (Tb) - CGT GGT GAT *C*GC GTC CTT-3' (SEQ ID NO. 46) |
| | Block A | 5'-ACG TAC CAG CCA GCT GA 3' (SEQ ID NO. 47) |
| | Block B | A546-5'- AAG GAC GCT ATC ACC-3' (SEQ ID NO. 48) |
| | Target A | 5'- ACC AGC CAG CTG AGC CTA-3' (SEQ ID NO. 49) |
| | Target B | 5'-AAG GAC CGC ATC ACC ACG-3' (SEQ ID NO. 50) |
| NOR | Template | 5'- TAG GCT CAG CTG GCT GGT AAG GAC GC*T* ATC ACC-3' (SEQ ID NO. 51) |
| | Block A | Tb-5'-ACC AGC CAG CTG A-3' SEQ ID NO. 52) |
| | Probe B | A546-5'-CGT GGT GAT CGC GTC CTT-3' (SEQ ID NO. 53) |
| | Target A | 5'-ACC AGC CAG CTG AGC CTA-3' (SEQ ID NO. 54) |
| | Target B | 5'-AAG GAC CGC ATC ACC ACG-3' (SEQ ID NO. 55) |

Tb = Lumi4-Tb cryptate; A546 = Alexa Fluor 546; IabFQ = Iowa Black Dark Quencher: BHQ2 = Black Hole Quencher 2.

3.3 RESULTS AND DISCUSSION

Energy Transfer Pathways.

The oligonucleotide-based logical operators utilize three FRET pathways. The FRET pathway responsible for an output value of 1 is between the Tb donor and A546 fluorescent acceptor dye(s). Two FRET pathways are responsible for an output value of 0: FRET from the Tb donor to an IabFQ dark quencher, and FRET from a Tb-sensitized A546 donor to an IabFQ dark quencher. For the Tb-IabFQ FRET pathway, the zero output arises from both physical quenching of the Tb donor and shortening of the Tb lifetime to within the lag time for time-gated measurements.

In the initial state, each arm is hybridized with a 13 nt blocking sequence labeled with IabFQ. Both IabFQ labels are located in close proximity to the Tb, resulting in efficient quenching of its emission. When one target oligonucleotide is added, as either the (1, 0) or (0, 1) input, it hybridizes to its complementary arm through toehold-mediated strand displacement of the blocking sequence, but the remaining blocking sequence and IabFQ label continues to quench the Tb emission. Both IabFQ labels are displaced only when both oligonucleotides are added as the (1, 1) input state, resulting in FRET from the Tb to the A546, and time-gated A546 emission as an output value of 1.

Figure 20:
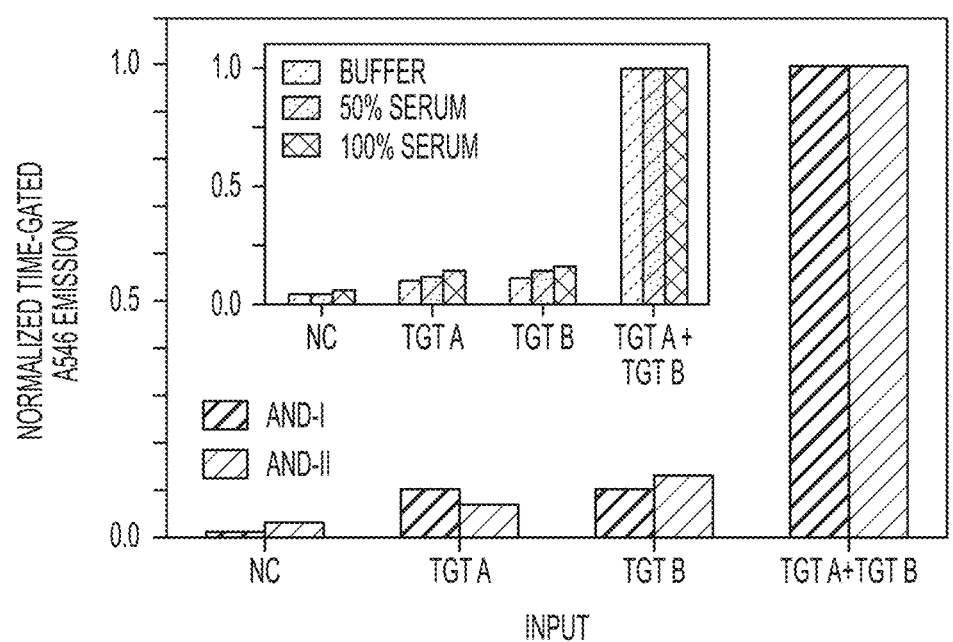
FIG. 20 shows time-gated A546 emission outputs for the AND-I and AND-II logical operator as a function of input: non-complementary (NC) DNA (0, 0), Target A (1, 0), Target B (0, 1), and both Target A and Target B (1, 1). The inset compares the outputs from the AND-1 logical operator between buffer and two concentrations of serum.

FIG. 20 shows results from the AND-I logical operator. In the absence of any complementary oligonucleotide, the time-gated A546 emission has a normalized or logical output value of 0.01. The normalized time-gated emission increases to a value of 0.1 when one target is added, and increases to a value of 1.0 when both targets are added. AND logical operator function is achieved by setting a threshold value of 0.2. The inset in FIG. 20 shows that the AND-I logical operator remains functional in 50% and 100% serum matrices, in large part because of the time-gated measurements made possible by the Tb donor.

Figure 21:
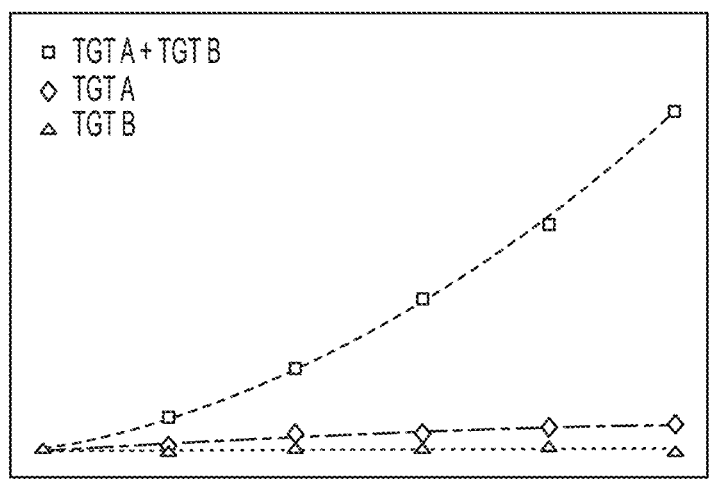
FIG. 21 shows time-gated A546 emission outputs for the AND-I logical operator as a function of the number of equivalents of target DNA added.

FIG. 21 shows calibration curves for the AND-I operator with different numbers of equivalents of Target A (1, 0), Target B (0, 1), and both targets (1, 1). The time-gated A546 emission increases only slowly with increasing equivalents of the (1, 0) and (0, 1) inputs, but increases significantly with increasing equivalents of the (1, 1) input.

Figure 22:
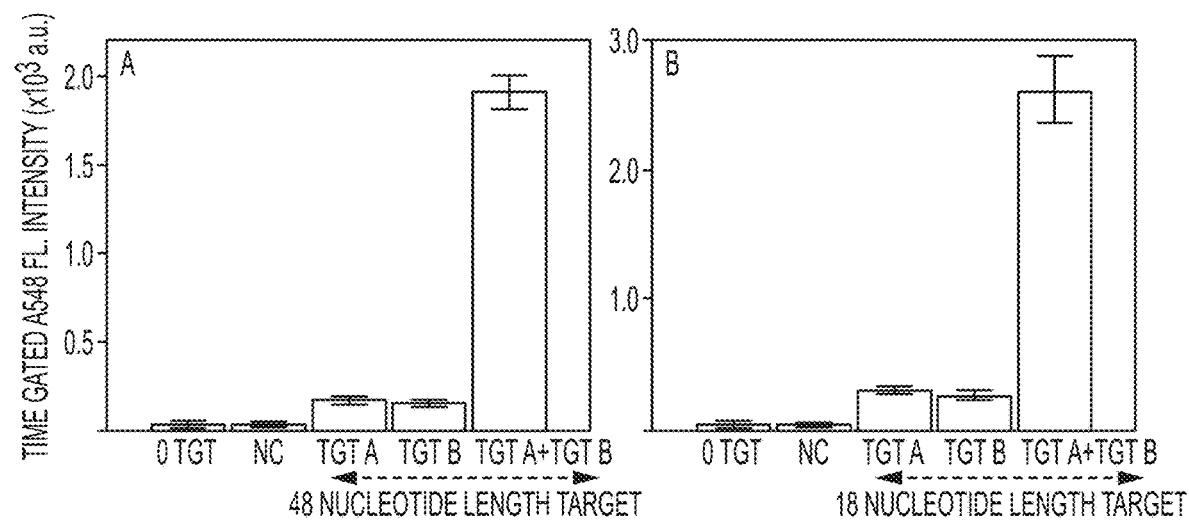
FIG. 22 illustrates time-gated A546 emission outputs for the AND I logical operator with two different target lengths: (A) 48 nucleotide targets, and (B) 18 nucleotide targets.

FIG. 22 shows results for the performance of the AND-I logical operator with target inputs of different lengths. The AND-I logical operator performs similarly for targets that are 18 nt in length and targets that are 48 nt in length. For the 48 nt targets, the targets were comprised of the same 18 nt complementary sequence to the probe arms and flanking ends that were 15 nt in length.

Figure 23A:
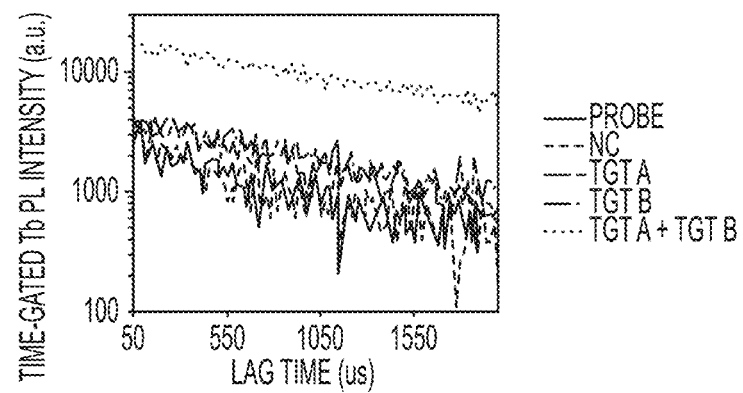
FIGS. 23A and 23B show PL decay curves for the AND-I logical operator as a function of input: non-complementary (NC) DNA (0, 0), Target A (1, 0), Target B (0, 1), and both Target A and Target B (1, 1).
Figure 23B:
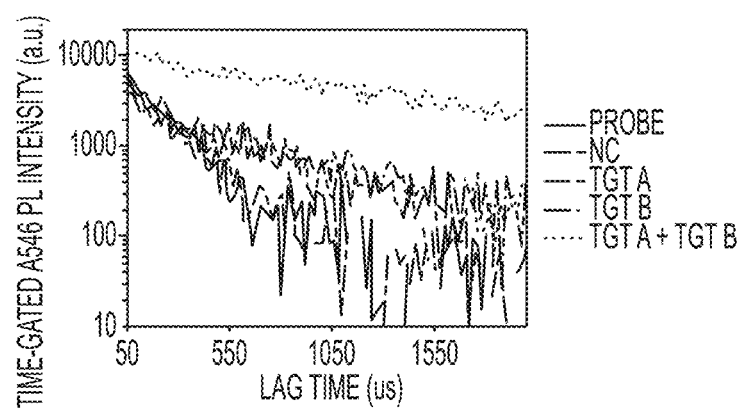

FIG. 23 shows emission decay curves for the four different states of the AND-I logical operator. The Tb data shows relatively uniform millisecond-lifetime decays, albeit that intensity of the (1, 1) input (both targets) is much higher than the other states. The A546 data shows a similar decay profile for the (1, 1) state, whereas the other states show indications of both a millisecond-lifetime decay and a shorter lifetime component on the order of hundreds of microseconds. A short lifetime component is consistent with our expectation for efficient energy transfer from the Tb to the IabFQ quencher. For the Tb data, it is assumed that this short component is too short to be resolved; however, it is not yet clear why this component would be resolved with the A546 data. Importantly, the raw data for the (1, 0) and (0, 1) states are very similar, as are the data sets for the AND-I logical operator itself (probe) and the AND-I logical operator mixed with non-complementary oligonucleotide.

Figure 24:
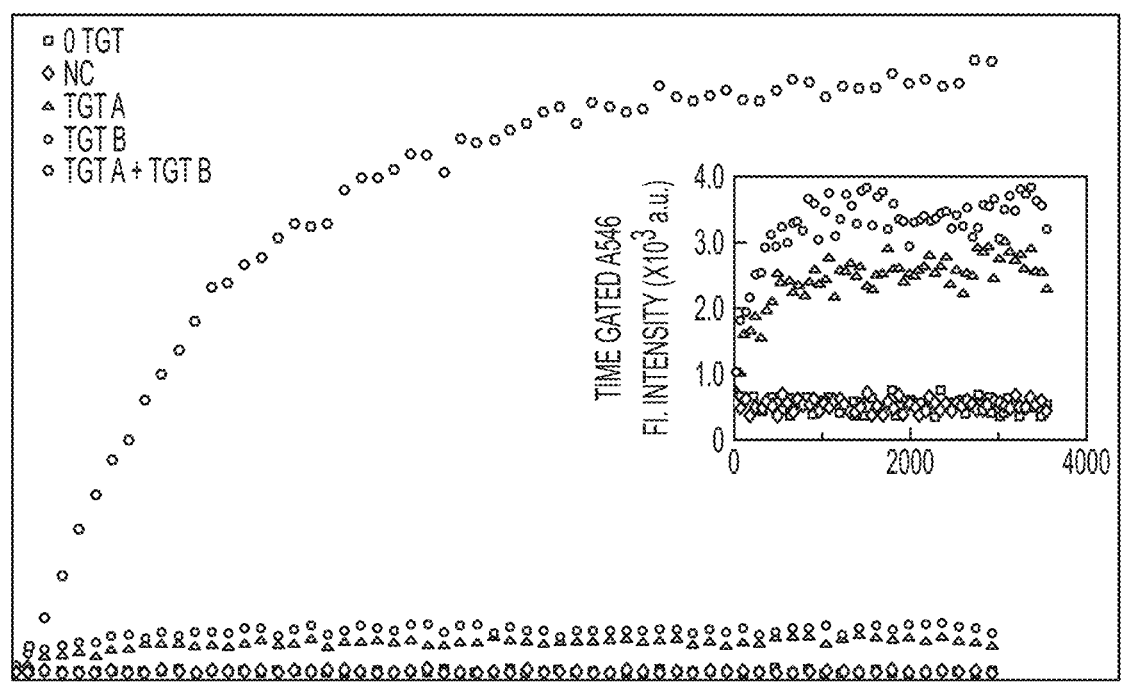
FIG. 24 shows kinetics of AND I logical operator performance as a function of input: non-complementary (NC) DNA (0, 0), Target A (1, 0), Target B (0, 1), and both Target A and Target B (1, 1). The inset shows an expanded view of the Target A (1,0) and Target B (0,1) kinetics compared to background signals

FIG. 24 shows progress curves for the kinetics of target input hybridization for each input of the AND-I logical operator. In the presence of only one target input, ((0,1) or (1,0) state), the time-gated A546 fluorescence signal intensity is low (see inset of FIG. 3.7). When both inputs were present ((1,1) state), the time gated A546 fluorescence signal intensity increased, with a response time (time required to reach 90% of the maximum signal change) of approximately 35 min. The AND-I gate is selective to its two target inputs and only returns a significant A546 time-gated fluorescence signal output when both inputs are present.

AND-II Logical Operator.

Figure 25:
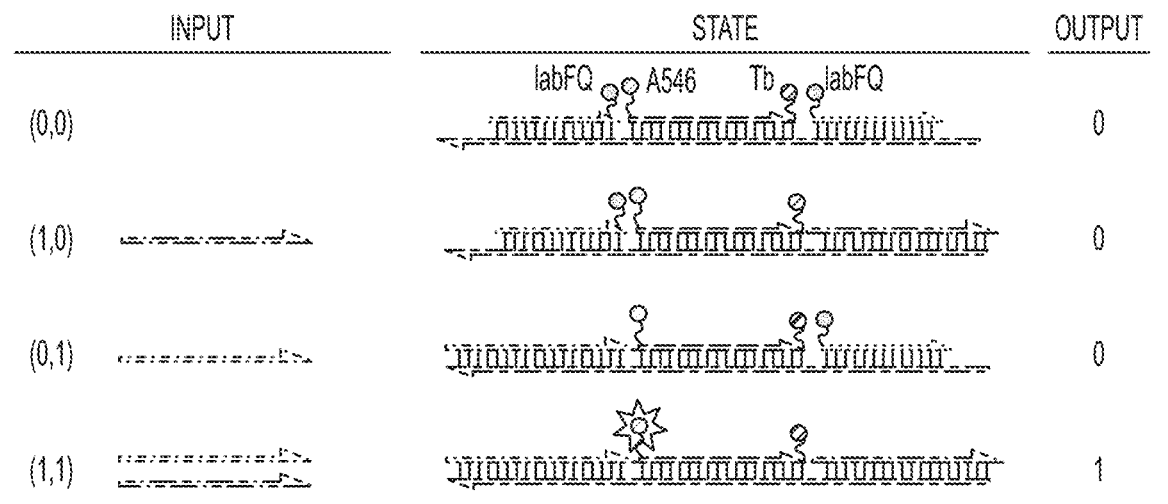

FIG. 25 shows the structure of the AND-II logical operator. In this case, an unlabeled 54 nt probe oligonucleotide is hybridized at a central position with a reporter strand that is labeled at opposite termini with Tb and A546. IabFQ-labeled blocking sequences hybridize adjacent to the reporter sequence, placing the IabFQ adjacent to both the A546 and Tb. Addition of one target (a (1, 0) or (0, 1) input) will displace one of the IabFQ; however, the remaining IabFQ continues to quench time-gated A546 emission, either by quenching the A546 itself or by quenching its Tb donor. The addition of both targets (a (1, 1) input) displaces both IabFQ labels and restores time-gated A546 emission.

The performance of the AND-II gate is shown in FIG. 20 alongside the AND-I gate. The output values were nearly identical between the two different AND operators.

Figure 26:
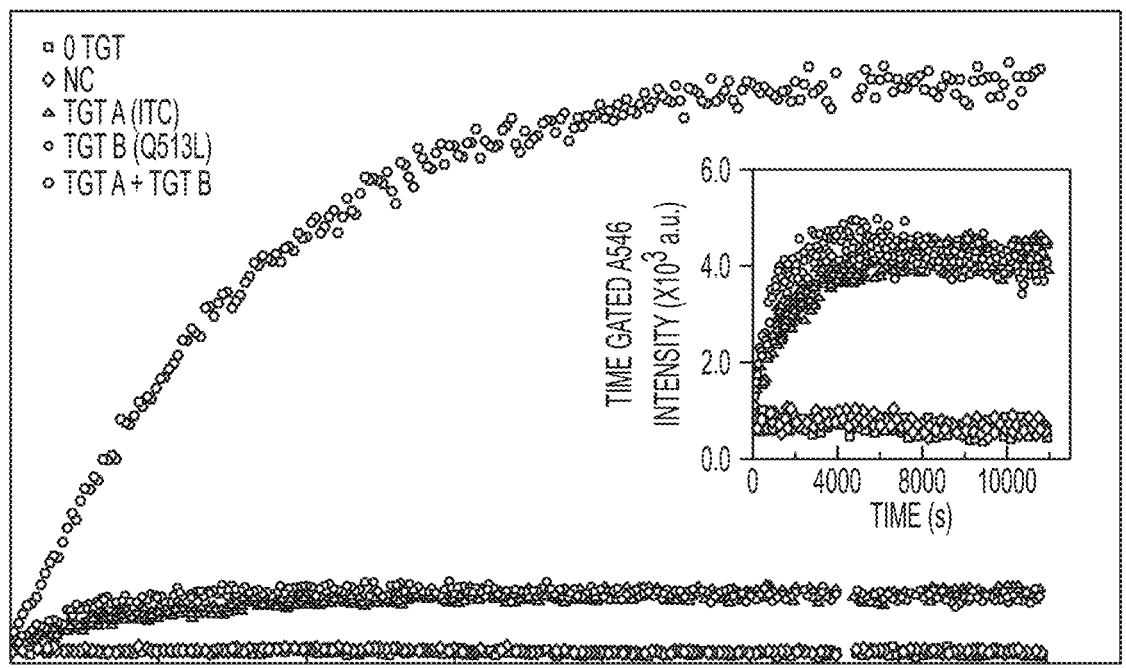
FIG. 26 shows kinetics of AND II logical operator performance as a function of input: non-complementary (NC) DNA (0, 0), Target A (1, 0), Target B (0, 1), and both Target A and Target B (1, 1). The inset shows an expanded view of the Target A (1,0) and Target B (0,1) kinetics compared to background signals.

FIG. 26 shows progress curves for the kinetics of target input hybridization for each input of the AND-II logical operator. In the presence of only one target ((0,1) or (1,0) state), the time-gated A546 fluorescence signal intensity is low (see inset of FIG. 3.9). When both inputs are present ((1,1) state), the time-gated A546 fluorescence signal intensity increases, with a response time of approximately 120 min. The AND-II gate is also selective to its two target inputs and only returns a significant A546 time-gated fluorescence signal output when both inputs are present.

OR-I Logical Operator.

FIG. 27 shows concept of the OR-I photonic logical operator. Analogous to the AND-I operator, the OR-I operator consists of two 19 nt probe arms joined through an internal amine linker that is labeled with Tb. The 3' and 5' termini of the probe are labeled with A546. The difference between the OR-I and AND-I operator is the blocking sequence that is hybridized to this probe. In the case of the OR-I operator, the blocking sequence also consists of two arms, each 14 nt in length to leave 5 nt toeholds at opposite termini of the OR-I operator; however, the two arms are joined by an internal amine linker that is labeled with IabFQ. Each arm of the blocking sequence includes two mismatches. When both arms of the blocking sequences are hybridized to the OR-I probe, as in the (0, 0) state, the hybrid is stable, and the IabFQ efficiently quenches the Tb. In principle, when one target hybridizes and displaces one arm of the blocking sequence, a (1, 0) or (0, 1) input, the remaining arm is too unstable to remain hybridized, and the blocking sequence dissociates from the probe with recovery of time-gated Tb and FRET-sensitized A546 emission. The anticipated outcome is analogous when both targets are added as the (1, 1) state.

Figure 28:
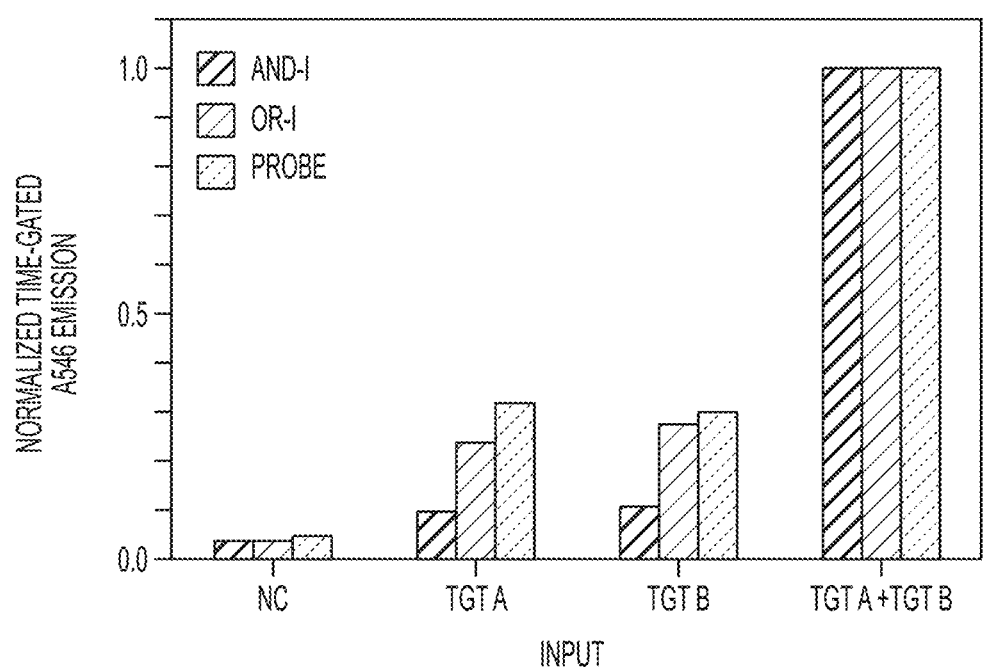
FIG. 28 shows time-gated A546 emission outputs for the AND-I, OR-I, and the probe itself (no blocking sequence) as a function of input: non-complementary (NC) DNA (0, 0), Target A (1, 0), Target B (0, 1), and both Target A and Target B (1, 1).

FIG. 28 shows the actual response of the OR-I gate. The normalized time-gated A546 emission output from the initial state is 0.04. With the addition of one target or the other (a (1, 0) or (0, 1) input), the output increases to 0.24-0.28. The output for both targets (a (1, 1) input), is 1.0. The output of the AND-I gate and the probe only (no blocking sequence) are also shown in FIG. 3.11 for reference. The ideal output from the OR-I operator would be 1.0 for the (1, 0), (0,1), and (1,1) inputs. Clearly, this was not the case. The OR-I operator clearly behaves differently than the AND-I operator, and a threshold value of 0.15 would function for both the OR-I and AND-I gates. Nonetheless, the contrast is quite poor and far from the ideal behavior.

The response of the probe to the four inputs in FIG. 28 provides insight into the poor contrast of the OR-I gate. With displacement of the blocking sequence, one of the arms of the probe remains double-stranded (by virtue of hybridization with target) and the other becomes single-stranded. The single-stranded state is able to quench the Tb as we described previously, similar to the unblocked beacons described above. The key to a successful OR logical operator is therefore to maintain a predominately double-stranded DNA structure between the Tb donor and acceptor in each state. Attempts to use short oligonucleotide "splints" to maintain a mostly double-stranded state after displacement of the blocking sequence were unsuccessful (data not shown), necessitating the design of the OR gates in the following sections.

OR-II Logical Operator.

Figure 29:
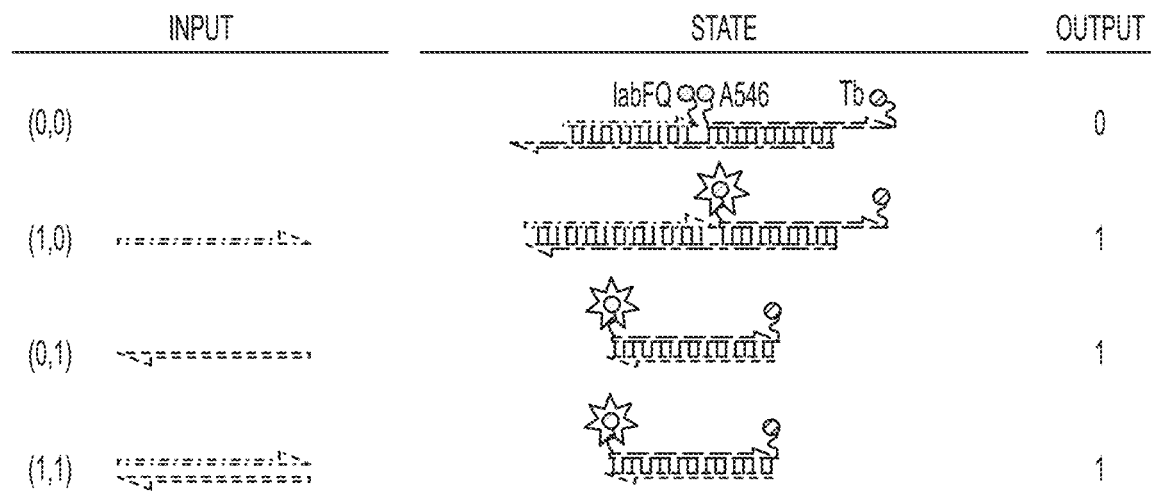

FIG. 29 shows the concept of the OR-II logical operator. The operator consists of an unlabeled 31 nt probe that is hybridized with the same reporter sequence as the AND-II gate; however, in this case the probe hybridizes with only the first 13 nt, leaving a 5 nt toehold. A 13 nt IabFQ-labeled sequence hybridizes to the probe adjacent to the reporter sequence, quenching the time-gated A546 emission while leaving a 5 nt toehold on the probe sequence.

Figure 30:
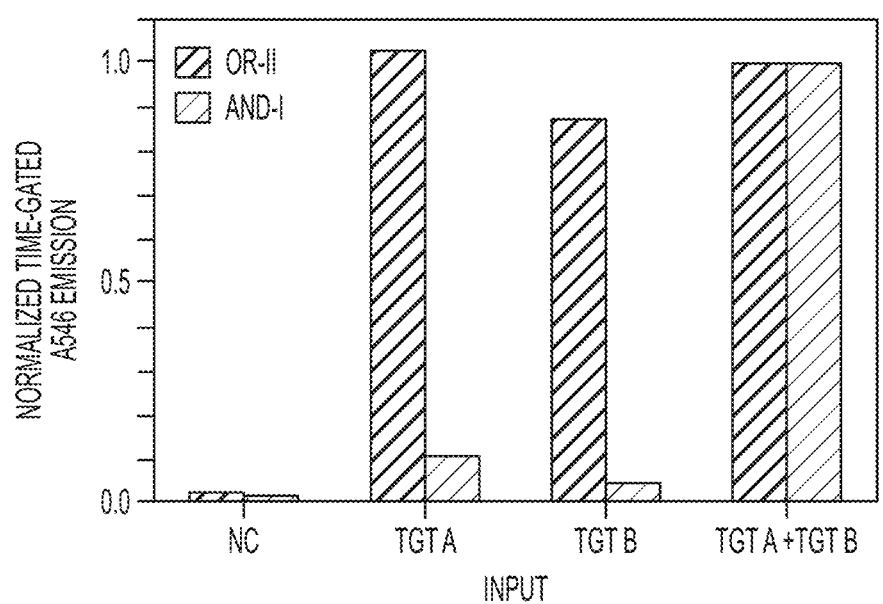
FIG. 30 shows time-gated A546 emission outputs for the OR-II and AND-I logical operators as a function of input: non-complementary (NC) DNA (0, 0), Target A (1, 0), Target B (0, 1), and both Target A and Target B (1, 1).

FIG. 30 shows the response of the OR-II operator alongside the AND-I operator. The OR-II operator provided time-gated A546 emission outputs of 0.02, 1.0, 0.9, and 1.0 for inputs of (0, 0), (1, 0), (0, 1) and (1,1), which is close to ideal behavior. There was also clear contrast versus the AND-I operator.

Figure 31:
FIG. 31 shows a truth table and schematics for the OR-III logical operator.
Figure 31:
Figure 31:
Figure 31:

OR III logical operator. FIG. 31 shows the concept of the OR-III logical operator. The operator consists of an unlabeled 33 nt template that is hybridized with the same reporter sequence as the AND-II gate; however, in this case the template hybridizes with only the first 15 nt of the reporter, leaving a 3 nt toehold. A one base pair mismatch is also introduced at the center of the reporter probe (see FIG. 3.14). A 13 nt IabFQ-labeled sequence hybridizes to the template adjacent to the reporter sequence and efficiently quenches the Tb (cf. quenching the A546 in OR-II), while leaving a 5 nt toehold on the template sequence. When target A is added (1, 0), it hybridizes to the template strand through toehold-mediated strand displacement of the blocking sequence, but the reporter sequence remains bound to the template. The IabFQ-labeled sequence is displaced, resulting in FRET from the Tb to the A546, and time-gated A546 emission as an output value of 1. When target B is added (0,1), it hybridizes to the reporter strand and displaces the reporter strand from the template, resulting in FRET from the Tb to the A546, and returns an output value of 1. When both targets are present (1,1), target A binds to the template, target B binds to the reporter strand (similar to the (1,0) an (0,1) inputs), resulting in FRET from the Tb to the A546 and time-gated emission as an output of 1.

Figure 32:
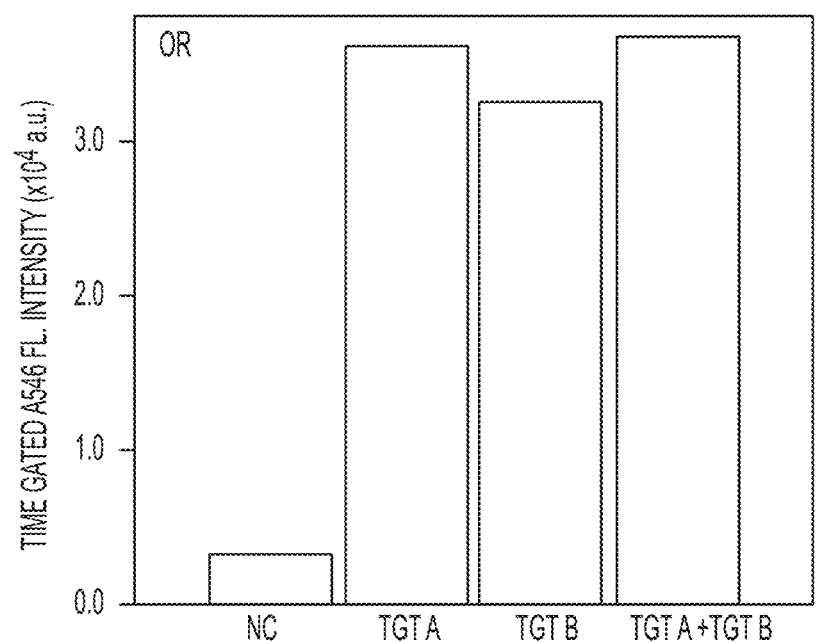
FIG. 32 shows time-gated A546 emission outputs for the OR-III logical operator as a function of input: non-complementary (NC) DNA (0, 0), Target A (1, 0), Target B (0, 1), and both Target A and Target B (1, 1).

FIG. 32 shows results from the OR-III logical operator. In the absence of any complementary oligonucleotide, the time-gated A546 emission has a normalized or logical output value of 0.1. The normalized time-gated emission increases to a value of 1.0 when either target is added, and also returns a value of 1.0 when both targets are added. OR logical operator function is achieved by setting a threshold value of 0.1.

Figure 33:
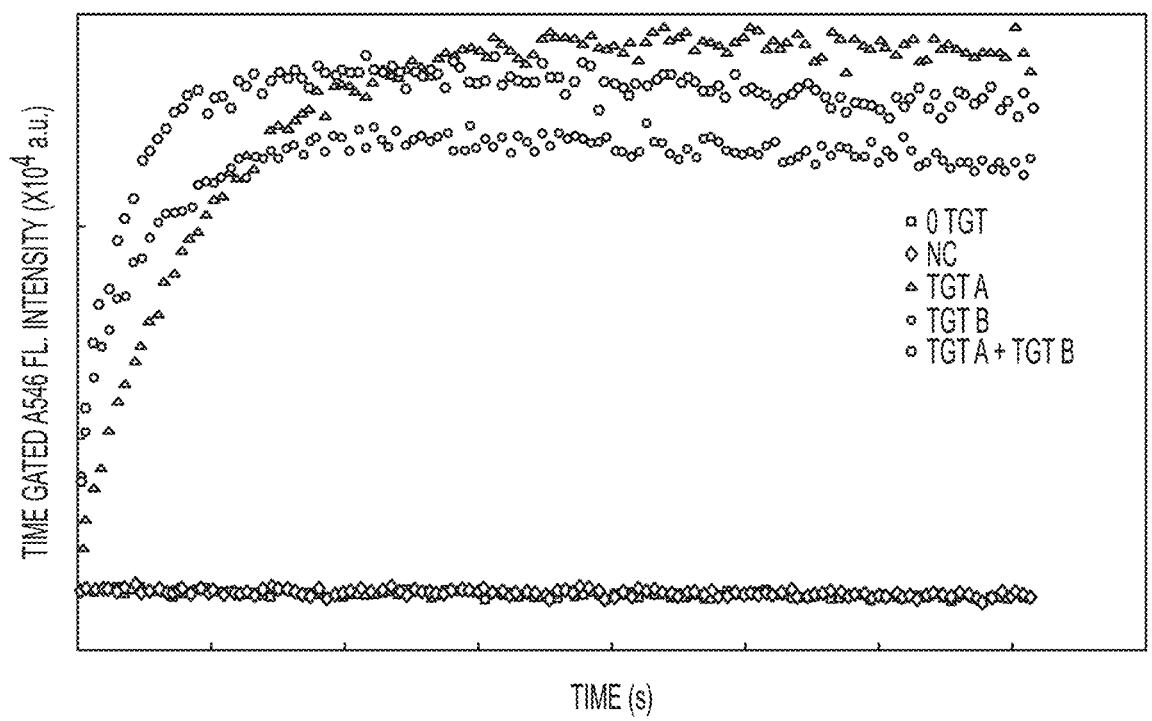
FIG. 33 shows the kinetics of OR III logical operator performance as a function of input: non-complementary (NC) DNA (0, 0), Target A (1, 0), Target B (0, 1), and both Target A and Target B (1, 1).

FIG. 33 shows progress curves for the kinetics of target input hybridization for each input of the OR-III logical operator. In the presence of one target or both targets (0,1, 1,0 or 1,1 state), the time-gated A546 fluorescence signal intensity increases, with response times of approximately 30 min for target A, 14 min for target B, and 10 min when both targets are present.

NAND Logical Operator.

Figure 34:
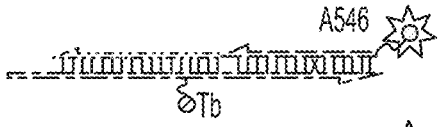
FIG. 34 shows a truth table and schematics for the NAND logical operator.
Figure 34:
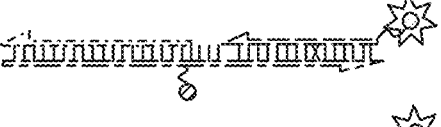
Figure 34:
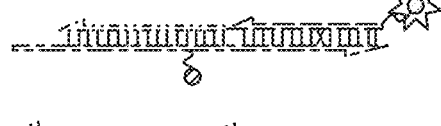
Figure 34:
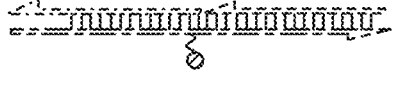

FIG. 34 shows the concept of the NAND logical operator. The operator consists of a 36 nt template with an internal Tb label in the middle of the sequence (between nt 18 and nt 19) that is hybridized with an A546 labeled 15 nt reporter containing a one base pair mismatch and no toehold. A 17 nt unlabeled blocking sequence hybridizes to the template adjacent to the reporter sequence and leaves a 5 nt toehold on the template sequence. The design is such that a 'hidden' toehold is created; the 17 nt unlabeled blocking sequence contains 13 nt that are complementary to the section of the template that binds target A and 3 nt that are complementary to the section of the template that binds target B (a 1 nt spacer is used to accommodate the Tb label on the template strand). Upon displacement of the blocking sequence by target A, a 3 nt toehold for target B is created. This design ensures that both inputs must be present in order to displace the A546 labeled reporter strand and return an output of 0. Since a NAND gate returns an output of 1 when no inputs are present, this construct does not contain a quencher label. The position of the Tb on the template strand and the A546 on the reporter strand leads to FRET from the Tb to the A546 and time-gated A546 emission as an output of 1 when no inputs are present. When target A is added (1, 0), it hybridizes to the template strand through toehold-mediated strand displacement of the blocking sequence, but the reporter sequence remains bound to the template. The unlabeled sequence is displaced, and FRET from the Tb to the A546 still returns a time-gated A546 emission output value of 1. When target B is added (0,1), it cannot displace the reporter strand since target A is not present to displace the blocking strand and reveal the toehold required for target B to bind. Since target B cannot bind, the reporter strand remains hybridized to the template, resulting in FRET from the Tb to the A546, and therefore still returns an output value of 1. However, when both targets are present (1,1), target A binds to the template, displaces the blocking strand and reveals the toehold for target B. Target B can then bind to the template strand and displace the reporter strand. Since the A546 labeled reporter strand is no longer in close enough proximity to the Tb donor, time-gated FRET emission from the A546 is not possible, and this loss of FRET from the Tb to the A546 returns an output of 0.

Figure 35:
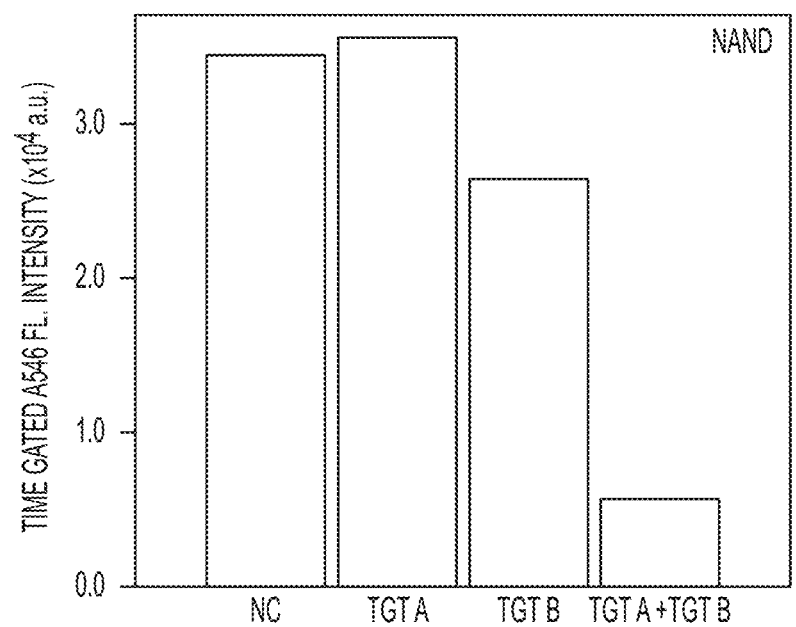
FIG. 35 shows the time-gated A546 emission outputs for the NAND logical operator as a function of input: non-complementary (NC) DNA (0, 0), Target A (1, 0), Target B (0, 1), and both Target A and Target B (1, 1).

FIG. 35 shows results from the NAND logical operator. In the absence of any complementary oligonucleotide, the time-gated A546 emission has a normalized logical output value of 1.0. The normalized time-gated emission also returns a value of 1.0 when target A is added, and returns a value of 0.2 when both targets are added. When target B is added, a value of ~0.74 is output. Ideally, target B should also have a logical output value of 1.0 since the hidden toehold should effectively only become available if target A is also present. The design of a hidden toehold may have functional validity; however, the blunt end of the duplex containing no toehold may still undergo breathing effects that are associated with the ends of DNA duplexes, leading to dynamic conformational fluctuations that could create a 'transient toehold' and lead to a displacement of the A546 reporter strand when only target B is introduced as an input. This would result in loss of the time-gated A546 emission. In the case of the template/reporter strand, the blunt end of the duplex contains two A-T base pairs. Breathing effects for A-T base pairs located at the ends of double stranded DNA (leading to fluctuation to open states) occurs more readily than for base pairs in the interior of a duplex and also occur more readily than ends containing G-C base pairs as a result of only two hydrogen bonding sites for A-T base pairs compared to three that exist for G-C.[10] The replacement of the blunt end A-T base pairs with G-C base pairs and hybridization conditions at higher ionic strength may ameliorate the displacement of the reporter strand when only target B is present and improve the NAND gate performance.

NOR Logical Operator.

Figure 36:
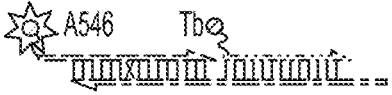
FIG. 36 shows a truth table and schematics for the NOR logical operator.
Figure 36:
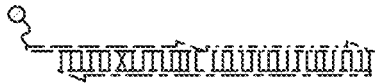
Figure 36:
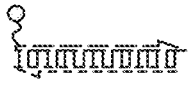
Figure 36:
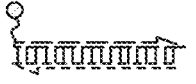

FIG. 36 shows the concept of the NOR logical operator. The NOR operator contains the same oligonucleotide sequences as the OR-III operator; however, the position of the Tb label has been moved to the blocking strand. This places the A546 and Tb labels on different strands. The Tb label now occupies the same position as that of the IaBLK FQ quencher label on the OR-III operator. The position of the Tb on the blocking strand and the A546 on the reporter strand leads to FRET from the Tb to the A546 and time-gated A546 emission as an output of 1 when no inputs are present. When target A is added (1, 0), it hybridizes to the template strand through toehold-mediated strand displacement of the blocking sequence, but the reporter sequence remains bound to the template. The Tb-labeled sequence is displaced, resulting in loss of FRET from the Tb to the A546, and returns an output value of 0. When target B is added (0,1), it hybridizes to the reporter strand and displaces the reporter strand from the template, also resulting in loss of FRET from the Tb to the A546, and returns an output value of 0. When both targets are present (1,1), target A binds to the template, and target B binds to the reporter strand. This results in loss of FRET from the Tb to the A546 and returns an output of 0.

Figure 37:
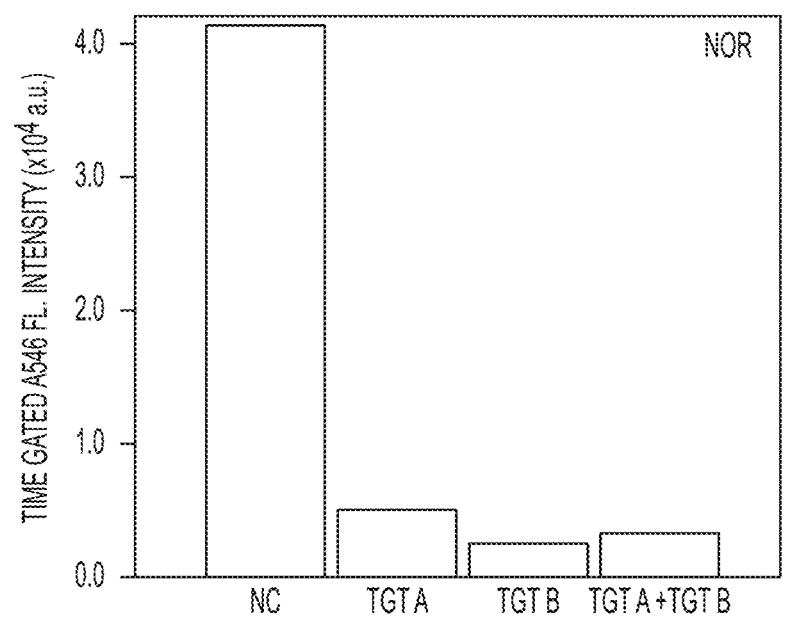
FIG. 37 shows time-gated A546 emission outputs for the NOR logical operator as a function of input: non-complementary (NC) DNA (0, 0), Target A (1, 0), Target B (0, 1), and both Target A and Target B (1, 1).

FIG. 37 shows results from the NOR logical operator. In the absence of any complementary oligonucleotide, the time-gated A546 emission has a normalized or logical output value of 1.0. The normalized time-gated emission returns a value of 0.1 or less when either target is added, and similarly returns a value of <0.1 when both targets are added. OR logical operator function is achieved by setting a threshold value of 0.1.

Simultaneous Use of an AND/OR Gate Combination.

Figure 38:
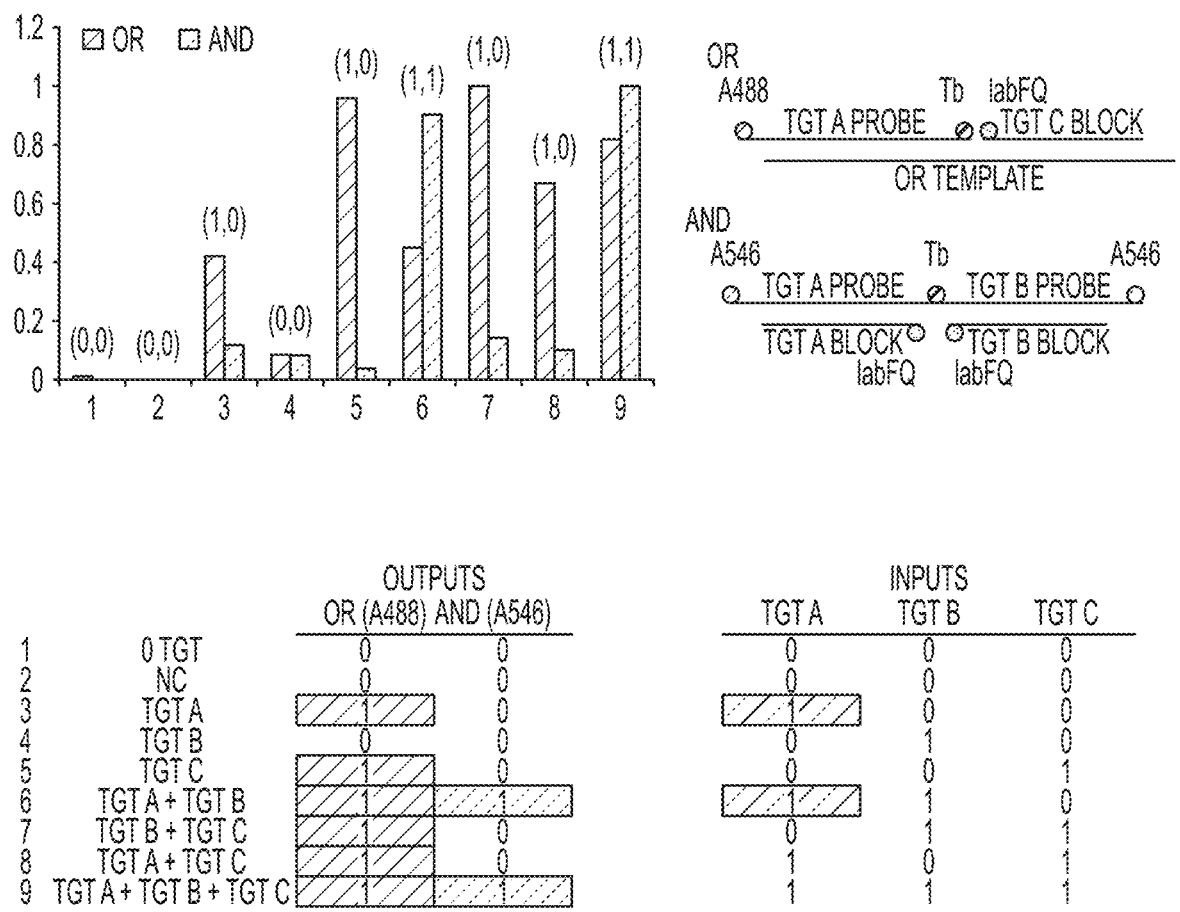
FIG. 38 shows time-gated, two-color A488 and A546 emission outputs for a mixture containing both AND and OR logical operators.

As a preliminary step toward developing functional molecular logic device circuitry using the logical operators designed here, the AND-I logical operator and a modified OR-III logical operator were used simultaneously, and their performance was evaluated. For the modified OR-III logical operator, the same basic design was used, but the template was modified so that a third target oligonucleotide (target C) could be detected. Also, the A546 reporter dye was replaced with an A488 reporter dye so that a two-colour analysis of target binding could be observed. Since Tb has four distinct time-gated fluorescence emission peaks, it can be readily used for multiplexed detection of multiple targets using different fluorescent dyes as FRET acceptors. FIG. 38 shows the results of a two-colour analysis of AND/OR gate performance. The AND and OR gates were pre-assembled separately, then subsequently mixed together in a 1:1 ratio. Targets A, B, and C were introduced in various combinations, as outlined in FIG. 38. The resulting outputs are also shown in FIG. 38. The performance of the AND gate was better than that of the OR gate when combined in the same solution. This may suggest that the logical operator design is sequence dependent since the original OR-III design, which was the same with respect to length/position of toeholds and template/probe/block geometry performed well as an OR logical operator. In the OR design here, the sequences for detecting target B were replaced with the sequences for detecting target A, and the sequences for detecting target A were replaced with sequences capable of detecting target C. Therefore, changing the sequences may have led to a decrease in performance for the OR gate. However, despite a sub-optimal performance from the OR logical operator, there is clear evidence that the AND and OR logical operators can be combined and still function as discrete constructs in a mixture. While further optimization is required, this is an important first step towards the use of the logical operators designed here for molecular circuitry and multiplexed analyses.

3.4 CONCLUSIONS

We have developed two functional AND operators, two functional OR operators, one functional NAND operator, and one functional NOR operator. Each operator accepts complementary oligonucleotide sequences as inputs and modulates the time-gated A546 emission intensity as output. The OR operator that does not function adequately was limited by single-stranded DNA in two of its states, and has been improved by using the OR-II and OR-III designs. Ongoing and future work includes measurement of calibration curves for all operators, tests in serum, optimizing the use of combinations of the logical operators in tandem, and higher-resolution measurements of the Tb and A546 lifetimes in each state for each operator. The latter experiments will aim to elucidate the signaling mechanism for each operator. Subsequent experiments will focus on expanding these operators to accommodate more than two inputs, stringing multiple operators together for simple molecular computation circuits, optimizing the performance of the NAND logical operator, and investigating the potential to use NAND or NOR logical operators to create universal logic operators.

3.5 REFERENCES

1. Andreasson, J.; Pischel, U., Smart Molecules at Work-Mimicking Advanced Logic Operations. *Chemical Society Reviews* 2010, 39, 174-188.
2. Balzani, V.; Credi, A.; Venturi, M., Molecular Logic Circuits. *Chemphyschem* 2003, 4, 49-59.
3. de Silva, A. P.; Uchiyama, S., Molecular Logic and Computing. *Nature Nanotechnology* 2007, 2, 399-410.
4. Katz, E.; Privman, V., Enzyme-Based Logic Systems for Information Processing. *Chemical Society Reviews* 2010, 39, 1835-1857.
5. Pischel, U., Chemical Approaches to Molecular Logic Elements for Addition and Subtraction. *Angewandte Chemie International Edition* 2007, 46, 4026-4040.
6. Raymo, F. M., Digital Processing and Communication with Molecular Switches. *Advanced Materials* 2002, 14, 401-+.
7. Silvi, S.; Constable, E. C.; Housecroft, C. E.; Beves, J. E.; Dunphy, E. L.; Tomasulo, M.; Raymo, F. M.; Credi, A., All-Optical Integrated Logic Operations Based on Chemical Communication between Molecular Switches. *Chemistry—a European Journal* 2009, 15, 178-185.
8. Wang, J.; Katz, E., Digital Biosensors with Built-in Logic for Biomedical Applications-Biosensors Based on a Biocomputing Concept. *Analytical and Bioanalytical Chemistry* 2010, 398, 1591-1603.
9. Zhang, D. Y.; Seelig, G., Dynamic DNA Nanotechnology Using Strand-Displacement Reactions. *Nature Chemistry* 2011, 3, 103-113.
10. Jose, D.; Datta, K.; Johnson, N. P.; von Hippel, P. H., Spectroscopic Studies of Position-Specific DNA "Breathing" Fluctuations at Replication Forks and Primer-Template Junctions. *Proc. Natl. Acad Sci. U.S.A.* 2008, 106, 4231-4326.

4. FURTHER REFERENCES

Patent Documents

WO 2015/181,101 A1. Multiplexed homogenous oligonucleotide detection. Hildebrandt, N.; Zongwen, J.
WO 2010/084,015 A1. Method for detecting an analyte in a sample by multiplexing FRET analysis and kit. Hildebrandt, N.; Geißler, D.; Löhmannsröben, H.-G.; Bois, E.; Charbonniere, L.; Ziessel, R.
WO 2008/092,120 A1. Multi-color time resolved fluorophores based on macrocyclic lanthanide complexes. Butlin, N. G.; Corneillie, T. M.; Xu, J.

Other Publications

Clegg, R. M.: Förster resonance energy transfer—FRET what is it, why do it, and how it's done. In: Laboratory Techniques in Biochemistry and Molecular Biology, Volume 33 FRET and FLIM Techniques; Gadell, T. W. J. (Ed.). Elsevier, 2011, pp. 1-57.

The invention claimed is:

1. A system for computing logical operations comprising
a first oligonucleotide covalently attached to a long-lifetime luminophore with an emission lifetime of at least one millisecond and configured as a donor in a FRET process;
at least a second oligonucleotide complementary to the first oligonucleotide;
at least one fluorescent dye with an emission lifetime of less than 100 nanoseconds configured as an acceptor in the FRET process covalently attached to one of the oligonucleotides; and
optionally, at least one quencher of fluorescence configured as a quencher of the FRET process covalently attached to one of the oligonucleotides,
wherein the system is configured so that an input condition corresponding to the presence or absence of either of one or two oligonucleotide targets complementary to one of the oligonucleotides but distinct from both results in an output condition based on the presence or absence of a FRET process between the a long-lifetime luminophore and the fluorescent dye;
wherein the long-lifetime luminophore and the fluorescent dye with an emission lifetime of less than 100 nanoseconds are positioned at a sweet spot distance calculated to balance FRET efficiency and lag time from $$\frac{dD^*}{dt} = -\frac{D^*}{\tau_D}(1+\gamma) \text{ and } \frac{dA^*}{dt} = -\frac{A^*}{\tau_A} + \frac{\gamma D^*}{\tau_D}$$

where $D^*$ and $A^*$ are the probabilities that a donor and acceptor are in an excited state, respectively, $\tau$ is an excited state lifetime, and $\gamma$ represents Förster coupling; and
the sweet spot distance is less than a predicted Förster distance of the FRET process.

* * * * *